US012763200B2

(12) United States Patent
Toth et al.

(10) Patent No.: US 12,763,200 B2

(45) Date of Patent: Oct. 13, 2026

(54) WEARABLE SENSOR SYSTEM CONFIGURED FOR MONITORING AND MODELING HEALTH DATA

(71) Applicant: LifeLens Technologies, Inc., Ivyland, PA (US)

(72) Inventors: Landy Toth, Doylestown, PA (US); Robert S. Schwartz, Inver Grove Heights, MN (US)

(73) Assignee: LifeLens Technologies, Inc., Ivyland, PA (US)

(*) Notice: Subject to any disclaimer, the term of this patent is extended or adjusted under 35 U.S.C. 154(b) by 261 days.

(21) Appl. No.: 18/010,123

(22) PCT Filed: Jul. 13, 2021

(86) PCT No.: PCT/US2021/041414

§ 371 (c)(1),
(2) Date: Dec. 13, 2022

(87) PCT Pub. No.: WO2022/015719

PCT Pub. Date: Jan. 20, 2022

(65) Prior Publication Data

US 2023/0245767 A1 Aug. 3, 2023

Related U.S. Application Data

(60) Provisional application No. 63/052,417, filed on Jul. 15, 2020.

(51) Int. Cl.

*G16H 40/63* (2018.01)
*A61B 5/00* (2006.01)

(Continued)

(52) U.S. Cl.

CPC .......... *G16H 40/63* (2018.01); *A61B 5/7275* (2013.01); *A61B 5/747* (2013.01); *G16H 20/30* (2018.01); *G16H 50/20* (2018.01); *G16H 50/80* (2018.01)

(58) Field of Classification Search

None

See application file for complete search history.

(56) References Cited

U.S. PATENT DOCUMENTS

| | | | | |
|---|---|---|---|---|
| 11,011,277 | B1 * | 5/2021 | Kelly | G16H 40/67 |
| 11,504,011 | B1 * | 11/2022 | Jain | G06N 5/04 |

(Continued)

FOREIGN PATENT DOCUMENTS

| | | | | |
|---|---|---|---|---|
| IN | 202011013950 A * | 3/2020 | | A61B 10/00 |
| WO | 2014197822 A2 | 12/2014 | | |

(Continued)

OTHER PUBLICATIONS

Teng et al. Wearable Medical Systems for p-Health, IEEE Reviews in Biomedical Engineering, vol. 1, 2008.*

(Continued)

*Primary Examiner* — David J Stoltenberg

(74) *Attorney, Agent, or Firm* — Ryan, Mason & Lewis, LLP

(57) ABSTRACT

An apparatus comprises at least one processing device configured to generate a model of an outbreak of a disease based on physiological monitoring and location data received from wearable devices of a plurality of users, to determine a first subset of the plurality of users that have potentially contracted the disease based on a comparison of the physiological monitoring data and known symptoms of the disease, to identify a second subset of the plurality of users that are at risk for contracting the disease from the first subset of the plurality of users utilizing the model of the (Continued)

outbreak of the disease and the location data, and to generate notifications for delivery to the plurality of users comprising information related to outbreak of the disease and measures for at least one of treating and mitigating spread of the disease.

20 Claims, 18 Drawing Sheets

(51) Int. Cl.
*G16H 20/30* (2018.01)
*G16H 50/20* (2018.01)
*G16H 50/80* (2018.01)

(56) References Cited

U.S. PATENT DOCUMENTS

| | | | | |
|---|---|---|---|---|
| 2008/0269571 | A1* | 10/2008 | Brown | G16H 10/20<br>600/300 |
| 2009/0082997 | A1* | 3/2009 | Tokman | G16H 50/80<br>702/179 |
| 2011/0125525 | A1* | 5/2011 | Lung | G16H 10/60<br>705/2 |
| 2012/0154139 | A1* | 6/2012 | Dupoteau | G08B 27/005<br>340/539.1 |
| 2013/0031179 | A1* | 1/2013 | Christakis | G06Q 10/10<br>709/204 |
| 2013/0318027 | A1* | 11/2013 | Almogy | G16H 50/20<br>706/52 |
| 2016/0132652 | A1* | 5/2016 | Chapman Bates | G16H 50/20<br>706/11 |
| 2017/0177724 | A1* | 6/2017 | Booker | G06F 16/24 |
| 2018/0144103 | A1* | 5/2018 | Chae | G16H 50/70 |
| 2018/0322941 | A1* | 11/2018 | Krishnan | G16H 10/40 |
| 2018/0374582 | A1* | 12/2018 | Holmes | G16H 50/50 |
| 2019/0209022 | A1* | 7/2019 | Sobol | H04W 4/80 |
| 2019/0252078 | A1* | 8/2019 | Schubert | G06N 3/044 |
| 2019/0333646 | A1* | 10/2019 | Shaw | G06F 7/00 |
| 2020/0004746 | A1* | 1/2020 | Randall | G06F 16/2455 |
| 2020/0254259 | A1* | 8/2020 | Libbus | A61N 1/36053 |
| 2020/0294680 | A1* | 9/2020 | Gupta | G16H 40/20 |
| 2021/0050116 | A1* | 2/2021 | Sabeti | G06Q 10/40 |
| 2021/0296008 | A1* | 9/2021 | Novak, Jr. | A61B 5/746 |
| 2021/0391072 | A1* | 12/2021 | Ergen | G16H 50/80 |
| 2022/0285036 | A1* | 9/2022 | Merjanian | G16H 50/80 |

FOREIGN PATENT DOCUMENTS

| | | | |
|---|---|---|---|
| WO | 2016019250 | A1 | 2/2016 |
| WO | 2017173331 | A1 | 10/2017 |
| WO | 2017190049 | A1 | 11/2017 |

OTHER PUBLICATIONS

Subhas Chandra Mukhopadhyay, Wearable Sensors for Human Activity Monitoring: A Review, IEEE Sensors Journal, vol. 15, No. 3, Mar. 2015.*
Ding et al., Wearable Sensing and Telehealth Technology with Potential Applications in the Coronavirus Pandemic, IEEE Reviews in Biomedical Engineering, vol. 14, 2021.*
Cesario et al. Time-based geographical mapping of communicable diseases; 2012 16th International Conference on Information Visualisation.*
International Search Report and Written Opinion of PCT/US2021/041414 dated Oct. 19, 2021, 13 pages.
G. Zhu et al., "Learning from Large-Scale Wearable Device Data for Predicting the Epidemic Trend of COVID-19," https://onlinelibrary.wiley.com/doi/epdf/10.1155/2020/6152041, May 5, 2020, 8 pages.
Supplementary European Search Report of European Patent Application No. 21842660.9, dated May 29, 2024, 10 pages.

* cited by examiner

400

| | USER PROFILE FIELD | FIELD DATA |
|---|---|---|
| 402 | NAME/SEX | JOHN DOE/MALE |
| 404 | AGE | 43 |
| 406 | WEIGHT | 205 |
| 408 | HEIGHT | 6’ |
| 410 | KNOWN DISEASES AND DISORDERS | ASTHMA |
| 412 | EMERGENCY CONTACT | JANE DOE |
| 414 | NEXT OF KIN | JANE DOE |
| 416 | PREFERRED HOSPITAL | JOHNS HOPKINS |
| 418 | PRIMARY CARE PHYSICIAN (PCP) | DR. BOB SMITH |

WEARABLE SENSOR SYSTEM CONFIGURED FOR MONITORING AND MODELING HEALTH DATA

TECHNICAL FIELD

The present disclosure relates to the field of physiologic monitoring and, more particularly, to devices and systems for physiologic monitoring in responding to health crises.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

During disasters, including pandemics and other emergencies, limited surge capacity of health care facilities may lead to severe resource scarcity. Better tools and technologies are needed to help allocate resources that are both equitable and maximize benefit to the population at large during such emergencies.

Global health crises, such as outbreaks of viruses, biological pathogens, epidemics, pandemics and other mass emergencies, represent significant threats to mankind in terms of mortality, injuries, chaotic reaction of civilians and response organizations, economic impacts, etc. With over half the world population now living in urban areas, the complexity of the response phase is also increasing in terms of search and rescue across many international locations, rapid and effective assistance for large numbers of persons, including potentially large numbers of casualties, across a wide area with medical aid and/or supplies. Main communications networks may also experience overload, and there may be delay or damage to response infrastructure such as transport, energy and medical facilities, and difficulties in logistics and distribution of aid resources. Similarly, with large scale pandemics the mass need for medical attention, patient volumes and need for substantial resources in terms of large scale medical assistance, as well as sanitary habitat and infrastructure in the days, weeks, and months following the start of a pandemic, is significant and can result in considerable threat to life, medical needs and other problems if not addressed and managed properly.

SUMMARY

One illustrative, non-limiting objective of this disclosure is to provide systems, devices, methods, and kits for global pandemic response, such as viral epidemics. More particularly, such systems, devices, methods and kits may be used for rapid detection, qualified assessment and monitoring of pandemics and electronic triage of victims, communication, alert and treatment systems, provision of suitable modular sensing and/or aid solutions, and their rapid deployment via delivery platforms such as mobile applications and networks, telemedicine, prescription fulfillment, or pre-deployment of medical resources. Another illustrative, non-limiting objective of this disclosure is to provide vital physiological monitoring systems and, more specifically, to provide vital physiological monitoring systems for responding to local, national and global health crises.

The above illustrative, non-limiting objectives are wholly or partially met by devices, systems, and methods according to the appended claims in accordance with the present disclosure. Features and aspects are set forth in the appended claims, in the following description, and in the annexed drawings in accordance with the present disclosure.

In some embodiments, an apparatus comprises at least one processing device comprising a processor coupled to a memory. The at least one processing device is configured to generate a model of an outbreak of a disease, the model of the outbreak of the disease being based at least in part on physiological monitoring data and location data received from a plurality of wearable devices associated with a plurality of users. The at least one processing device is also configured to determine at least a first subset of the plurality of users that have potentially contracted the disease based at least in part on a comparison of the received physiological monitoring data and known symptoms of the disease and to identify at least a second subset of the plurality of users that are at risk for contracting the disease from the first subset of the plurality of users utilizing the model of the outbreak of the disease and the received location data for the plurality of users. The at least one processing device is further configured to generate one or more notifications for delivery to at least one of the first and second subsets of the plurality of users, the one or more notifications comprising information related to outbreak of the disease and measures for at least one of treating the disease and mitigating spread of the disease.

The at least one processing device may be further configured to identify at least a third subset of the plurality of users associated with one or more essential workforces. The at least one processing device may be further configured to modify at least a given one of the one or more notifications prior to delivering the given notification to users in the third subset of the plurality of users. At least a given one of the users in the third subset of users may also be in one of the first subset of the plurality of users and the second subset of the plurality of users.

The at least one processing device may be further configured to deliver at least a given one of the one or more notifications to at least a given one of the plurality of users responsive to determining that the given user is in a geographic location associated with the outbreak of the disease. The geographic location associated with the outbreak of the disease may comprise a geographic region where at least one of the users in the first subset of the plurality of users is known to have been present within a designated threshold period of time of when the physiological monitoring data for said at least one user is indicative of one or more of the known symptoms of the disease. The geographic location associated with the outbreak of the disease may comprise a geographic region where at least one of a quarantine, social distancing, stay-at-home and self-isolation order is in effect.

The at least one processing device may be further configured to provide information associated with the first subset of the plurality of users to one or more third parties responsible for monitoring the outbreak of the disease. The one or more third parties may comprise at least one of a local, state, federal and global health network. The information associated with the first subset of the plurality of users may comprise at least one of: the received physiological monitoring data for the first subset of the plurality of users; the received location data for the first subset of the plurality of users; and one or more health indicators derived from at least a portion of at least one of the received physiological monitoring data and the received location data for the first subset of the plurality of users. The information associated with the first subset of the plurality of users may be modified prior to being provided to the one or more third parties in accordance with data security rules regarding transfer of at least one of the received physiological monitoring data and the received location data of the first subset of the plurality of users. Modifying the information associated with the first subset of the plurality of users may comprise at least one of encrypting and anonymizing the information associated with the first subset of the plurality of users.

The at least one processing device may be further configured to provide information associated with the first subset of the plurality of users to one or more third parties responsible for providing care to the first subset of the plurality of users.

Determining the first subset of the plurality of users that have potentially contracted the disease may comprise, for a given user in the first subset of the plurality of users: calculating one or more health indicators for the given user based on the received physiological monitoring data for the given user and a user profile of the given user; identifying one or more other users with user profiles exhibiting at least a threshold level of similarity to the user profile of the given user that are known to have the disease; and correlating the one or more health indicators for the given user with health indicators for the one or more other users utilizing one or more statistical measures.

At least a given one of the one or more notifications may be generated based at least in part on receiving one or more location-related health alerts from one or more third parties, and the at least one processing device may be further configured to deliver the given notification to at least a given one of the plurality of users responsive to detecting entry of the given user to a given geographic region associated with at least one of the one or more location-related health alerts.

Identifying the second subset of the plurality of users that are at risk for contracting the disease from the first subset of the plurality of users may comprise determining colocation of at least a first user in the first subset of the plurality of users with at least a second user in the second subset of the plurality of users, wherein determining colocation is based at least in part on global positioning system information, ultra-wideband information and ambient audio information in the received location data for the first user and the second user.

Generating the model of the outbreak of the disease may comprise updating the model of the outbreak of the disease based at least in part on trends of symptom severity for the known symptoms exhibited by the first subset of the plurality of users characterizing progression of the disease over time.

At least a given one of the one or more notifications may be generated in response to receiving at least one of a quarantine, social distancing, stay-at-home and self-isolation order for one or more geographic regions, the given notification comprising instructions for following said at least one quarantine, social distancing, stay-at-home and self-isolation order based on the received physiological monitoring data for the plurality of users.

In some embodiments, a computer program product comprises a non-transitory processor-readable storage medium having stored therein executable program code which, when executed, causes at least one processing device to generate a model of an outbreak of a disease, the model of the outbreak of the disease being based at least in part on physiological monitoring data and location data received from a plurality of wearable devices associated with a plurality of users. The executable program code, when executed, also causes the at least one processing device to determine at least a first subset of the plurality of users that have potentially contracted the disease based at least in part on a comparison of the received physiological monitoring data and known symptoms of the disease and to identify at least a second subset of the plurality of users that are at risk for contracting the disease from the first subset of the plurality of users utilizing the model of the outbreak of the disease and the received location data for the plurality of users. The executable program code, when executed, further causes the at least one processing device to generate one or more notifications for delivery to at least one of the first and second subsets of the plurality of users, the one or more notifications comprising information related to outbreak of the disease and measures for at least one of treating the disease and mitigating spread of the disease.

In some embodiments, a method comprises generating a model of an outbreak of a disease, the model of the outbreak of the disease being based at least in part on physiological monitoring data and location data received from a plurality of wearable devices associated with a plurality of users. The method also comprises determining at least a first subset of the plurality of users that have potentially contracted the disease based at least in part on a comparison of the received physiological monitoring data and known symptoms of the disease and identifying at least a second subset of the plurality of users that are at risk for contracting the disease from the first subset of the plurality of users utilizing the model of the outbreak of the disease and the received location data for the plurality of users. The method further comprises generating one or more notifications for delivery to at least one of the first and second subsets of the plurality of users, the one or more notifications comprising information related to outbreak of the disease and measures for at least one of treating the disease and mitigating spread of the disease. The method is performed by at least one processing device comprising a processor coupled to a memory.

BRIEF DESCRIPTION OF THE DRAWINGS

Several aspects of the disclosure can be better understood with reference to the following drawings. In the drawings, like reference numerals designate corresponding parts throughout the several views.

DETAILED DESCRIPTION

Figure 1:
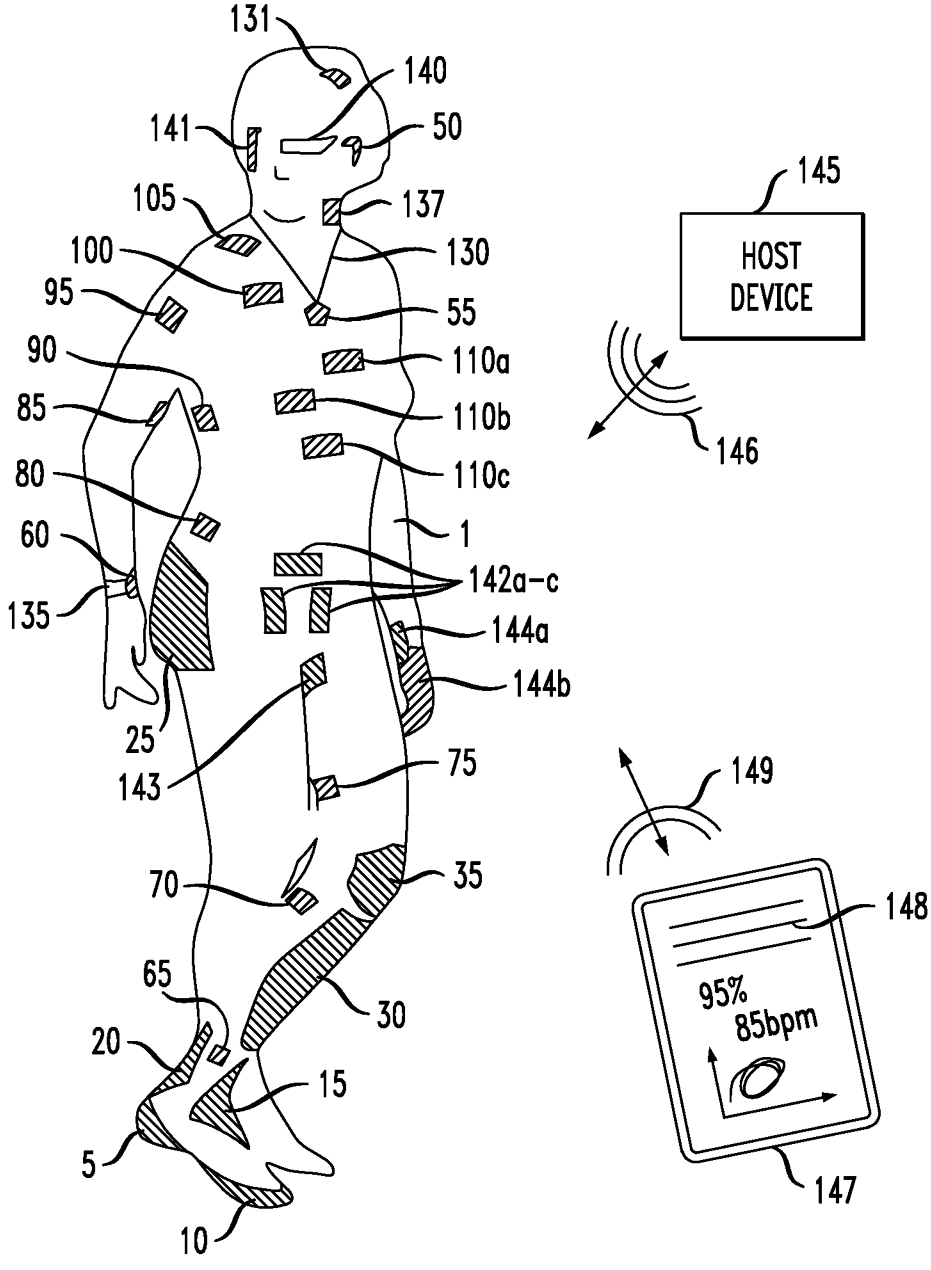
FIG. 1 illustrates aspects of a modular physiologic monitoring system, according to an embodiment of the invention.

Particular embodiments of the present disclosure are described herein below with reference to the accompanying drawings; however, the disclosed embodiments are merely examples of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

The accompanying drawings illustrate various embodiments of systems, methods, and embodiments of various other aspects of the disclosure. One of ordinary skill in the art will appreciate that the illustrated element boundaries (e.g. boxes, groups of boxes, or other shapes) in the figures represent one example of the boundaries. It may be that in some examples, one element may be designed as multiple elements or that multiple elements may be designed as one element. In some examples, an element shown as an internal component of one element may be implemented as an external component in another and vice versa. Furthermore, elements may not be drawn to scale. It is also noted that components and elements in the figures are not necessarily drawn to scale, emphasis instead being placed upon illustrating principles.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred systems and methods are now described.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

Coronavirus disease 2019 (COVID-19) is an infectious disease caused by a newly discovered coronavirus. In late 2019, the disease began to spread from its origin in the Hubei province of China, and by early 2020, there were reported cases in nearly all developed nations. While symptoms to many young, healthy individuals may be mild (e.g., runny nose, sore throat, cough, fever, difficulty breathing in severe cases), the disease can be fatal to the elderly and/or those with comorbidities. The virus is also highly infectious, allowing a single individual to infect thousands of others in a short period of time through the course of normal social interactions.

In the most extreme cases, COVID-19 has contributed to deaths of thousands of individuals due to constrained medical resources. While many otherwise healthy people successfully recover from COVID-19 without medical intervention, many others may need specific medical treatments and tools, such as respiratory ventilators, continuous positive air pressure (CPAP) devices, oxygen tanks, etc., which can be scarce in times of crisis. Scarcity of these life-saving devices can increase the rate of mortality in specific locations if the local medical system becomes overwhelmed. A demonstration of the speed at which local medical systems may become overwhelmed will now be discussed with respect to progression of COVID-19 in Italy, where it took less than two months to go from a first confirmed case to becoming the world's center of active COVID-19 cases.

In Italy, infection rates and comorbidity quickly overwhelmed the medical system and caused higher rates of death associated with COVID-19 than may otherwise have been necessary. Due to the ongoing worldwide pandemic of COVID-19, a novel infectious disease caused by severe acute respiratory syndrome coronavirus 2 (SARS-CoV-2) was first confirmed to have spread to Italy on Jan. 31, 2020, when two Chinese tourists in Rome tested positive for the virus. One week later, an Italian man repatriated back to Italy from the city of Wuhan in China and was hospitalized and confirmed as the third case in Italy. A cluster of cases was later detected, starting with 16 confirmed cases in Lombardy on Feb. 21, 2020, and 60 additional cases and the first deaths on Feb. 22, 2020. By the beginning of March, the virus had spread to all regions of Italy. As of Mar. 22, 2020, Italy was the world's center of active COVID-19 cases with 46,638 active cases—more than double the number of active cases of any other country. The total number of confirmed COVID-19 cases in Italy has continued to rise to over 50,000, with over 5,000 deaths. On Mar. 19, 2020, Italy became the country with the highest number of confirmed deaths in the world.

Most people infected with the COVID-19 virus will experience mild to moderate respiratory illness and recover without requiring special treatment. Older people, and those with underlying medical problems like cardiovascular disease, diabetes, chronic respiratory disease, and cancer, are more likely to develop serious illness. The COVID-19 virus spreads primarily through droplets of saliva or discharge from the nose when an infected person coughs or sneezes. At this time, there are various vaccines for COVID-19. There are many ongoing clinical trials evaluating additional vaccines and potential treatments.

Mitigation of the spread of COVID-19 has presented significant challenges for world, national and state or other local governments, as well as local medical facilities and individuals. Quarantines and self-isolation may slow the spread, but are difficult and problematic to enforce, and also cause significant negative economic impact which endangers vulnerable members of society. Moreover, the fear and panic caused by worldwide pandemics may cause individuals to associate very common symptoms of COVID-19 with the virus itself and seek medical treatment. Medical centers like hospitals, clinics, and family doctors' offices may thus become centers of infection, as infected and unaffected patients may begin to frequent these centers seeking treatment, exposing other patients and medical staff to the viral pathogens. Though the tools may exist to self-diagnose the risk factors for COVID-19, current medical tools and systems are ill-equipped to respond to such large numbers of cases in short periods of time.

Current medical equipment is designed for precise measurement of vital signs (e.g., temperature, respiratory rate, pulse oximetry, heart rate, blood pressure, etc.) of a single patient, and the medical equipment used in hospitals and medical centers around the world may cost hundreds, thousands, or hundreds of thousands of dollars, making widespread monitoring of patient disease states and risk factors impractical. There exists a need for efficient monitoring of global populations who may be at risk for diseases of international significance, such as COVID-19. Such efficient monitoring could be provided at low cost to thousands or millions of individuals at risk for the disease. By using telemedical tools and remote monitoring of low cost vital sign detection devices, caregivers can effectively triage patients without exposing medical centers and their patients to pathogens, and thus help slow the spread of the disease. Moreover, if the devices and thus data were standardized, the data may be provided to world health organizers monitoring the spread of disease and enable allocation of resources to where it may be most needed.

There exists a need for low cost, standardized devices to be provided to individuals at risk in a global health pandemic, which can in turn provide health data to local, state, federal, and world health organizations. Such information can be made wirelessly available to amplify the decision-making capabilities of small care teams, enabling them to manage and direct critical care resources to a large number of dispersed patients at once. This enhanced capability allows health care leaders to organize efficiently, optimizing the marshaling of resources around high-need patients. Among other applications, the deployment of such monitoring devices enables rapid, safe observation of individuals during periods of high load on a health care system, such as during disease outbreaks and epidemics. Under such conditions, widespread deployment of easy-to-use personal monitoring equipment can help in effecting triage, quarantining infected populations, blunting hospital-based caseload, and providing precision care. Aspects of the present invention may be used to contribute to the overall slowing or limiting of disease impacts while minimizing general socioeconomic disruption, both short-term and long-term. In addition, data collected by low cost and widespread monitoring devices could aid providers and agencies at multiple scales in predictive and retrospective epidemiology, equipping global health care systems to manage new or emerging threats in the future. The present invention describes examples of such systems.

One of the major challenges associated with global health pandemics is establishing systems for widespread monitoring and modeling of global health data, specifically data associated with population level health status. Typically, these systems are set up more or less ad hoc, where local medical systems report health data to global health organizations on a case by case basis. Even during times of global crisis that engender international mandates for rapid response and reporting, medical systems may experience considerable delay in reporting health data. Much of this delay may be logistical in nature. The medical systems may have challenges collecting the data, standardizing the format of the data, standardizing the analysis and the reporting of data, facilitating the transfer of data and the attendant securities associated with transferring health data, etc.

Moreover, even if data transfer between local medical systems and world health organizations is timely, the data may be necessarily incomplete. The medical systems typically only have robust health data for inpatient care, leaving the vast majority of health data associated with outpatients unreported. These unreported outpatients present a significant challenge for monitoring and modelling the spread of infectious disease. With highly infectious diseases, such as COVID-19, one of the challenges with pathogen containment is that patients with relatively mild symptoms, or no known experienced symptoms at all, may continually spread the disease unaware of their contagiousness. There exists a need for more widespread monitoring of outpatients and robust systems of notification to inform outpatients of the risk of infection.

Additionally, contact between individuals may be a central cause of the spread of infectious diseases, such as COVID-19. Though government entities may impose restrictions on person to person contact, it is difficult to enforce compliance of such restrictions. Monitoring and modelling of contact between individuals are not possible with current medical systems that do not incorporate wearable medical device data, which could provide automatic contract tracing using global positioning system (GPS) and ultrawideband (UWB) radio monitoring. There exists a need to automatically track contact between individuals for widespread monitoring and modelling of global health crises.

Illustrative embodiments provide innovative solutions for monitoring and modeling the progress of disease amongst a widespread population. Such solutions are particularly valuable in times of global health crisis. A low-cost, widely scalable, physiological monitoring system could provide individuals with critical analysis of vital data indicating their risk of disease and infection, and provide world health organizations and local medical centers with data to more accurately monitor and model the spread of disease, enabling more efficient resource allocation, medical triage, and dissemination of critical medical information to patients and caregivers.

One illustrative, non-limiting objective of this disclosure is to provide systems, devices, methods, and kits for monitoring physiologic and/or physical signals from a subject. Another illustrative, non-limiting objective is to provide simplified systems for monitoring subjects. Another illustrative, non-limiting objective is to provide comfortable long-term wearable systems for monitoring subjects. Yet another illustrative, non-limiting objective is to provide systems for facilitating interaction between users and various third-party entities with regard to physiologic monitoring of the users (e.g., as it relates to managing outbreak of diseases, including epidemics and pandemics).

The above illustrative, non-limiting objectives are wholly or partially met by devices, systems, and methods according to the appended claims in accordance with the present disclosure. Features and aspects are set forth in the appended claims, in the following description, and in the annexed drawings in accordance with the present disclosure.

Before turning to a discussion of an illustrative wearable sensor system configured for monitoring and modeling health data, aspects of a modular physiologic monitoring system that may be utilized to support functionality of the wearable sensor system will be described.

A modular physiologic monitoring system in accordance with the present disclosure is configured to monitor one or more physiologic and/or physical signals, also referred to herein as physiologic parameters, of a subject (e.g., a human subject, a patient, an athlete, a trainer, an animal such as equine, canine, porcine, bovine, etc.). The modular physiologic monitoring system may include one or more patches, each patch adapted for attachment to the body of the subject (e.g., attachable to the skin thereof, reversibly attachable, adhesively attachable, with a disposable interface and a reusable module, etc.). In aspects, the physiologic monitoring system may also include one or more modules configured and dimensioned to mate with corresponding ones of the one or more patches and to interface with the subject therethrough. One or more of the modules may be configured to convey and/or store one or more physiologic and/or physical signals, signals derived therefrom, and/or metrics derived therefrom obtained via the interface with the subject.

Each module may include a power source (e.g., a battery, a rechargeable battery, an energy harvesting transducer, microcircuit, and an energy reservoir, a thermal gradient harvesting transducer, a kinetic energy harvesting transducer, a radio frequency energy harvesting transducer, a fuel cell, a biofuel cell, etc.), signal conditioning circuitry, communication circuitry, one or more sensors, or the like, configured to generate one or more signals (e.g., physiologic and/or physical signals), stimulus, etc.

One or more of the patches may include one or more interconnects configured and dimensioned so as to couple with one or more of the modules, said modules including a complementary interconnect configured and dimensioned to couple with the corresponding patch. The patch may include a bioadhesive interface for attachment to the subject, the module retainable against the subject via interconnection with the patch.

In aspects, the patch may be configured so as to be single use (e.g., disposable). The patch may include a thin, breathable, stretchable laminate. In aspects, the laminate may include a substrate, a bioadhesive, one or more sensing or stimulating elements in accordance with the present disclosure, and one or more interconnects for coupling one or more of the sensing elements with a corresponding module.

In aspects, to retain a high degree of comfort and long term wearability of the patch on a subject, to limit interference with normal body function, to limit interference with joint movement, or the like, the patch may be sufficiently thin and frail, such that it may not substantially retain a predetermined shape while free standing. Such a definition is described in further detail below. The patch may be provided with a temporary stiffening film to retain the shape thereof prior to placement of the patch onto the body of a subject. Once adhered to the subject, the temporary stiffening film may be removed from the patch. While the patch is adhered to the subject, the shape and functionality of the patch may be substantially retained. Upon removal of the patch from the subject, the now freestanding patch is sufficiently frail such that the patch can no longer substantially retain the predetermined shape (e.g., sufficiently frail such that the patch will not survive in a free standing state). In aspects, stretch applied to the patch while removing the patch from the subject may result in snap back once the patch is in a freestanding state that renders such a patch to crumple into a ball and no longer function. Removal of the patch interface from the skin of the subject may result in a permanent loss in shape of the patch interface without tearing of the patch interface. In aspects, the interconnect may be sufficiently frail such that removal of the patch interface from the skin of the subject may result in a permanent loss of shape of the interconnect.

In aspects, the patch may include a film (e.g., a substrate) with sufficiently high tear strength, such that, as the patch is peeled from the skin of a subject, the patch does not tear. In aspects, the ratio between the tear strength of the patch and the peel adhesion strength of the patch to skin (e.g., tear strength:peel adhesion strength) is greater than 8:1, greater than 4:1, greater than 2:1, or the like. Such a configuration may be advantageous so as to ensure the patch may be easily and reliably removed from the subject after use without tearing.

In aspects, the patch may include a bioadhesive with peel tack to mammalian skin of greater than 0.02 Newtons per millimeter (N/mm), greater than 0.1 N/mm, greater than 0.25 N/mm, greater than 0.50 N/mm, greater than 0.75 N/mm, greater than 2 N/mm, or the like. Such peel tack may be approximately determined using an American Society for Testing and Materials (ASTM) standard test, ASTM D3330: Standard test method for peel adhesion of pressure-sensitive tape.

In aspects, the patch may exhibit a tear strength of greater than 0.5 N/mm, greater than 1 N/mm, greater than 2 N/mm, greater than 8 N/mm, or the like. Such tear strength may be approximately determined using an ASTM standard test, ASTM D624: Standard test method for tear strength of conventional vulcanized rubber and thermoplastic elastomers. In aspects, a patch interface in accordance with the present disclosure may have a ratio between the tear strength of the patch and the peel tack of the adhesive to mammalian skin that is greater than 8:1, greater than 4:1, greater than 2:1, or the like.

In aspects, the patch may be provided with a characteristic thickness of less than 50 micrometer (μm), less than 25 μm, less than 12 μm, less than 8 μm, less than 4 μm, or the like. Yet, in aspects, a balance between the thickness, stiffness, and tear strength may be obtained so as to maintain sufficiently high comfort levels for a subject, minimizing skin stresses during use (e.g., minimizing skin stretch related discomfort and extraneous signals as the body moves locally around the patch during use), minimizing impact on skin health, minimizing risk of rucking during use, and minimizing risk of maceration to the skin of a subject, while limiting risk of tearing of the patch during removal from a subject, etc.

In aspects, the properties of the patch may be further altered so as to balance the hydration levels of one or more hydrophilic or amphiphilic components of the patch while attached to a subject. Such adjustment may be advantageous to prevent over hydration or drying of an ionically conducting component of the patch, to manage heat transfer coefficients within one or more elements of the patch, to manage salt retention into a reservoir in accordance with the present disclosure, and/or migration during exercise, to prevent pooling of exudates, sweat, or the like into a fluid measuring sensor incorporated into the patch or associated module, etc. In aspects, the patch or a rate determining component thereof may be configured with a moisture vapor transmission rate of between 200 grams per meter squared per 24 hours (g/m$^2$/24 hrs) and 20,000 g/m$^2$/24 hrs, between 500 g/m$^2$/24 hrs and 12,000 g/m$^2$/24 hrs, between 2,000 g/m$^2$/24 hrs and 8,000 g/m$^2$/24 hrs, or the like.

Such a configuration may be advantageous for providing a comfortable wearable physiologic monitor for a subject, while reducing material waste and/or cost of goods, preventing contamination or disease spread through uncontrolled re-use, and the like.

In aspects, one or more patches and/or modules may be configured for electrically conducting interconnection, inductively coupled interconnection, capacitively coupled interconnection, with each other. In the case of an electrically conducting interconnect, each patch and module interconnect may include complementary electrically conducting connectors, configured and dimensioned so as to mate together upon attachment. In the case of an inductively or capacitively coupled interconnect, the patch and module may include complementary coils or electrodes configured and dimensioned so as to mate together upon attachment.

Each patch or patch-module pair may be configured as a sensing device to monitor one or more local physiologic and/or physical parameters of the attached subject (e.g., local to the site of attachment, etc.), local environment, combinations thereof, or the like, and to relay such information in the form of signals to a host device (e.g., via a wireless connection, via a body area network connection, or the like), one or more patches or modules on the subject, or the like. In some embodiments, the patches are configured to allow sterile contact between a subject and the module, such that the module may be returned, sterilized and reused while the patch may be disposed of. Although various embodiments are described with respect to patches that are single-use or otherwise disposable, it should be appreciated that patches may be configured for multiple uses if desired for a particular implementation. Each patch and/or patch-module pair may also or alternatively be configured as a stimulating device to apply a stimulus to the subject in response to signaling from the host device, the signaling being based on analysis of the physiologic and/or physical parameters of the subject measured by the sensing device(s).

In aspects, the host device may be configured to coordinate information exchange to/from each module and/or patch and to generate one or more physiologic signals, physical signals, environmental signals, kinetic signals, diagnostic signals, alerts, reports, recommendation signals, commands, combinations thereof, or the like for the subject, a user, a network, an electronic health record (EHR), a database (e.g., as part of a data management center, an EHR, a social network, etc.), a processor, combinations thereof, or the like. In aspects, the host device may include features for recharging and/or performing diagnostic tests on one or more of the modules. In aspects, a host device in accordance with the present disclosure may be integrated into a bedside alarm clock, housed in an accessory, within a purse, a backpack, a wallet, or may be included in a mobile computing device, a smartphone, a tablet computer, a pager, a laptop, a local router, a data recorder, a network hub, a server, a secondary mobile computing device, a repeater, a combination thereof, or the like.

In aspects, a system in accordance with the present disclosure may include a plurality of substantially similar modules (e.g., generally interchangeable modules, but with unique identifiers) for coupling with a plurality of patches, each patch, optionally different from the other patches in the system (e.g., potentially including alternative sensors, sensor types, sensor configurations, electrodes, electrode configurations, etc.). Each patch may include an interconnect suitable for attachment to an associated module. Upon attachment of a module to a corresponding patch, the module may validate the type and operation of the patch to which it has been mated. In aspects, the module may then initiate monitoring operations on the subject via the attached patch and communicate with one or more other patches on the subject, a hub, etc. The data collection from each module may be coordinated through one or more modules and/or with a host device in accordance with the present disclosure. The modules may report a timestamp along with the data in order to synchronize data collection across multiple patch-module pairs on the subject, between subjects, etc. Thus, if a module is to be replaced, a hot swappable replacement (e.g., replacement during a monitoring procedure) can be carried out easily by the subject, a caregiver, practitioner, etc. during the monitoring process. Such a configuration may be advantageous for performing redundant, continuous monitoring of a subject, and/or to obtain spatially relevant information from a plurality of locations on the subject during use.

In aspects, the modules and/or patches may include corresponding interconnects for coupling with each other during use. The interconnects may include one or more connectors configured such that the modules and patches may only couple in a single unique orientation with respect to each other. In aspects, the modules may be color coded by function. A temporary stiffening element attached to a patch may include instructions, corresponding color coding, etc. so as to assist a user or subject with simplifying the process of monitoring.

In addition to physiologic monitoring, one or more patches and/or modules may be used to provide a stimulus to the subject, as will be described in further detail below.

According to aspects, there is provided use of a modular physiologic monitoring system in accordance with the present disclosure to monitor a subject, to monitor an electrocardiogram (EKG) of a subject, to perform one or more tasks in accordance with the present disclosure, etc.

According to aspects, there is provided an interface (e.g., a patch in accordance with the present disclosure) for monitoring a physiologic, physical, and/or electrophysiological signal from a subject. The interface or patch may include a substrate, an adhesive coupled to the substrate formulated for attachment to the skin of a subject, and one or more sensors and/or electrodes, each in accordance with the present disclosure coupled to the substrate, arranged, configured, and dimensioned to interface with the subject. The substrate may be formed from an elastic or polymeric material, such that the patch is configured to maintain operation when stretched to more than 25%, more than 50%, or more than 80%.

According to aspects, there is provided an isolating patch for providing a barrier between a handheld monitoring device with a plurality of contact pads and a subject, including a flexible substrate with two surfaces, a patient facing surface and an opposing surface, and an electrically and/or ionically conducting adhesive coupled to at least a portion of the patient facing surface configured so as to electrically and mechanically couple with the subject when placed thereupon, wherein the conducting adhesive is exposed within one or more regions of the opposing surface of the substrate, the regions patterned so as to substantially match the dimensions and layout of the contact pads. In aspects, the conducting adhesive may include an anisotropically conducting adhesive, with the direction of conduction oriented substantially normal to the surfaces of the substrate.

In aspects, the adhesive may be patterned onto the substrate so as to form one or more exposed regions of the substrate, with one or more of the sensors and/or electrodes arranged within the exposed regions. One or more of the electrodes may include an inherently or ionically conducting gel adhesive.

In aspects, one or more of the electrodes may include an electrode feature arranged so as to improve the electrical connection between the electrode and the skin upon placement on a subject. In aspects, the improved electrical connection may be achieved after pressure is applied to the electrode (e.g., after the patch is secured to the subject and then a pressure is applied to the electrode). The electrode feature may include one or more microfibers, barbs, microneedles, or spikes to penetrate into a stratum corneum of the skin. The electrode feature may be configured to penetrate less than 2 mm into the skin, less than 1 mm, less than 0.5 mm, less than 0.2 mm, or the like during engagement therewith. In aspects, a gel adhesive in accordance with the present disclosure located adjacent to the electrode features (e.g., between the features and the skin) may be configured to maintain the improved electrical connection to the skin for more than 1 hour, more than 1 day, or more than 3 days after the electrode contacts the skin or pressure is applied to the electrode.

In aspects, a patch interface in accordance with the present disclosure may include one or more stretchable electrically conducting traces attached to the substrate, arranged so as to couple one or more of the sensors and/or electrodes with one or more of the interconnects.

In aspects, the interconnect may include a plurality of connectors, the connectors physically connected to each other through the substrate. The patch may include an isolating region arranged so as to isolate one or more of the connectors from the skin while the patch is engaged therewith.

According to aspects, there is provided a device (e.g., a module in accordance with the present disclosure) for monitoring a physiologic, physical, and/or electrophysiological signals from a subject. The module may include a housing, a printed circuit board (PCB) including one or more microcircuits, and an interconnect configured for placement of the device onto a subject interface (e.g., a patch in accordance with the present disclosure). The printed circuit board may constitute at least a portion of the housing in some embodiments. The module may include a three-dimensional antenna coupled to the microcircuits (e.g., coupled with a transceiver, transmitter, radio, etc. included within the microcircuits). In aspects, the antenna may be printed onto or embedded into the housing. In aspects, the antenna may be printed on an interior wall of or embedded into the housing, the circuit board providing a ground plane for the antenna. In aspects, the housing may be shaped like a dome, and the antenna may be patterned into a spiraling helix centered within the dome.

In aspects, a module in accordance with the present disclosure may include a sensor coupled with one or more of the microcircuits, the sensor configured to interface with the subject upon attachment of the module to the patch interface. The module may include a sensor and/or microelectronics configured to interface with a sensor included on a corresponding patch interface. In aspects, one or more of the sensors may include an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, a combination thereof, or the like.

In aspects, the module may be hermetically sealed. The module and/or patch interface may include a gasket coupled to the circuit board or the substrate, the gasket formed so as to isolate the region formed by the module interconnect and the patch from a surrounding environment when the module is coupled with the patch.

In aspects, the module interconnect may include an electrically conducting magnetic element, and the patch interface may include one or more ferromagnetic regions coupled to the substrate, the magnetic elements arranged so as to physically and/or electrically couple the module to the patch interface when the magnetic elements are aligned with the ferromagnetic regions. In aspects, the ferromagnetic regions may be formed from stretchable pseudo elastic material and/or may be printed onto the substrate. In aspects, the module and/or the patch interface may include one or more fiducial markings to visually assist with the alignment of the module to the patch during coupling thereof.

According to aspects, there is provided a kit for monitoring a physiologic, physical, and/or electrophysiological signal from a subject, including one or more patches in accordance with the present disclosure, one or more modules in accordance with the present disclosure, a recharging bay in accordance with the present disclosure, and one or more accessories in accordance with the present disclosure. One or more of the accessories may include an adhesive removing agent configured to facilitate substantially pain free removal of one or more of the patches from a subject.

According to aspects, there is provided a service system for managing the collection of physiologic data from a customer, including a customer data management service configured to generate and/or store the customer profile referencing customer preferences, data sets, and/or monitoring sessions, an automated product delivery service configured to provide the customer with one or more monitoring products or supplies in accordance with the present disclosure, and a datacenter configured to store, analyze, and/or manage the data obtained from the customer during one or more monitoring sessions.

In aspects, the service system may include a report generating service configured to generate one or more monitoring reports based upon the data obtained during one or more monitoring sessions, a report generating service coupled to the datacenter configured to generate one or more monitoring reports based upon the data obtained during one or more monitoring sessions, and/or a recurrent billing system configured to bill the customer based upon the number or patches consumed, the data stored, and/or the reports generated throughout the course of one or more monitoring sessions.

According to aspects, there is provided a method for monitoring one or more physiologic and/or electrophysiological signals from a subject, including attaching one or more soft breathable and hypoallergenic devices to one or more sites on the subject, obtaining one or more local physiologic and/or electrophysiological signals from each of the devices, and analyzing the signals obtained from each of the devices to generate a metric, diagnostic, report, and/or additional signals therefrom.

In aspects, the method may include hot swapping one or more of the devices without interrupting the step of obtaining and/or calibrating one or more of the devices while on the subject. In aspects, the step of calibrating may be performed with an additional medical device (e.g., a blood pressure cuff, a thermometer, a pulse oximeter, a cardiopulmonary assessment system, a clinical grade EKG diagnostic system, etc.).

In aspects, the method may include determining the position and/or orientation of one or more of the devices on the subject and/or determining the position and/or orientation from a photograph, a video, or a surveillance video.

In aspects, one or more steps of a method in accordance with the present disclosure may be performed at least in part by a device, patch interface, module, and/or system each in accordance with the present disclosure.

According to aspects, there is provided a system for measuring blood pressure of a subject in an ambulatory setting including an EKG device in accordance with the present disclosure (e.g., a patch/module pair in accordance with the present disclosure configured to measure local electrophysiological signals in adjacent tissues) configured for placement onto a torso of the subject, the EKG device configured to measure an electrocardiographic signal from the torso of the subject so as to produce an EKG signal, one or more pulse devices (e.g., patch/module pairs in accordance with the present disclosure configured to measure local blood flow in adjacent tissues), each in accordance with the present disclosure configured for placement onto one or more sites on one or more extremities of the subject, each of the pulse devices configured to measure a local pulse at the placement site so as to produce one or more pulse signals; and a processor included in or coupled to one or more of the EKG device and the pulse devices, the processor configured to receive the EKG signal, the pulse signals, and/or signals generated therefrom, the processor including an algorithm, the algorithm configured to analyze one or more temporal metrics from the signals in combination with one or more calibration parameters to determine the blood pressure of the subject.

In aspects, the system for monitoring blood pressure of a subject may include a blood pressure cuff configured to produce a calibration signal, the processor configured to generate one or more of the calibration parameters from the calibration signal in combination with the EKG signal, and pulse signals.

In aspects, one or more of the devices may include an orientation sensor, the orientation sensor configured to obtain an orientation signal, the processor configured to receive the orientation signal or a signal generated therefrom and to incorporate the orientation signal into the analysis. Some non-limiting examples of orientation sensors include one or more of an altimeter, a barometer, a tilt sensor, a gyroscope, combinations thereof, or the like.

A system for measuring the effect of an impact on physiologic state of a subject including an electroencephalogram (EEG) device (e.g., a patch/module pair in accordance with the present disclosure configured to measure local electrophysiological signals associated with brain activity in adjacent tissues) in accordance with the present disclosure, configured for placement behind an ear, on the forehead, near a temple, onto the neck of the subject, or the like, the EEG device configured to measure an electroencephalographic signal from the head of the subject so as to produce an EEG signal, and configured to measure one or more kinetic and/or kinematic signals from the head of the subject so as to produce an impact signal, and a processor included in or coupled to the EEG device, the processor configured to receive the EEG signal, the impact signals, and/or signals generated therefrom, the processor including an algorithm, the algorithm configured to analyze the impact signals to determine if the subject has suffered an impact, to separate the signals into pre impact and post impact portions and to compare the pre and post impact portions of the EEG signal, to determine the effect of the impact on the subject.

In aspects, the EEG device may include additional sensors such as a temperature sensor configured to generate a temperature signal from the subject or a signal generated therefrom, the processor configured to receive the temperature signal and to assess a thermal state of the subject therefrom. In aspects, the EEG device may include a hydration sensor configured to generate a fluid level signal from the subject, the processor configured to receive the fluid level signal or a signal generated therefrom and to assess the hydration state of the subject therefrom.

In aspects, the EEG device and/or the processor may include or be coupled to a memory element, the memory element including sufficiently large amounts of space to store the signals for a period of 3 minutes, 10 minutes, 30 minutes, or 1 hour.

In aspects, the system for measuring the effect of an impact on physiologic state of a subject may include an EKG device (e.g., a patch/module pair in accordance with the present disclosure configured to measure local electrophysiological signals in adjacent tissues) in accordance with the present disclosure, the EKG device configured for placement onto the torso or neck of the subject, the EKG device configured to measure an electrophysiological signal pertaining to cardiac function of the subject so as to produce an EKG signal, the processor configured to receive the EKG signal or a signal generated therefrom, the algorithm configured so as to incorporate the EKG signal into the assessment. In aspects, the processor may be configured to extract a heart rate variability (HRV) signal from the EKG signal, and a pre impact and post impact portion of the HRV signal may be compared to determine at least a portion of the effect of the impact.

According to aspects, there is provided a system for assessing a sleep state of a subject including an electromyography (EMG)/electrooculography (EOG) device (e.g., a patch/module pair in accordance with the present disclosure configured to measure local electromyographic and/or electrooculographic signals from adjacent tissues), in accordance with the present disclosure, configured for placement behind an ear, on a forehead, substantially around an eye, near a temple, or onto a neck of the subject, the EMG/EOG device configured to measure one or more electromyographic and/or electrooculographic signals from the head or neck of the subject so as to produce an EMG/EOG signal and a processor included in or coupled to the EMG/EOG device, the processor configured to receive the EMG/EOG signal, and/or signals generated therefrom, the processor including an algorithm, the algorithm configured to analyze an EMG/EOG signal to determine the sleep state of the subject.

In aspects, the EMG/EOG device may include a microphone, the microphone configured to obtain an acoustic signal from the subject, the processor configured to receive the acoustic signal, or a signal generated therefrom, the algorithm configured so as to incorporate the acoustic signal into the assessment.

In aspects, the system may include a sensor for evaluating oxygen saturation (SpO2) at one or more sites on the subject to obtain an oxygen saturation signal from the subject, the processor configured to receive the oxygen saturation signal or a signal generated therefrom, the algorithm configured so as to incorporate the oxygen saturation signal into the assessment.

In aspects, the processor may include a signal analysis function, the signal analysis function configured to analyze the EMG/EOG signals, the acoustic signal, and/or the oxygen saturation signal to determine the sleep state of the subject, identify snoring, identify a sleep apnea event, identify a bruxism event, identify a rapid eye movement (REM) sleep state, identify a sleep walking state, a sleep talking state, a nightmare, or identify a waking event. In aspects, the system may include a feedback mechanism configured to interact with the subject, a user, a doctor, a nurse, a partner, a combination thereof, or the like. The processor may be configured to provide a feedback signal to the feedback mechanism based upon the analysis of the sleep state of the subject. The feedback mechanism may include a transducer, a loudspeaker, a tactile actuator, a visual feedback means, a light source, a buzzer, a combination thereof, or the like to interact with the subject, the user, the doctor, the nurse, the partner, or the like.

A modular physiologic monitoring system, in some embodiments, includes one or more sensing devices, which may be placed or attached to one or more sites on the subject. Alternatively or additionally, one or more sensing devices may be placed "off" the subject, such as one or more sensors (e.g., cameras, acoustic sensors, etc.) that are not physically attached to the subject. The sensing devices are utilized to establish whether or not an event is occurring and to determine one or more characteristics of the event by monitoring and measuring physiologic parameters of the subject. The determination of whether an event has occurred or is occurring may be made by a device that is at least partially external and physically distinct from the one or more sensing devices, such as a host device in wired or wireless communication with the sensing devices as described below with respect to FIG. 1. The modular physiologic monitoring system includes one or more stimulating devices, which again may be any combination of devices that are attached to the subject or placed "off" the subject, to apply a stimulus to the subject in response to a detected event. Various types of stimulus may be applied, including but not limited to stimulating via thermal input, vibration input, mechanical input, a compression or the like with an electrical input, etc.

The sensing devices of a modular physiologic monitoring system, such as patch-module pairs described below with respect to FIG. 1, may be used to monitor one or more physiologic functions or parameters of a subject, as will be described in further detail below. The sensing devices of the modular physiologic monitoring system, or a host device configured to receive data or measurements from the sensing devices, may be utilized to monitor for one or more events (e.g., through analysis of signals measured by the sensing devices, from metrics derived from the signals, etc.). The stimulating devices of the modular physiologic monitoring system may be configured to deliver one or more stimuli (e.g., electrical, vibrational, acoustic, visual, etc.) to the subject. The stimulating devices may receive a signal from one or more of the sensing devices or a host device and provide the stimulation in response to the received signal.

FIG. 1 shows aspects of a modular physiologic monitoring system in accordance with the present disclosure. In FIG. 1, a subject 1 is shown with a number of patches and/or patch-module pairs, each in accordance with the present disclosure attached thereto at sites described below, a host device 145 in accordance with the present disclosure, a feedback/user device 147 in accordance with the present disclosure displaying some data 148 based upon signals obtained from the subject 1, and one or more feedback devices 135, 140, in accordance with the present disclosure configured to convey to the subject 1 one or more aspects of the signals or information gleaned therefrom. In some embodiments, the feedback devices 135, 140 may also or alternatively function as stimulating devices. The host device 145, the user device 147, the patches and/or patch-module pairs, and/or the feedback devices 135, 140 may be configured for wireless communication 146, 149 during a monitoring session.

In aspects, a patch-module pair may be adapted for placement almost anywhere on the body of a subject 1. As shown in FIG. 1, some sites may include attachment to the cranium or forehead 131, the temple, the ear or behind the ear 50, the neck, the front, side, or back of the neck 137, a shoulder 105, a chest region with minimal muscle mass 100, integrated into a piece of ornamental jewelry 55 (may be a host, a hub, a feedback device, etc.), arrangement on the torso 110*a-c*, arrangement on the abdomen 80 for monitoring movement or breathing, below the rib cage 90 for monitoring respiration (generally on the right side of the body to substantially reduce EKG influences on the measurements), on a muscle such as a bicep 85, on a wrist 60 or in combination with a wearable computing device 135 on the wrist (e.g., a smart watch, a fitness band, etc.), on a buttocks 25, on a thigh 75, on a calf muscle 70, on a knee 35 particularly for proprioception based studies and impact studies, on a shin 30 primarily for impact studies, on an ankle 65, over an Achilles tendon 20, on the front or top of the foot 15, on a heel 5, or around the bottom of a foot or toes 10. Other sites for placement of such devices are envisioned. Selection of the monitoring and/or stimulating sites is generally determined based upon the intended application of the patch-module pairs described herein.

Additional placement sites on the abdomen, perineal region 142*a-c*, genitals, urogenital triangle, anal triangle, sacral region, inner thigh 143, or the like may be advantageous in the assessment of autonomic neural function of a subject. Such placements regions may be advantageous for assessment of parasympathetic nervous system (PNS) activity, somatosensory function, assessment of sympathetic nervous system (SNS) functionality, etc.

Placement sites on the wrist 144*a*, hand 144*b* or the like may advantageous for interacting with a subject, such as via performing a stress test, performing a thermal stress test, performing a tactile stress test, monitoring outflow, afferent traffic, efferent traffic, etc.

Placement sites on the nipples, areola, lips, labia, clitoris, penis, the anal sphincter, levator ani muscle, over the ischiocavernous muscle, deep transverse perineal muscle, labium minus, labium majus, one or more nerves near the surface thereof, posterior scrotal nerves, perineal membrane, perineal nerves, superficial transverse perineal nerves, dorsal nerves, inferior rectal nerves, etc. may be advantageous for assessment of autonomic neural ablation procedures, autonomic neural modulation procedures, assessment of the PNS of a subject, assessment of sexual dysfunction of a subject, etc.

Placement sites on the face 141, over ocular muscles, near the eye, over a facial muscle (e.g., a nasalis, temporalis, zygonaticus minor/major, orbicularis oculi, occipitofrontalis), near a nasal canal, over a facial bone (e.g., frontal process, zygomatic bone/surface, zygomaticofacial foreman, malar bone, nasal bone, frontal bone, maxilla, temporal bone, occipital bone, etc.), may be advantageous to assess ocular function, salivary function, sinus function, interaction with the lips, interaction with one or more nerves of the PNS (e.g., interacting with the vagus nerve within, on, and/or near the ear of the subject), etc.

In aspects, a system in accordance with the present disclosure may be configured to monitor one or more physiologic parameters of the subject 1 before, during, and/or after one or more of a stress test, consumption of a medication, exercise, a rehabilitation session, a massage, driving, a movie, an amusement park ride, sleep, intercourse, a surgical, interventional, or non-invasive procedure, a neural remodeling procedure, a denervation procedure, a sympathectomy, a neural ablation, a peripheral nerve ablation, a radio-surgical procedure, an interventional procedure, a cardiac repair, administration of an analgesic, a combination thereof, or the like. In aspects, a system in accordance with the present disclosure may be configured to monitor one or more aspects of an autonomic neural response to a procedure, confirm completion of the procedure, select candidates for a procedure, follow up on a subject after having received a procedure, assess the durability of a procedure, or the like (e.g., such as wherein the procedure is a renal denervation procedure, a carotid body denervation procedure, a hepatic artery denervation procedure, a LUTs treatment, a bladder denervation procedure, a urethral treatment, a prostate ablation, a prostate nerve denervation procedure, a cancer treatment, a pain block, a neural block, a bronchial denervation procedure, a carotid sinus neuromodulation procedure, implantation of a neuromodulation device, tuning of a neuromodulation device, etc.).

Additional details regarding modular physiologic monitoring systems, kits and methods are further described in PCT application serial no. PCT/US2014/041339, published as WO 2014/197822 and titled "Modular Physiologic Monitoring Systems, Kits, and Methods," PCT application serial no. PCT/US2015/043123, published as WO 2016/019250 and titled "Modular Physiologic Monitoring Systems, Kits, and Methods," and PCT application serial no. PCT/US2017/030186, published as WO 2017/190049 and titled "Monitoring and Management of Physiologic Parameters of a Subject," the disclosures of which are incorporated by reference herein in their entirety.

In some embodiments, modular physiologic monitoring systems may include sensing and stimulating devices that are physically distinct, such as sensing and stimulating devices that are physically attached to a subject at varying locations. For example, the sensing and stimulating devices may include different ones of the patch-module pairs described above with respect to FIG. 1. In other embodiments, one or more devices may provide both monitoring and stimulating functionality. For example, one or more of the patch-module pairs described above with respect to FIG. 1 may be configured to function as both a sensing device and a stimulating device. It is to be appreciated, however, that embodiments are not limited solely for use with the patch-module pairs of FIG. 1 as sensing and stimulating devices. Various other types of sensing and stimulating devices may be utilized, including but not limited to sensors that are "off-body" with respect to subject 1.

The sensing and/or stimulating devices of a modular physiologic monitoring system may be configured for radio frequency (RF) or other wireless and/or wired connection with one another and/or a host device. Such RF or other connection may be used to transmit or receive feedback parameters or other signaling between the sensing and stimulating devices. The feedback, for example, may be provided based on measurements of physiologic parameters that are obtained using the sensing devices to determine when events related to cardiac output are occurring. Various thresholds for stimulation that are applied by the stimulating devices may, in some embodiments, be determined based on such feedback. Thresholds may relate to the amplitude or frequency of electric or other stimulation. Thresholds may also be related to whether to initiate stimulation by the stimulating devices based on the feedback.

During and/or after stimulus is applied with the stimulating devices, the sensing devices may monitor the physiologic response of the subject. If stimulation is successful in achieving a desired response, the stimulation may be discontinued. Otherwise, the type, timing, etc. of stimulation may be adjusted.

In some embodiments, a user of the modular physiologic monitoring system may set preferences for the stimulus type, level, and/or otherwise personalize the sensation during a setup period or at any point during use of the modular physiologic monitoring system. The user of the modular physiologic monitoring system may be the subject being monitored and stimulated by the sensing devices and stimulating devices, or a doctor, nurse, physical therapist, medical assistant, caregiver, etc. of the subject being monitored and stimulated. The user may also have the option to disconnect or shut down the modular physiologic monitoring system at any time, such as via operation of a switch, pressure sensation, voice operated instruction, etc.

Stimulus or feedback which may be provided via one or more stimulating devices in a modular physiologic monitoring system may be in various forms, including physical stimulus (e.g., electrical, thermal, vibrational, pressure, stroking, a combination thereof, or the like), optical stimulus, acoustic stimulus, etc.

Physical stimulus may be provided in the form of negative feedback, such as in a brief electric shock or impulse as described above. Data or knowledge from waveforms applied in conducted electrical weapons (CEWs), such as in electroshock devices, may be utilized to avoid painful stimulus. Physical stimulus may also be provided in the form of positive feedback, such as in evoking pleasurable sensations by combining non-painful electrical stimulus with pleasant sounds, music, lighting, smells, etc. Physical stimulus is not limited solely to electrical shock or impulses. In other embodiments, physical stimulus may be provided by adjusting temperature or other stimuli, such as in providing a burst of cool or warm air, a burst of mist, vibration, tension, stretch, pressure, etc.

Feedback provided via physical stimulus as well as other stimulus described herein may be synchronized with, initiated by or otherwise coordinated or controlled in conjunction with one or more monitoring devices (e.g., a host device, one or more sensing devices, etc.). The monitoring devices may be connected to the stimulating devices physically (e.g., via one or more wires or other connectors), wirelessly (e.g., via radio or other wireless communication), etc. Physical stimulus may be applied to various regions of a subject, including but not limited to the wrist, soles of the feet, palms of the hands, nipples, forehead, ear, mastoid region, the skin of the subject, etc.

Optical stimulus may be provided via one or more stimulating devices. The optical stimulus may be positive or negative (e.g., by providing pleasant or unpleasant lighting or other visuals). Acoustic stimulus similarly may be provided via one or more stimulating devices, as positive or negative feedback (e.g., by providing pleasant or unpleasant sounds). Acoustic stimulus may take the form of spoken words, music, etc. Acoustic stimulus, in some embodiments may be provided via smart speakers or other electronic devices such as Amazon Echo®, Google Home®, Apple Home Pod®, etc. The stimulus itself may be provided so as to elicit a particular psychophysical or psychoacoustic effect in the subject, such as directing the subject to stop an action, to restart an action (such as breathing), to adjust an action (such as a timing between a step and a respiratory action, between a muscle contraction and a leg position, etc.).

As described above, the modular physiologic monitoring system may operate in a therapeutic mode, in that stimulation is provided when one or more cardiac parameters of a subject indicate some event (e.g., actual, imminent or predicted failure or worsening). The modular physiologic monitoring system, however, may also operate as or provide a type of cardiac "pacemaker" in other embodiments. In such embodiments, the modular physiologic monitoring system has the potential to reduce the frequency of cardiac events or to possibly avoid certain cardiac events altogether. A modular physiologic monitoring system may provide functionality for timing and synchronizing periodic compression and relaxation of microvascular blood vessel networks with cardiac output. Such techniques may be utilized to respond to a type of failure event as indicated above. Alternatively or additionally, such techniques may be provided substantially continuously so as to improve overall cardiac performance (e.g., blood flow) with the same or less cardiac work.

In some embodiments, a modular physiologic monitoring system may be configured to provide multi-modal stimuli to a subject. Multi-modal approaches use one or more forms of stimulation (e.g., thermal and electrical, mechanical and electrical, etc.) in order to mimic another stimulus to trick local nerves into responding in the same manner to the mimicked stimulus. In addition, in some embodiments, multi-modal stimulus or input may be used to enhance a particular stimulus. For example, adding a mimicked electrical stimulus may enhance the effect of a thermal stimulus.

Modular physiologic monitoring systems may use pulses across space and time (e.g., frequency, pulse trains, relative amplitudes, etc.) to mimic vibration, comfort or discomfort, mild or greater pain, wet sensation, heat/cold, training neuroplasticity, taste (e.g., using a stimulating device placed in the mouth or on the tongue of a subject to mimic sour, sweet, salt, bitter or umami flavor), tension or stretching, sound or acoustics, sharp or dull pressure, light polarization (e.g., linear versus polar, the "Haidinger Brush"), light color or brightness, etc.

Stimulus amplification may also be provided by one or more modular physiologic monitoring systems using multimodal input. Stimulus amplification represents a hybrid approach, wherein a first type of stimulus may be applied and a second, different type of stimulus may be provided to enhance the effect of the first type of stimulus. As an example, a first stimulus may be provided via a heating element, where the heating element is augmented by nearby electrodes or other stimulating devices that amplify and augment the heating stimulus using electrical mimicry in a pacing pattern. Electrical stimulus may also be used as a supplement or to mimic various other types of stimulus, including but not limited to vibration, heat, cold, etc. Different, possibly unique, stimulation patterns may be applied to the subject, with the central nervous system and peripheral nervous system interpreting such different or unique stimulation patterns as different stimulus modalities.

Another example of stimulus augmentation is sensing a "real" stimulus, measuring the stimulus, and constructing a proportional response by mimicry such as using electric pulsation. The real stimulus, such as sensing heat or cold from a Peltier device, may be measured by electrical-thermal conversion. This real stimulus may then be amplified using virtual mimicry, which may provide energy savings and the possibility of modifying virtual stimulus to modify the perception of the real stimulus.

In some embodiments, the stimulating devices in a modular physiologic monitoring system include an electrode array that attaches (e.g., via an adhesive or which is otherwise held in place) to a preferred body part. One or more of the stimulating devices may include a multiplicity of both sensing and stimulation electrodes, including different types of sensing and/or stimulation electrodes. The sensing electrodes on the stimulation devices, in some embodiments, may be distinct from the sensing devices in the modular physiologic monitoring system in that the sensing devices in the modular physiologic monitoring system may be used to measure physiologic parameters of the subject while the sensing electrodes on the stimulation devices in the modular physiologic monitoring system may be utilized to monitor the application of a stimulus to the subject.

A test stimulus may be initiated in a pattern in the electrode array, starting from application via one or a few of the stimulation electrodes and increasing in number over time to cover an entire or larger portion of the electrode array. The test stimulus may be used to determine the subject's response to the applied stimulation. Sensing electrodes on the stimulation devices may be used to monitor the application of the stimulus. The electrode array may also be used to record a desired output (e.g., physiologic parameters related to cardiac output). As such, one or more of the electrodes in the array may be configured so as to measure the local evoked response associated with the stimulus itself. Such an approach may be advantageous to confirm capture of the target nerves during use. By monitoring the neural response to the stimulus, the stimulus parameters including amplitude, duration, pulse number, etc. may be adjusted while ensuring that the target nerves are enlisted by the stimulus in use.

The test stimulus may migrate or be applied in a pattern to different electrodes at different locations in the electrode array. The response to the stimulus may be recorded or otherwise measured using the sensing devices in the modular physiologic monitoring system and/or one or more of the sensing electrodes of the stimulating devices in the modular physiologic monitoring system. The response to the test stimulus may be recorded or analyzed to determine an optimal sensing or application site for the stimulus to achieve a desired effect or response in the subject. Thus, the test stimulus may be utilized to find an optimal sensing (e.g., dermatome driver) location. This allows for powerful localization for optimal pacing or other application of stimulus, which may be individualized for different subjects.

A stimulating device applied to the subject via an adhesive (e.g., an adhesively applied stimulating device) may be in the form of a disposable or reusable unit, such as a patch and or patch-module or patch/hub pair as described above with respect to FIG. 1. An adhesively applied stimulating device, in some embodiments, includes a disposable interface configured so as to be thin, stretchable, able to conform to the skin of the subject, and sufficiently soft for comfortable wear. The disposable interface may be built from very thin, stretchable and/or breathable materials, such that the subject generally does not feel the device on his or her body.

The adhesively applied stimulating device also includes a means for interfacing with the subject through an adhesive interface and/or a window in the adhesive interface. Such means may include a plurality of electrodes that are coupled with a reusable component of the adhesively applied stimulating device and that are coupled to the body of the subject through the adhesive interface. The means may also or alternatively include: a vibrating actuator to provide vibration normal to and/or transverse to the surface of the skin on which the adhesively applied stimulating device is attached to the subject; a thermal device such as a Peltier device, a heating element, a cooling element, an RF heating circuit, an ultrasound source, etc.; a means for stroking the skin such as a shape memory actuator, an electroactive polymer actuator, etc.; a means for applying pressure to the skin such as a pneumatic actuator, a hydraulic actuator, etc.

Actuation means of the adhesively applied stimulating device may be applied over a small region of the applied area of the subject, such that the adhesive interface provides the biasing force necessary to counter the actuation of the actuation means against the skin of the subject.

Adhesively applied stimulating devices may be provided as two components: a disposable body interface and a reusable component. The disposable body interface may be applied so as to conform to the desired anatomy of the subject and wrap around the body such that the reusable component may interface with the disposable component in a region that is open and free from a natural interface between the subject and another surface.

An adhesively applied stimulating device may also be a single component, rather than a two component or other multi-component arrangement. Such a device implemented as a single component may include an adhesive interface to the subject including two or more electrodes that are applied to the subject. Adhesively applied stimulating devices embodied as a single component provide potential advantages such as easier application to the body of the subject but may come at a disadvantage with regards to one or more of breathability, conformity, access to challenging interfaces, etc. relative to two component or multi-component arrangements.

A non-contacting stimulating device may be, for example, an audio and/or visual system, a heating or cooling system, etc. Smart speakers and smart televisions or other displays are examples of audio and/or visual non-contacting stimulation devices. A smart speaker, for example, may be used to provide audible stimulus to the subject in the form of an alert, a suggestion, a command, music, other sounds, etc. Other examples of non-contacting stimulating devices include means for controlling temperature such as fans, air conditioners, heaters, etc.

One or more stimulating devices may also be incorporated in other systems, such as stimulating devices integrated into a bed, chair, operating table, exercise equipment, etc. that a subject interfaces with. A bed, for example, may include one or more pneumatic actuators, vibration actuators, shakers, or the like to provide a stimulus to the subject in response to a command, feedback signal or control signal generated based on measurement of one or more physiologic parameters of the subject utilizing one or more sensing devices.

Although the disclosure has discussed devices attached to the body for monitoring aspects of the subject's disorder and/or physiologic information, as well as providing a stimulus, therapeutic stimulus, etc., alternative devices may be considered. Non-contacting devices may be used to obtain movement information, audible information, skin blood flow changes (e.g., such as by monitoring subtle skin tone changes which correlate with heart rate), respiration (e.g., audible sounds and movement related to respiration), and the like. Such non-contacting devices may be used in place of or to supplement an on-body system for the monitoring of certain conditions, for applying stimulus, etc. Information captured by non-contacting devices may, on its own or in combination with information gathered from sensing devices on the body, be used to direct the application of stimulus to the subject, via one or more stimulating devices on the body and/or via one or more non-contacting stimulating devices.

In some embodiments, aspects of monitoring the subject utilizing sensing devices in the modular physiologic monitoring system may utilize sensing devices that are affixed to or embodied within one or more contact surfaces, such as surfaces on a piece of furniture on which a subject is positioned (e.g., the surface of a bed, a recliner, a car seat, etc.). The surface may be equipped with one or more sensors to monitor the movement, respiration, HR, etc. of the subject. To achieve reliable recordings, it is advantageous to have such surfaces be well positioned against the subject. It is also advantageous to build such surfaces to take into account the comfort level of the subject to keep the subject from feeling the sensing surfaces and to maintain use of the sensing surface over time.

Stimulating devices, as discussed above, may take the form of audio, visual or audiovisual systems or devices in the sleep space of the subject. Examples of such stimulating devices include smart speakers. Such stimulating devices provide a means for instructing a subject to alter the sleep state thereof. The input or stimulus may take the form of a message, suggestion, command, audible alert, musical input, change in musical input, a visual alert, one or more lights, a combination of light and sound, etc. Examples of such non-contacting stimulating devices include systems such as Amazon Echo®, Google Home®, Apple Home Pod®, and the like.

Figure 2A:
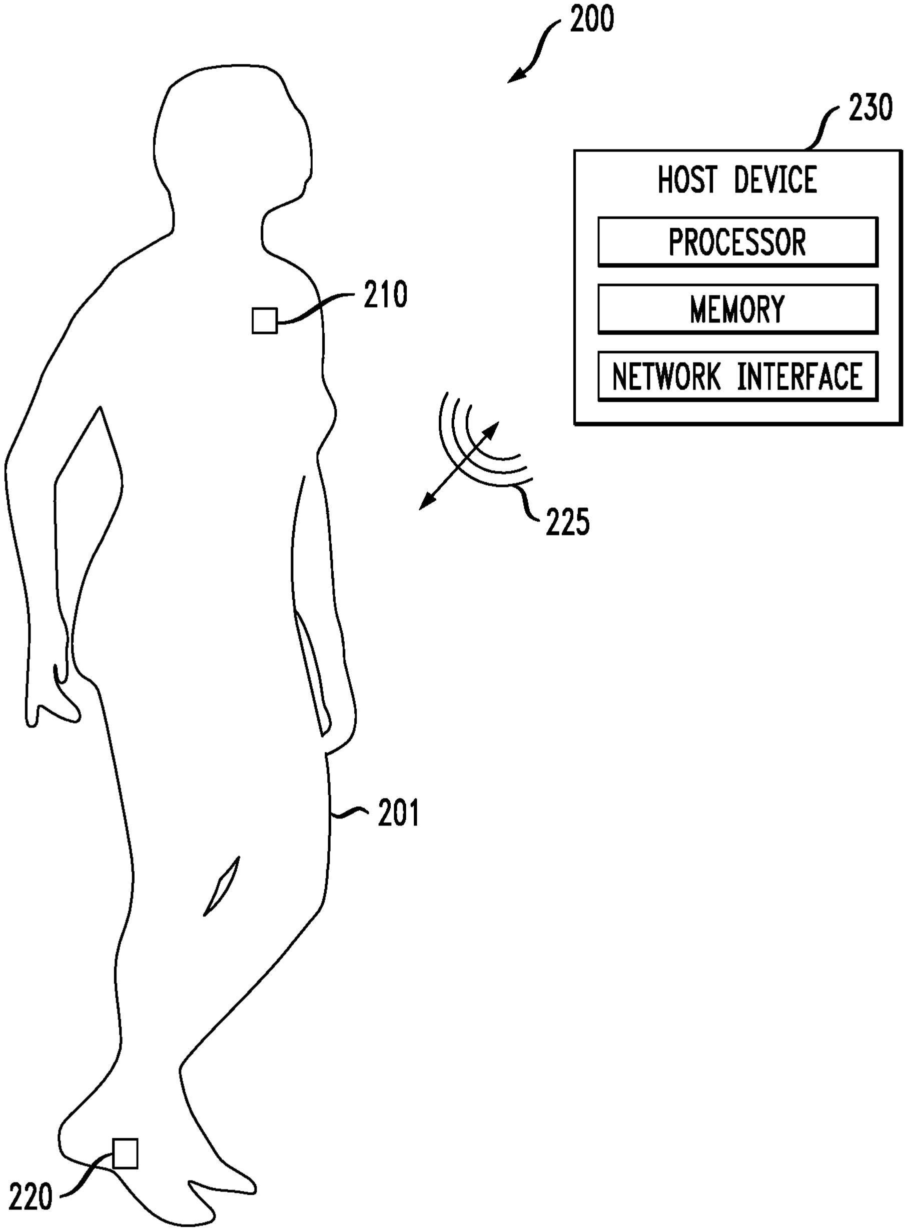
FIGS. 2A-2C illustrate a modular physiologic monitoring system, according to an embodiment of the invention.
Figure 2B:
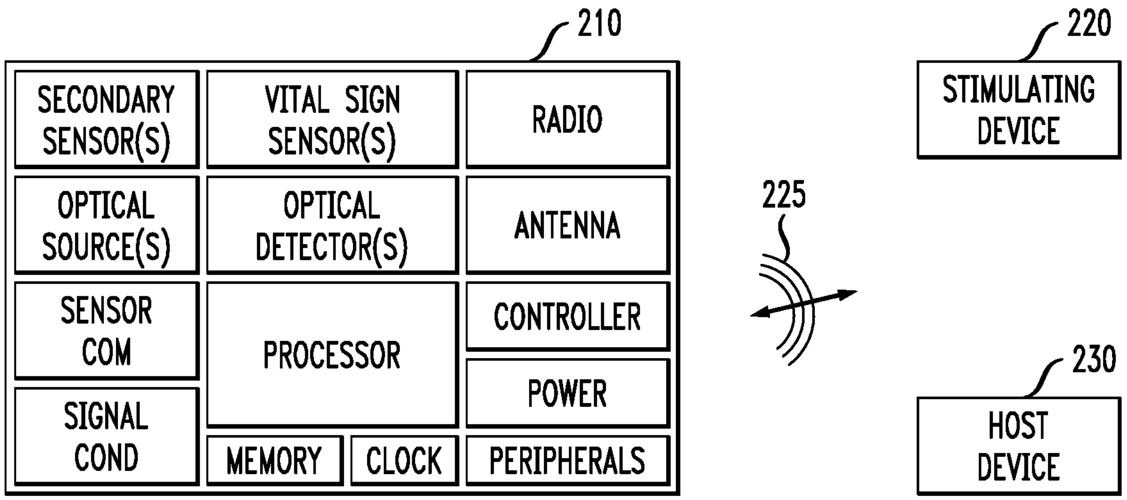
Figure 2C:
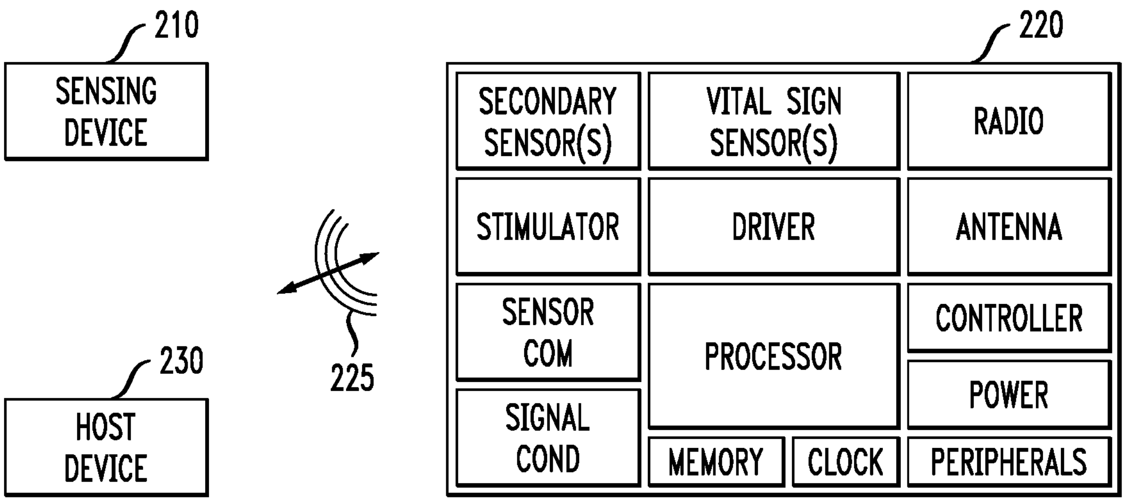

FIGS. 2A-2C show a modular physiologic monitoring system 200. The modular physiologic monitoring system 200 includes a sensing device 210 and a stimulating device 220 attached to a subject 201 that are in wireless communication 225 with a host device 230. The host device 230 includes a processor, a memory and a network interface.

The processor may comprise a microprocessor, a microcontroller, an application-specific integrated circuit (ASIC), a field-programmable gate array (FPGA) or other type of processing circuitry, as well as portions or combinations of such circuitry elements.

The memory may comprise random access memory (RAM), read-only memory (ROM) or other types of memory, in any combination. The memory and other memories disclosed herein may be viewed as examples of what are more generally referred to as "processor-readable storage media" storing executable computer program code or other types of software programs. Articles of manufacture comprising such processor-readable storage media are considered embodiments of the invention. A given such article of manufacture may comprise, for example, a storage device such as a storage disk, a storage array or an integrated circuit containing memory. The processor may load the computer program code from the memory and execute the code to provide the functionalities of the host device 230.

The network interface provides circuitry enabling wireless communication between the host device 230, the sensing device 210 and the stimulating device 220.

FIG. 2A illustrates a modular physiologic monitoring system 200 that includes only a single instance of the sensing device 210 and the stimulating device 220 for clarity. It is to be appreciated, however, that modular physiologic monitoring system 200 may include multiple sensing devices and/or multiple stimulating devices. In addition, although FIG. 2A illustrates a modular physiologic monitoring system 200 in which the sensing device 210 and the stimulating device 220 are attached to the subject 201, embodiments are not limited to such arrangements. As described above, one or more sensing and/or stimulating devices may be part of contacting surfaces or non-contacting devices. In addition, the placement of sensing device 210 and stimulating device 220 on the subject 201 may vary as described above. Also, the host device 230 may be worn by the subject 201, such as being incorporated into a smartwatch or other wearable computing device. The functionality provided by host device 230 may also be provided, in some embodiments, by one or more of the sensing device 210 and the stimulating device 220. In some embodiments, as will be described in further detail below, the functionality of the host device 230 may be provided at least in part using cloud computing resources.

FIG. 2B shows a schematic diagram of aspects of the sensing device 210 in modular physiologic monitoring system 200. The sensing device 210 includes one or more of a processor, a memory device, a controller, a power supply, a power management and/or energy harvesting circuit, one or more peripherals, a clock, an antenna, a radio, a signal conditioning circuit, optical source(s), optical detector(s), a sensor communication circuit, vital sign sensor(s), and secondary sensor(s). The sensing device 210 is configured for wireless communication 225 with the stimulating device 220 and host device 230.

FIG. 2C shows a schematic diagram of aspects of the stimulating device 220 in modular physiologic monitoring system 200. The stimulating device 220 includes one or more of a processor, a memory device, a controller, a power supply, a power management and/or energy harvesting circuit, one or more peripherals, a clock, an antenna, a radio, a signal conditioning circuit, a driver, a stimulator, vital sign sensor(s), a sensor communication circuit, and secondary sensor(s). The stimulating device 220 is configured for wireless communication 225 with the sensing device 210 and host device 230.

Communication of data from the sensing devices and/or stimulating devices (e.g., patches and/or patch-module pairs) may be performed via a local personal communication device (PCD). Such communication in some embodiments takes place in two parts: (1) local communication between a patch and/or patch-module pair (e.g., via a hub or module of a patch-module pair) and the PCD; and (2) remote communication from the PCD to a back-end server, which may be part of a cloud computing platform and implemented using one or more virtual machines (VMs) and/or software containers. The PCD and back-end server may collectively provide functionality of the host device as described elsewhere herein.

Illustrative embodiments provide systems, devices and methods for monitoring and modeling health data (e.g., global health data associated with outbreak of a disease).

Figure 3A:
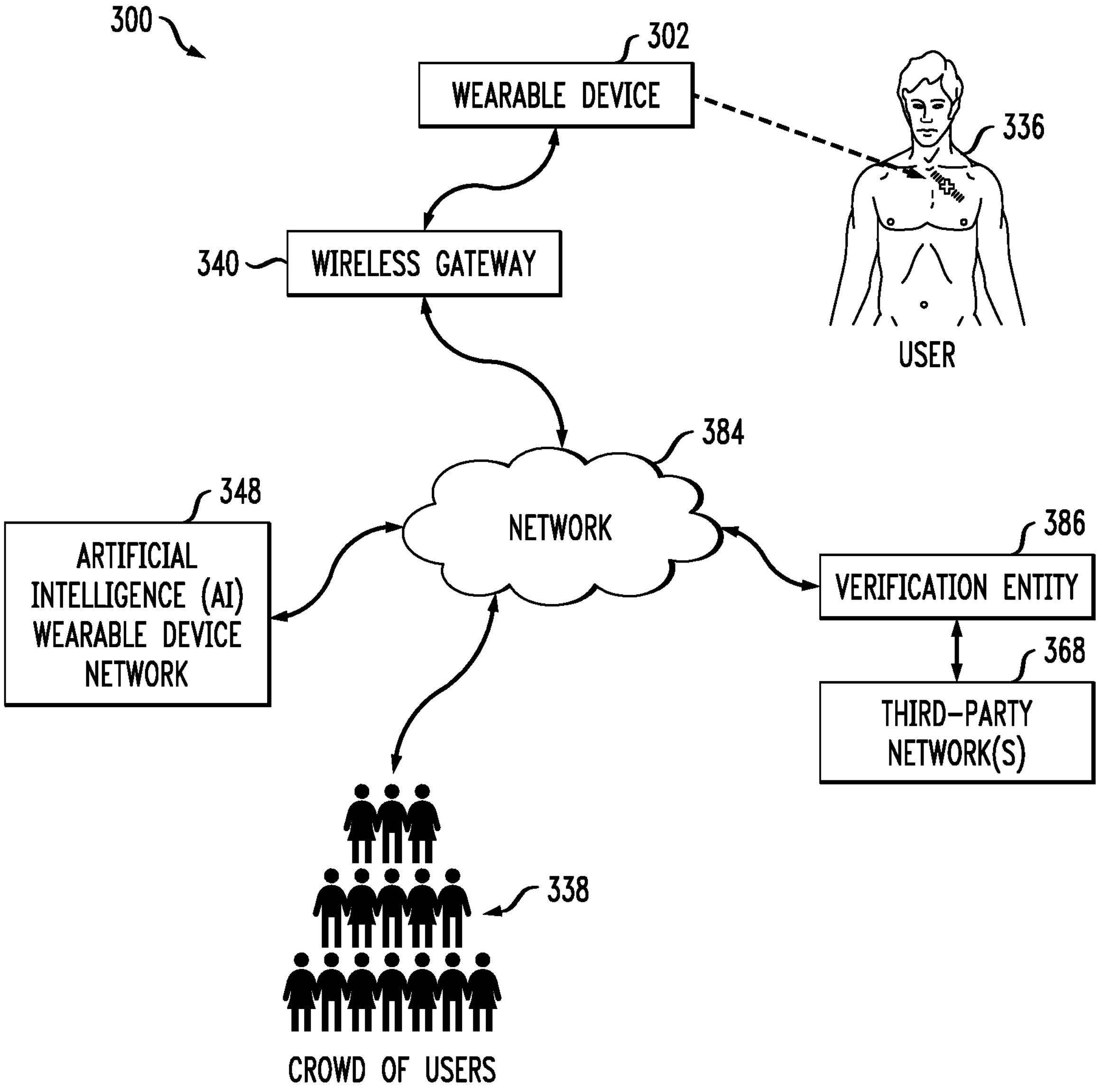
FIGS. 3A-3E illustrate a wearable sensor system configured for monitoring and modeling health data, according to an embodiment of the invention.

FIGS. 3A-3E show a wearable sensor system 300 configured for monitoring physiologic and location data for a plurality of users and for analyzing such data for use in health monitoring. The wearable sensor system 300 can thus be used for managing outbreaks of a disease, including outbreaks associated with epidemics and global pandemics. The wearable sensor system 300 provides the capability for assessing the condition of the human body of a plurality of users. As shown in FIG. 3A, the wearable sensor system 300 includes a wearable device 302 that is affixed to user 336. Data collected from the user 336 via the wearable device 302 is communicated using a wireless gateway 340 to an artificial intelligence (AI) wearable device network 348 over or via network 384. The network 384 may comprise a physical connection (wired or wireless), the Internet, a cloud communication network, etc. Examples of wireless communication networks that may be utilized include networks that utilize Visible Light Communication (VLC), Worldwide Interoperability for Microwave Access (WiMAX), Long Term Evolution (LTE), Wireless Local Area Network (WLAN), Infrared (IR) communication, Public Switched Telephone Network (PSTN), Radio waves, and other communication techniques known in the art. Also coupled to the network 384 is a crowd of users 338 and a verification entity 386 coupled to a set of third-party networks 368. Detailed views of the wearable device 302, wireless gateway 340, AI wearable device network 348 and third-party networks 368 are shown in FIGS. 3B-3E, respectively.

In some embodiments, the wearable device 302 is implemented using one or more patch-module pairs as described above with respect to FIGS. 1 and 2A-2C. The patch-module pairs described above with respect to FIGS. 1 and 2A-2C, however, are just one example of wearable technology that may be used to provide the wearable device 302. Various other types of wearable technology may be used to provide the wearable device in other embodiments, including but not limited to wearables, fashion technology, tech togs and other types of fashion electronics that include “smart” electronic devices (e.g., electronic devices with micro-controllers) that can be incorporated into clothing or worn on the body as implants or accessories. Wearable devices such as activity trackers are examples of Internet of Things (IoT) devices, and such “things” include electronics, software, sensors and connectivity units that are effectors enabling objects to exchange data (including data quality) through the Internet with a manufacturer, operator and/or other connected devices without requiring human intervention. Wearable technology has a variety of applications, which grows as the field itself expands. Wearable technology appears prominently in consumer electronics with the popularization of smartwatches and activity trackers. Apart from commercial uses, wearable technology is being incorporated into navigation systems, advanced textiles, and health care.

In some embodiments, the wearable device 302 is capable of detecting and collecting medical data (e.g., body temperature, respiration, heart rate, etc.) from the wearer (e.g., user 336). The wearable device 302 can remotely collect and transmit real-time physiological data to health care providers and other caretakers responsible for ensuring their communities stay healthy. The wearable sensor system 300, in some embodiments, is user-friendly, hypoallergenic, unobtrusive, and cost-effective. In service of enabling remote evaluation of individual health indicators, the wearable sensor system 300 is configured to transmit data directly into existing health informatics and health care management systems from the comfort of patients' homes. The wearable device 302 is designed to monitor the cardiopulmonary state of a subject (e.g., user 336) over time in home or in clinical settings. Onboard sensors of the wearable device 302 can quantitatively detect and track severity of a variety of disease symptoms including fever, coughing, sneezing, vomiting, infirmity, tremor, and dizziness, as well as signs of decreased physical performance and changes in respiratory rate/depth. The wearable device 302 may also have the capability to monitor blood oxygenation.

In some embodiments, the wearable device 302 collects physiologic monitoring data from the subject user 336 utilizing a combination of a disposable sampling unit 312 and a reusable sensing unit 314. The patch-module pairs described above with respect to FIGS. 1 and 2A-2C are an example implementation of the disposable sampling unit 312 and reusable sensing unit 314. The disposable sampling unit 312 may be formed from a softer-than-skin patch. The wearable device 302 formed from the combination of the disposable sampling unit 312 and reusable sensing unit 314 is illustratively robust enough for military use, yet extremely thin and lightweight. For example, the disposable sampling unit 312 and reusable sensing unit 314 may collectively weigh less than 0.1 ounce, about the same as a U.S. penny. The wearable device 302 may be adapted for placement almost anywhere on the body of the user 336, such as the various placement sites shown in FIG. 1 and described above.

Figure 3B:
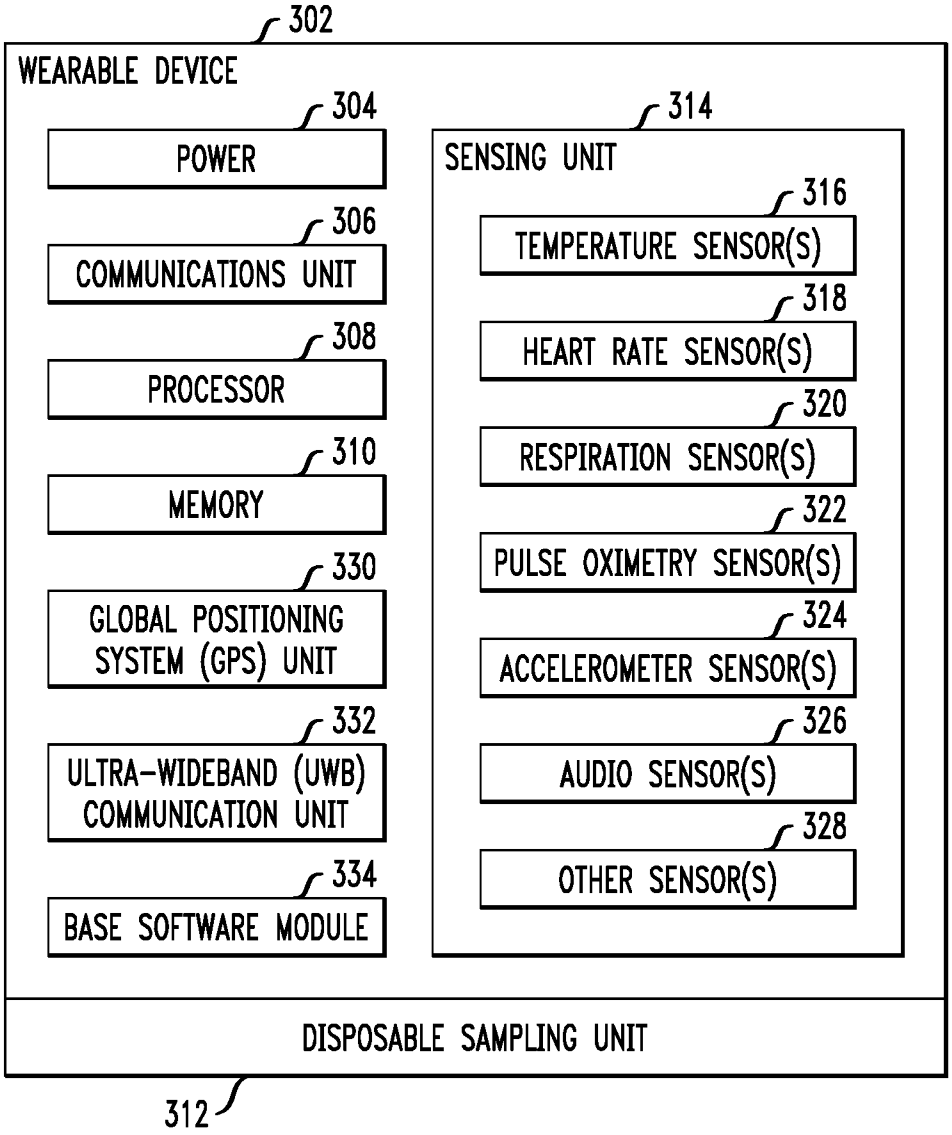

In addition to the disposable sampling unit 312 and reusable sensing unit 314, the wearable device 302 may include a number of other components as illustrated in FIG. 3B. Such components include a power source 304, a communications unit 306, a processor 308, a memory 310, a GPS unit 330, an UWB communication unit 332, and a base software module 334.

The power source or component 304 of the wearable device 302, in some embodiments, includes one or more modules with each module including a power source (e.g., a battery, a rechargeable battery, an energy harvesting transducer, a microcircuit, an energy reservoir, a thermal gradient harvesting transducer, a kinetic energy harvesting transducer, a radio frequency energy harvesting transducer, a fuel cell, a biofuel cell, combinations thereof, etc.).

The communications unit 306 of the wearable device 302 may be embodied as communication circuitry, or any communication hardware that is capable of transmitting an analog or digital signal over one or more wired or wireless interfaces. In some embodiments, the communications unit 306 includes transceivers or other hardware for communications protocols such as Near Field Communication (NFC), WiFi, Bluetooth, infrared (IR), modem, cellular, ZigBee, a Body Area Network (BAN), and other types of wireless communications. The communications unit 306 may also or alternatively include wired communication hardware, such as one or more universal serial bus (USB) interfaces.

The processor 308 of the wearable device 302 is configured to decode and execute any instructions received from one or more other electronic devices and/or servers. The processor 308 may include any combination of one or more general-purpose processors (e.g., Intel® or Advanced Micro Devices (AMD)® microprocessors), one or more special-purpose processors (e.g., digital signal processors or Xilink® system on chip (SOC), field programmable gate array (FPGA) processors, application-specific integrated circuits (ASICs), etc.), etc. The processor 308 is configured in some embodiments to execute one or more computer-readable program instructions, such as program instructions to carry out any of the functions described herein including but not limited to those of the base software module 334 described below. The processor 308 is illustratively coupled to the memory 310, with the memory 310 storing such computer-readable program instructions.

The memory 310 may include, but is not limited to, fixed hard disk drives, magnetic tape, floppy diskettes, optical disks, compact disc read-only memories (CD-ROMs), magneto-optical disks, semiconductor memories such as read-only memory (ROM), random-access memory (RAM), programmable ROM (PROM), erasable PROM (EPROM), electrically erasable PROM (EEPROM), flash memory, magnetic or optical cards, or other type of media/machine-readable medium suitable for storing electronic instructions. The memory 310 may comprise modules implemented as one or more programs. In some embodiments, a non-transitory processor-readable storage medium has stored therein program code of one or more software programs, wherein the program code when executed by at least one processing device (e.g., the processor 308) causes said at least one processing device to perform one or more aspects of the methods, algorithms and process flows described herein.

The processor 308 and memory 310 are an example of a processing device or controller. The controller may comprise a central processing unit (CPU) for carrying out instructions of one or more computer programs for performing arithmetic, logic, control and input/output (I/O) operations specified by the instructions (e.g., as specified by the base software module 334 as described in further detail below). Such computer programs may be stored in the memory 310. The memory 310 provides electronic circuitry configured to temporarily store data that is utilized by the processor 308. In some embodiments, the memory 310 further provides persistent storage for storing data utilized by the processor 308. Although not explicitly shown, other components of the wearable sensor system 300 (e.g., the wireless gateway 340, the AI wearable device network 348, one or more of the third-party networks 368, the verification entity 386, etc.) may also include one or more processors coupled to one or more memories providing processing devices implementing the functionality of such components.

As noted above, the wearable device 302 illustratively includes the disposable sampling unit 312 which may be embodied as a physical interface to the skin of the user 336. Patches as described elsewhere herein are examples of a disposable sampling unit 312. Such patches are adapted for attachment to a human or animal body (e.g., attachable to the skin thereof, reversibly attachable, adhesively attachable, with a disposable interface that couples to a reusable module, etc.). In some embodiments, the disposable sampling unit 312 is part of a system that is capable of modular design, such that various wearable devices or portions thereof (e.g., reusable sensing unit 314) are compatible with various disposable sampling units with differing capabilities. In some embodiments, the patch or more generally the disposable sampling unit 312 allows sterile contact between the user 336 and other portions of the wearable device 302 such as the reusable sensing unit 314. In such embodiments, the other portions of the wearable device 302 (e.g., which may be embodied as a module as described above with respect to FIGS. 1 and 2A-2C) may be returned, sterilized and reused (e.g., by the same user 336 or another user) while the patch or disposable sampling unit 312 is disposed of In some embodiments, the patch or other disposable sampling unit 312 is suitable for wearing over a duration of time in which the user 336 is undergoing physiological monitoring for symptoms of a disease associated with a global pandemic. In such embodiments, the patch or disposable sampling unit 312 may be disposed of after the monitoring duration has ended, in association with an incubation period of the disease.

The reusable sensing unit 314 includes various sensors, such as one or more temperature sensors 316, one or more heart rate sensors 318, one or more respiration sensors 320, one or more pulse oximetry sensors 322, one or more accelerometer sensors 324, one or more audio sensors 326, and one or more other sensors 328. One or more of the sensors 316-328 may be embodied as electric features, capacitive elements, resistive elements, touch sensitive components, analyte sensing elements, printed electrochemical sensors, light sensitive sensing elements, electrodes (e.g., including but not limited to needle electrodes, ionically conducting electrodes, reference electrodes, etc.), electrical traces and/or interconnects, stretch sensing elements, contact interfaces, conduits, microfluidic channels, antennas, stretch resistant features, stretch vulnerable features (e.g., a feature that changes properties reversibly or irreversibly with stretch), strain sensing elements, photo-emitters, photodiodes, biasing features, bumps, touch sensors, pressure sensing elements, interfacial pressure sensing elements, piezoelectric elements, piezoresistive elements, chemical sensing elements, electrochemical cells, electrochemical sensors, redox reactive sensing electrodes, light sensitive structures, moisture sensitive structures, pressure sensitive structures, magnetic structures, bioadhesives, antennas, transistors, integrated circuits, transceivers, sacrificial structures, water soluble structures, temperature sensitive structures, light sensitive structures, light degrading structures, flexible light emitting elements, piezoresistive elements, moisture sensitive elements, mass transfer altering elements, etc.

In some embodiments, one or more of the sensors 316-328 have a controlled mass transfer property, such as a controlled moisture vapor conductivity so as to allow for a differential heat flux measurement through the patch or other disposable sampling unit 312. Such properties of one or more of the sensors 316-328 may be used in conjunction with the one or more temperature sensors 316 to obtain core temperature measurements of the user 336. It should be noted that one or more of the sensors 316-328 or the sensing unit 314 generally may be associated with signal conditioning circuitry used in obtaining core temperature or other measurements of physiologic parameters of the user 336. Core temperature measurements may, in some embodiments, be based at least in part on correlation parameters extracted from sensors of multiple wearable devices, or from sensors of the same wearable device that interface with different portions of the user 336. The correlation parameters may be based on thermal gradients computed as comparisons of multiple sensor readings (e.g., from a first subset of sensors oriented to make thermal contact with the user 336 and from a second subset of sensors oriented to make thermal contact with ambient surroundings, etc.). Core temperature readings may thus be estimated from the thermal gradients.

Changes in core temperature readings from multiple sensor readings over some designated period of time (e.g., a transitionary period where two wearable devices are attached to the user 336 and obtain core temperature readings) are analyzed to generate correlation parameters that relate changes in core temperature readings from the multiple sensors. In some embodiments, this analysis includes determining which of the multiple sensors has a lowest thermal gradient and weighting the correlation parameters to the sensor or device having the lowest thermal gradient. Consider an example where a first set of one or more sensors is at a first site on the user 336 and a second set of one or more sensors is at a second site on the user 336, with the first site being associated with a lower thermal gradient than the second site but with the second site being more conducive to long-term wear relative to the first site. In such cases, it may be desired to obtain core temperature readings from the first and second sets of sensors, establish the correlation parameter, and then subsequently use only the second set of sensors at the second site more conducive to long-term wear by the user 336. In some embodiments, the temperature sensors 316 comprise one or more digital infrared temperature sensors (e.g., Texas Instruments TMP006 sensors).

The heart rate sensors 318 in some embodiments are configured to sense physiological parameters of the user 336 such as conditions of the cardiovascular system of the user 336 (e.g., heart rate, blood pressure, heart rate variability, etc.). In some embodiments, the physiological parameters comprise one or more bioimpedance measurements, and correlation parameters may be generated by extracting local measures of water content from bioimpedance signals recorded from multiple sensors potentially at different sites on the body of the user 336. The local measures of water content recorded by different devices or sensors may be recorded during at least a portion of a transitionary period as described above to generate correlation parameters for application to bioimpedance signals recorded by the different sensors to offset at least a portion of identified differences therebetween. The correlated changes in the local measures of water content may be associated with a series of postural changes by the user 336.

The respiration sensors 320 are configured to monitor the condition of respiration, rate of respiration, depth of respiration, and other aspects of the respiration of the user 336. The respiration sensors 320 may obtain such physiological parameters by placing the wearable device 302 (e.g., a patch-module pair thereof) on the abdomen of the user 336 for monitoring movement or breathing, below the rib cage for monitoring respiration (generally on the right side of the body to substantially reduce EKG influences on the measurements), such placement enabling the respiration sensors 320 to provide rich data for respiration health, which may be advantageous in detection of certain infectious diseases that affect the respiratory tract of victims, such as, for example, coronavirus/COVID-19.

The pulse oximetry sensors 322 are configured to determine oxygen saturation (SpO2) using a pulse oximeter to measure the oxygen level or oxygen saturation of the blood of the user 336.

The accelerometer sensors 324 are configured to measure acceleration of the user 336. Single and multi-axis models of accelerometers may be used to detect the magnitude and direction of the proper acceleration as a vector quantity and can be used to sense orientation (e.g., based on the direction of weight changes), coordinate acceleration, vibration, shock, and falling in a resistive medium (e.g., a case where the proper acceleration changes, since it starts at zero then increases). The accelerometer sensors 324 may be embodied as micromachined microelectromechanical systems (MEMS) accelerometers present in portable electronic devices such as the wearable device 302. The accelerometer sensors 324 may also be used for sensing muscle contraction for various activities, such as running and other erect sports. In the case of running and other erect sports, resistance rises as either (or both) of the right and left extremities (e.g., feet, shins, knees, etc.) strike the ground. This rise or peak may be synchronized to bolus ejection as detailed herein. The accelerometer sensors 324 may detect such activity by measuring the body or extremity center of mass of the user 336. In some cases, the body center of mass may yield the best timing for the injection of fluid. Embodiments, however, are not limited solely to use with measuring the body center of mass.

The audio sensors 326 are configured to convert sound into electrical signals and may be embodied as one or more microphones or piezoelectric sensors that use the piezoelectric effect to measure changes in pressure, acceleration, temperature, strain, or force by converting them to an electrical charge. In some embodiments, the audio sensors 326 may include ultrasonic transducer receivers capable of converting ultrasound into electrical signals.

It should be noted that the sensors 316-326 described above are presented by way of example only, and that the sensing unit 314 may utilize various other types of sensors 328 as described elsewhere herein. For example, in some embodiments the other sensors 328 include one or more of motion sensors, humidity sensors, cameras, radiofrequency receivers, thermal imagers, radar devices, lidar devices, ultrasound devices, speakers, etc.

The GPS unit 330 is a component of the wearable device 302 configured to detect global position using GPS, a satellite-based radio navigation system owned by the U.S. government and operated by the U.S. Space Force. GPS is one type of global navigation satellite system (GNSS) that provides geolocation and time information to a GPS receiver anywhere on or near the Earth where there is an unobstructed line of sight to four or more GPS satellites.

The UWB unit 332 is a component of the wearable device 302 configured to detect UWB radiofrequencies. UWB is a short-range, wireless communication protocol similar to Bluetooth or WiFi, which uses radio waves at a very high frequency. Notably, UWB also uses a wide spectrum of several gigahertz (GHz). The functioning of a UWB sensor is to provide the ability to continuously scan an entire room and provide spatial awareness data to the wearable device 302, improving the localization of the wearable device 302 particularly in conjunction with use of the GPS unit 330.

The base software module 334 is configured to execute various functionality of the wearable device 302. Software programs or computer instructions for the base software module 334 when executed cause the processor 308 to poll the sensing unit 314 for sensor data from any combination of the sensors 316-328, to determine localization data using the GPS unit 330 and UWB 332, and to send the sensor data and the localization data to the wireless gateway 340 via the communications unit 306. The software programs or computer instructions from the base software module 334 may also cause the processor 308 to store the sensor data and localization data in the memory 310. The software programs or computer instructions of the base software module 334 may further cause the processor 308 to provide various other functionality such as testing and/or calibrating the sensing unit 314 or sensors 316-328 thereof, testing the power module 304, etc. Additional details regarding functionality of the base software module 334 will be provided below in the discussion of the process flow of FIG. 5.

The user 336 may be a human or animal to which the wearable device 302 is attached. The user 336 may be a patient that is being tested for one or more diseases associated with a global pandemic, such as coronavirus/COVID-19. In some embodiments, the user 336 is tested for symptoms of at least one disease while the user 336 is in isolation. Sensor data and localization data collected by the wearable device 302 may be provided to AI wearable device network 348 for analysis, with portions of such analysis being provided to one or more of the third-party networks 368 for various purposes such as monitoring, diagnosing and treating patients who may have been exposed to viral pathogens. Communication of the sensor and localization data from the wearable device 302 to the AI wearable device network 348 may take place via a wireless gateway 340, with the communication between the wireless gateway 340 and the AI wearable device network 348 taking place over one or more networks 384.

Figure 3C:
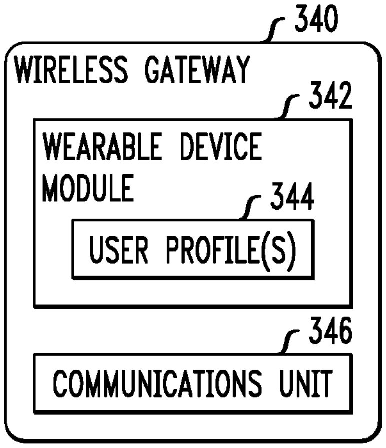
Figures 4, 5:
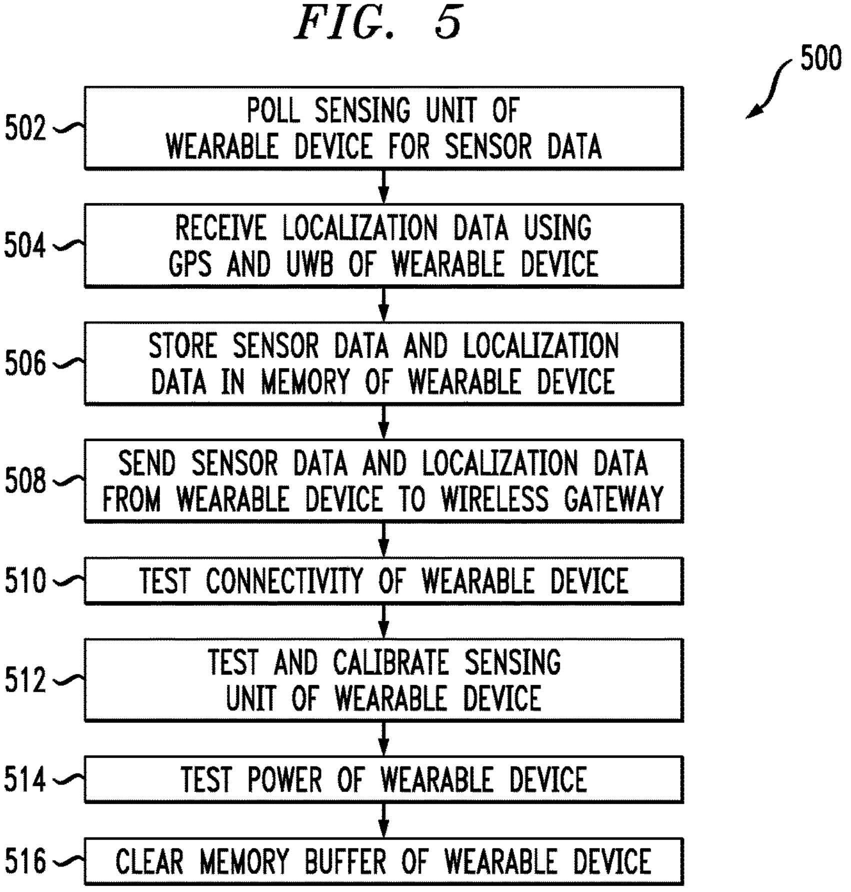
FIG. 4 illustrates a user profile utilized by the wearable device module of the wireless gateway in the FIG. 3 system, according to an embodiment of the invention.
FIG. 5 illustrates a process flow of operation of base software of the wearable device in the FIG. 3 system, according to an embodiment of the invention.

As shown in FIG. 3C, the user 336 may configure the wireless gateway 340 to include a user profile 344. The user profile 344 may include various health and physiological data about the user 336 that may not be obtained by sensors 316-328 of the wearable device 302. FIG. 4 shows an example of a user profile 400, which includes information such as a name and biological sex 402 (e.g., first, last and middle name), age 404 (e.g., in years), weight 406 (e.g., in pounds, kilograms, etc.), and height 408 (e.g., in feet or inches, in meters, etc.). The user profile 400 also includes known diseases and disorders 410 (e.g., asthma, allergies, current medications, family medical history, other medical data, etc.). Known diseases and disorders 410 may comprise various Protected Health Information (PHI) regulated by American Health Insurance Portability and Accountability Act (HIPAA) or other applicable rules and regulations. PHI includes individually identifiable health information that relates to one or more of: the past, present, or future physical or mental health or condition of an individual; provision of health care to the individual by a covered entity (e.g., a hospital or doctor); the past, present, or future payment for the provision of health care to the individual; telephone numbers, fax numbers, email addresses, Social Security numbers, medical record numbers, health plan beneficiary numbers, license plate numbers, uniform resource locators (URLs), full-face photographic images or any other unique identifying numbers, characteristics, codes, or combination thereof that allows identification of an individual. The user profile 400 further includes an emergency contact 412 (e.g., name, phone number, address, etc.), next of kin 414 (e.g., name, phone number, address, etc.), preferred hospital 416 (e.g., name, phone number, address, etc.) and primary care physician (PCP) 418 of the user 336 (e.g., name, phone number, place of business, etc.).

The wireless gateway 340 sends the sensor data and localization data obtained from the user 336 by the wearable device 302 utilizing communications unit 346, which may comprise any type of transceiver for coupling the wireless gateway 340 to the network 384. The communications unit 346 of the wireless gateway 340 may be embodied as communication circuitry or any communication hardware capable of transmitting an analog or digital signal over wired or wireless network interfaces. Such network interfaces may support not only communication with the AI wearable device network 348 over network 384, but also communications between the wearable device 302 and the wireless gateway 340. Any combination of network types may be utilized, including but not limited to NFC, WiFi, Bluetooth, IR, modem, cellular, ZigBee, BAN, etc.

The wireless gateway 340 may be, for example, a smartphone, a tablet, a laptop or desktop computer, an Internet-connected modem, a wireless router or standalone wireless hub device connected to the Internet, etc. The wireless gateway 340, in some embodiments, may itself comprise or be incorporated into one or more wearable devices (e.g., a smartwatch, an activity tracker, etc.). In some cases, the wireless gateway 340 may be part of the wearable device 302, or vice versa. The wireless gateway 340 is illustratively a smart device that is owned or controlled by the user 336, such as a smartphone, and allows rapid onboarding of wearable devices such as wearable device 302 to the AI wearable device network 348.

The wireless gateway 340 includes a wearable device module 342 that provides software programs or computer instructions for providing functionality of the wireless gateway 340. Although not shown in FIG. 3C, the wireless gateway 340 is assumed to comprise at least one processing device or controller including a processor coupled to a memory for executing the functionality of the wearable device module 342. Such functionality includes receiving the sensor data and the localization data from the wearable device 302 via the communications unit 346, and possibly performing a preliminary analysis of the sensor data and the localization data. Such analysis may be based at least in part on information stored in the user profile 344. Based on such analysis, the wearable device module 342 may determine whether any immediate notifications should be provided to the user 336. Such notifications may comprise, for example, indications of symptoms associated with at least one disease state. In other embodiments, the wearable device 340 functions as a pass-through entity and does not perform such preliminary analysis. Instead, the wireless gateway 340 may provide the sensor data and the localization data received from the wearable device 302, along with the associated user profile 344, to the AI wearable device network 348 over network 384 as a pass-through entity.

Regardless of whether or not the wireless gateway 340 performs such preliminary analysis, the wearable device module 342 of the wireless gateway 340 may receive any combination of diagnostic information, world health information, sensor data analysis, localization analysis, analysis created from a fusion of data from a plurality of sensors, etc. from the AI wearable device network 348. At least a portion of the received information is based on analysis of the sensor data, the localization data and the user profile 344 or information derived therefrom previously provided by the wireless gateway 340 to the AI wearable device network 348. At least a portion of the received information is used to generate notifications or other output via a graphical user interface (GUI) of the wireless gateway 340, the wearable device 302 or another type of local or remote indicator device.

The wearable device module 342 may provide functionality for determining notification settings associated with the user 336 and for executing or delivering notifications in accordance with the determined notification settings. The notification settings, in some embodiments, may specify the types of indicator devices that are part of or otherwise accessible to the wearable device 302 for delivering notifications to the user 336 (or to a doctor, nurse, physical therapist, medical assistant, caregiver, etc. associated with the user 336). The indicator devices in some embodiments may be configured to deliver visual or audible alarms. In other embodiments, the indicator devices may be configured to provide stimulus or feedback via stimulating devices as described elsewhere herein. Such stimulus or feedback, as detailed above, may include physical stimulus (e.g., electrical, thermal, vibrational, pressure, stroking, a combination thereof, or the like), optical stimulus, acoustic stimulus, etc. In some embodiments, notifications may be delivered to remote terminals or devices other than the wearable device 302 associated with user 336. For example, notifications may be delivered to one or more devices associated with a doctor, nurse, physical therapist, medical assistant, caregiver, etc. associated with the user 336.

The notification delivery method may also or alternatively comprise a visual or audible read-out or alert from a "local" device that is in communication with the wearable device 302. The local device may comprise, for example, a mobile computing device such as a smartphone, tablet, laptop etc., or another computing device, that is associated with the user 336. The wearable device 302 is one example of a local device. A local device may also include devices connected to the wearable device 302 via a BAN or other type of local or short-range wireless network (e.g., a Bluetooth network connection).

The notification delivery method may further or alternatively comprise a visual or audible read-out or alert from a "remote" device that is in communication with the wearable device 302 or the wireless gateway 340 via network 384. The remote device may be a mobile computing device such as a smartphone, tablet, laptop, etc., or another computing device (e.g., a telemetry center or unit within a hospital or other facility), that is associated with a doctor, nurse, physical therapist, medical assistant, caregiver, etc. monitoring the user 336. It should be understood that the term "remote" in this context does not necessarily indicate any particular physical distance from the user 336. For example, a remote device to which notifications are delivered may be in the same room as the user 336. The term "remote" in this context is instead used to distinguish from "local" devices (e.g., in that a "local" device in some embodiments is assumed to be owned by, under the control of, or otherwise associated with the user 336, while a "remote" device is assumed to be owned by, under the control of, or otherwise associated with a user or users other than the user 336 such as a doctor, nurse, physical therapist, medical assistance, caregiver, etc.).

The indicator devices may include various types of devices for delivering notifications to the user 336 (or to a doctor, nurse, physical therapist, medical assistant, caregiver, etc. associated with the user 336). In some embodiments, one or more of the indicator devices comprise one or more light emitting diodes (LEDs), a liquid crystal display (LCD), a buzzer, a speaker, a bell, etc., for delivering one or more visible or audible notifications. More generally, the indicator devices may include any type of stimulating device as described herein which may be used to deliver notifications to the user 336 (or to a doctor, nurse, physical therapist, medical assistant, caregiver, etc. associated with the user 336).

Figure 6:
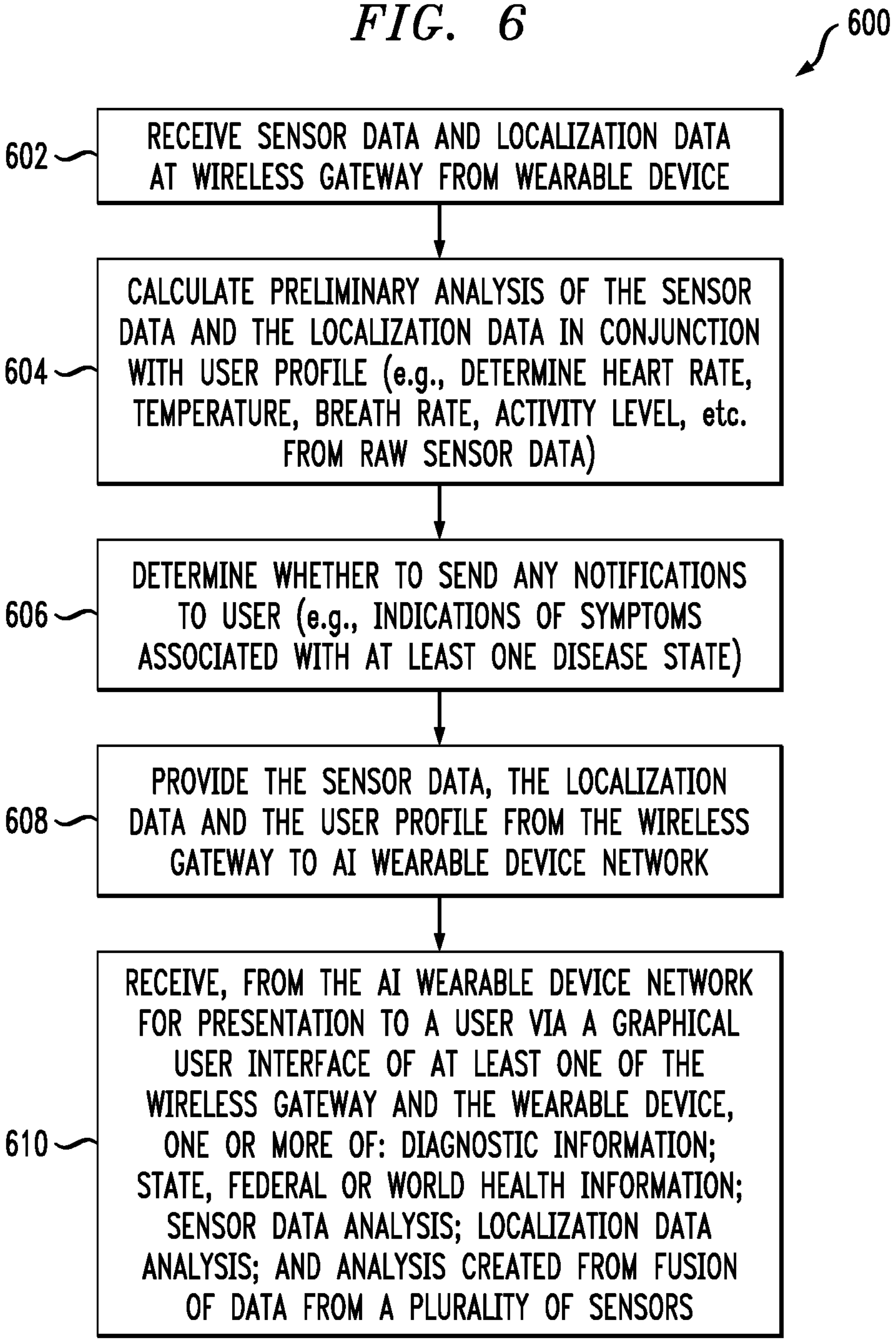
FIG. 6 illustrates a process flow of operation of the wearable device module of the wireless gateway in the FIG. 3 system, according to an embodiment of the invention.

Additional details regarding the functionality of the wearable device module 342 will be provided below in conjunction with the process flow of FIG. 6.

FIG. 3A also shows the crowd of users 338, each of which is assumed to provide sensor data and localization data obtained by a plurality of wearable devices to the AI wearable device network 348, possibly via respective wireless gateways. The wearable devices and wireless gateways for the crowd of users 338 may be configured in a manner similar to that described herein with respect to the wearable device 302 and wireless gateway 340 associated with the user 336.

Figure 3D:
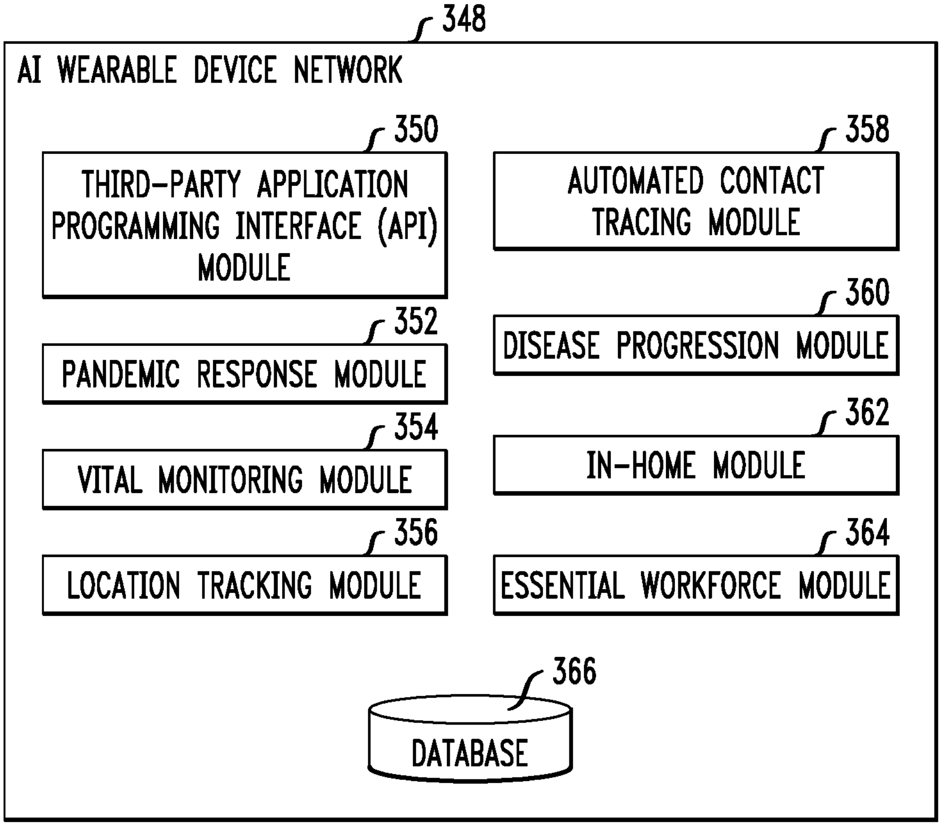

The AI wearable device network 348 is configured to receive data (e.g., sensor data, localization data, user profiles, preliminary analysis of sensor and localization data, etc.) from the wireless gateway 340 and the crowd of users 338. The AI wearable device network 348 analyzes the received data using various software modules implementing AI algorithms for determining disease states, types of symptoms, risk of infection, contact between users, condition of physiological parameters, etc. As shown in FIG. 3D, such modules include a third-party application programming interface (API) module 350, a pandemic response module 352, a vital monitoring module 354, a location tracking module 356, an automated contact tracing module 358, a disease progression module 360, an in-home module 362 and an essential workforce module 364. The AI wearable device network 348 also includes a database 366 configured to store the received data, results of analysis on the received data, data obtained from third-party networks 368, etc.

In some embodiments, the AI wearable device network 348 is implemented as an application or applications running on one or more physical or virtual computing resources. Physical computing resources include, but are not limited to, smartphones, laptops, tablets, desktops, wearable computing devices, servers, etc. Virtual computing resources include, but are not limited to, VMs, software containers, etc. The physical and/or virtual computing resources implementing the AI wearable device network 348, or portions thereof, may be part of a cloud computing platform. A cloud computing platform includes one or more clouds providing a scalable network of computing resources (e.g., including one or more servers and databases). In some embodiments, the clouds of the cloud computing platform implementing the AI wearable device network 348 are accessible via the Internet over network 384. In other embodiments, the clouds of the cloud computing platform implementing the AI wearable device network 348 may be private clouds where access is restricted (e.g., such as to one or more credentialed medical professionals or other authorized users). In these and other embodiments, the AI wearable device network 348 may be considered as forming part of an emergency health network comprising at least one server and at least one database (e.g., the database 366) storing health data pertaining to a plurality of users (e.g., the user 336 and crowd of users 338).

The database 366 provides a data store for information about patient conditions (e.g., information about the user 336 and crowd of users 338), information relating to diseases including epidemics or pandemics, etc. Although shown as being implemented internal to the AI wearable device network 348 in FIG. 3D, it should be appreciated that the database 366 may also be implemented at least in part external to the AI wearable device network 348 (e.g., as a standalone server or storage system). The database 366 may be implemented as part of the same cloud computing platform that implements the AI wearable device network 348.

Figure 3E:
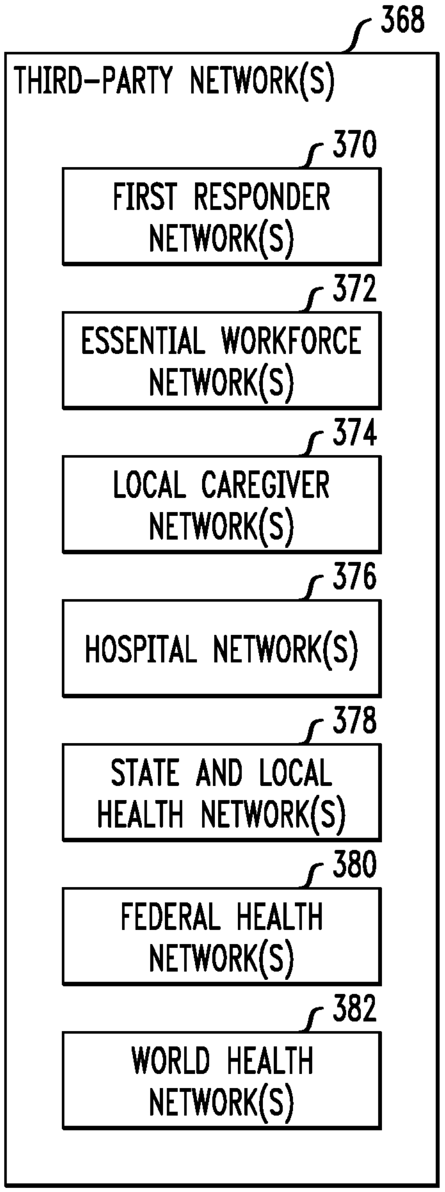

The AI wearable device network 348 may exchange various information with third-party networks 368. As shown in FIG. 3E, the third-party network 368 may include any combination of one or more first responder networks 370, one or more essential workforce networks 372, one or more local caregiver networks 374, one or more hospital networks 376, one or more state and local health networks 378, one or more federal health networks 380, one or more world health networks 382, etc. Third party-networks 368 may also include telemedicine networks. Under certain circumstances, as permitted by the verification entity 386, one or more of the third-party networks 368 may receive data and analysis from the AI wearable device network 348 for various purposes including but not limited to diagnosis, instruction, pandemic monitoring, disaster response, resource allocation, medical triage, any other tracking or intervention of global pandemics and associated logistics, etc. The first responder networks 370 may include any person or team with specialized training who is among the first to arrive and provide assistance at the scene of an emergency, such as an accident, natural disaster, terrorism, etc. First responders include, but are not limited to, paramedics, emergency medical technicians (EMTs), police officers, fire fighters, etc. The essential workforce networks 372 may include networks for employers and employees of essential workforces of any company or government organization that continues operation during times of crises, such as a viral pandemic. Essential workforces include, but are not limited to, police, medical staff, grocery workers, pharmacy workers, other health and safety service workers, etc. The local caregiver networks 374 may include a network of local clinics, family doctors, pediatricians, in-home nurses, nursing home staff, and other local caregivers. The hospital networks 376 allow transfer of data between hospitals and the AI wearable device network 348.

The exchange of information between the AI wearable device network 348 and third-party networks 368 may involve use of a verification entity 386, which ensures data security in accordance with applicable rules and regulations (e.g., HIPAA). The AI wearable device network 348 utilizes the third-party API module 350 to perform such verification of the third-party networks 368 utilizing the verification entity 386, before providing any data or analysis thereof related to the user 336 or crowd of users 338 to any of the third-party networks 368. It should be noted that, if desired, any data or analysis related to the user 336 or crowd of users 338 may be anonymized prior to being sent to one or more of the third-party networks 368, such as in accordance with privacy settings in user profiles (e.g., user profile 344 associated with the user 336, user profiles associated with respective users in the crowd of users 338, etc.).

The pandemic response module 352 is configured to execute processes based on receiving pandemic data from one or more of the third-party networks 368 via the third-party API module 350. The pandemic response module 352 may analyze such received information and provide notifications to the user 336 or crowd of users 338 including relevant information about the pandemic. The pandemic response module 352 may further collect and analyze physiological data of the user 336 or crowd of users 338 that may be relevant to the pandemic, and provides instructions to users who may be at risk due to the pandemic. Information about such at-risk users may also be provided to one or more of the third-party networks 368. The pandemic response module 352 may continually update the database 366 with relevant pandemic data including information about at-risk users. The pandemic response module 352, while described herein as processing information related to pandemics, may also be configured to process information related to epidemics and other outbreaks of diseases that do not necessarily reach the level of a pandemic. The pandemic response module 352 may also process information from the user 336 and crowd of users 338 so as to predict that a pandemic, epidemic or other disease outbreak is or is likely to occur. Thus, the functionality of the pandemic response module 352 is not limited solely to use in processing pandemic information.

The vital monitoring module 354 may monitor and analyze physiological data of the user 336 and crowd of users 338 to detect and mitigate pandemics, epidemics and other outbreaks or potential outbreaks of diseases. The physiological data may be analyzed to determine if there is evidence of a disease associated with a pandemic (e.g., shortness of breath associated with respiratory illness).

The location tracking module 356 is configured to track the location of user 336 and the crowd of users 338 to determine whether any of such users enter or exit regions associated with a pandemic or other outbreak of a disease. The location tracking module 356, in some embodiments, may alert users who have entered a geographic location or region associated with increased risk of exposure to an infectious disease (e.g., associated with an epidemic, pandemic or other outbreak). In some embodiments, various alerts, notifications and safety instructions are provided to the user 336 and crowd of users 338 based on their location. The threshold for detection of symptoms associated with an infectious disease (e.g., associated with an epidemic, pandemic or other outbreak) may be modified based on location of the user 336 and crowd of users 338. For example, the threshold for detecting a symptom (e.g., shortness of breath) may be lowered if the user 336 or crowd of users 338 are in high-risk locations for contracting an infectious disease.

The automated contact tracing module 358 is configured to use the tracked location of the user 336 and crowd of users 338 (e.g., from the location tracking module 356) so as to determine possible contacts between such users and also to assess risk of infection on a per-user basis. The automated contact tracing module 358 may also automate the delivery of notifications to the user 336 and crowd of users 338 based on potential exposure to other users or geographic regions associated with a pandemic or other outbreak of a disease. The automated contact tracing module 358 may further provide information regarding contacts between the user 336 and crowd of users 338 to one or more of the third-party networks 368 (e.g., indicating compliance with risk mitigation strategies for pandemic response).

The disease progression module 360 is configured to analyze physiologic data from the user 336 and crowd of users 338, and to determine whether such physiologic data is indicative of symptoms of a disease. As new physiologic data from the user 336 and crowd of users 338 is received, trends in such data may be used to identify the progression of a pandemic or other outbreak of a disease. The disease progression module 360 may be configured to monitor the progression of specific infectious diseases, such as infectious diseases associated with epidemics, pandemics or other outbreaks, based on any combination of: user indication of a contracted disease; one or more of the third party networks 368 indicating that users have contracted a disease; the vital monitoring module 354 detecting a user contracting a disease with probability over some designated threshold; etc. The disease progression module 360 is further configured to compare disease progress for different ones of the users 336 and crowd of users 338 with typical disease progress to determine individual user health risk.

The in-home module 362 is configured to analyze location data from the user 336 and crowd of users 338, and to determine whether any of such users are in locations with stay-at-home or other types of quarantine, social distancing or other self-isolation orders or recommendations in effect. If so, the in-home module 362 may provide notifications or alerts to such users with instructions for complying with the stay-at-home, quarantine, social distancing or other self-isolation orders or recommendations, for mitigating an infectious disease, for preventing spread of the infectious disease, etc. The in-home module 362 may be further configured to provide in-home monitoring of infected patients that are quarantined or self-isolated at home, providing warnings to such users that leave the home, instructions for mitigating the disease, etc. The in-home module 362 may further provide in-home monitoring data to one or more of the third-party networks 368.

The essential workforce module 364 is configured to identify ones of the user 336 and crowd of users 338 that are considered part of an essential workforce or are otherwise considered essential personnel. Once identified, the essential workforce users' physiologic data may be analyzed to determine risk profiles for such users, and the algorithms implemented by modules 350 through 362 may be modified accordingly. As one example, the functionality of the in-home module 362 may be modified such that alerts or notifications are not sent to essential workforce users when leaving areas associated with stay-at-home, quarantine, social distancing or other self-isolation orders (e.g., those users would not receive alerts or notifications when traveling to or from their associated essential workplaces). Various other examples are possible, as will be described elsewhere herein.

Additional details regarding functionality of the modules 350 through 364 of the AI wearable device network 348 will be described in further detail below with respect to the process flows of FIGS. 7-14.

Functionality of the base software module 334 of the wearable device 302 will now be described in further detail with respect to the process flow 500 of FIG. 5. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The process 500 begins with step 502, where the base software module 334 polls the sensing unit 314 for sensor data related to one or more of the sensors 316-328. As discussed above, the sensors 316-328 may include any combination of one or more temperature or body thermometer sensors 316, heart rate sensors 318, respiration sensors 320, pulse oximetry sensors 322, accelerometer sensors 324, audio sensors 326 and various other sensors 328 (e.g., gyroscopes, magnetometers, pedometers, activity trackers, skin conductivity sensors, electrocardiogram sensors, etc.). In step 504, the base software module 334 obtains localization data, such as by polling one or a combination of the GPS unit 330, the UWB unit 332 and possibly one or more of the sensors 316-328 (e.g., the audio sensors 326). Localization of the wearable device 302 (and thus, the user 336 that is wearing or otherwise associated with the wearable device 302) may pertain to, for example, geographic location such as continent, country, state, city, neighbor, address, etc., as well as environmental localization, e.g., indoor, outdoor, public space, private space, city, green space, etc. In some embodiments, the localization data may include sensor data used in determining if the user 336 is in a more or less densely populated area, such as a high-rise apartment building or a single family house, which may have implications on the health risks of the user 336 as it pertains to one or more infectious diseases (e.g., including global pandemics). The UWB unit 332 may be used to provide "see-through-the-wall" precision radar-imaging technology, precision location and tracking (e.g., using distance measurements between radios), and precision time-of-arrival-based localization approaches. The use of UWB information from the UWB unit 332 is efficient, with a spatial capacity of approximately 1013 bits per second per meter square (bit/s/$m^2$).

The base software module 334 stores the sensor data obtained in step 502 and the localization data obtained in step 504 in the memory 310 of the wearable device 302 in step 506. In step 508, the sensor data and the localization data is sent from the wearable device 302 to the wireless gateway 340 via the communications unit 306. The sensor data and the localization data may be sent using various types of communications channels, including but not limited to Ultra-Low Power (ULP) networks such as Bluetooth 4.0 or ZigBee IEEE 802.15.3, cellular 3G, CDMA or 3GPP, 4G LTE networks, 5G networks, WiFi, etc. The sensor data may be encrypted or have other security mechanisms applied to it, such that the sensor data may be securely transmitted to any combination of the AI wearable device network 348, one or more of the third-party networks 368, etc.

The process 500 also includes various optional steps, such as testing connectivity of the wearable device 302 in step 510, testing and calibrating the sensing unit 314 (or sensors thereof) of the wearable device 302 in step 512, testing the power module 304 of the wearable device 302 in step 514, and clearing a buffer of the memory 310 of the wearable device 302 in step 516. In some embodiments, the wearable device 302 may include a modular physiologic monitoring system as described above with respect to FIGS. 1 and 2A-2C, that includes one or more modules with each module including self-diagnostic functionality. The self-diagnostic functionality may include reading a battery voltage level of the power source 304 (e.g., a battery, a rechargeable battery, an energy harvesting transducer, a microcircuit, an energy reservoir, a thermal gradient harvesting transducer, a kinetic energy harvesting transducer, a radio frequency energy harvesting transducer, a fuel cell, a biofuel cell, etc.).

Functionality of the wearable device module 342 of the wireless gateway 340 will now be described in further detail with respect to the process flow 600 of FIG. 6. The process 600 begins with step 602, receiving the sensor data and the localization data at the wireless gateway 340 from the wearable device 302. As described above, the sensor data may include information from various sensors 316-328 of the sensing unit 314 of the wearable device 302 (e.g., temperature sensors or body thermometers, accelerometers, gyroscopes, magnetometers, pedometers, and other activity trackers, heart rate sensors, bioimpedance sensors, skin conductivity sensors, electrocardiogram sensors, pulse oximeters, etc.). The localization data may be data that is obtained from, or interpolated or otherwise derived from, data associated with the GPS unit 330, the UWB unit 332, ambient audio from audio sensors 326, etc. The wearable device module 342 may provide further localization data, in isolation or in combination with the localization data received from the wearable device 302. Such further localization data may include an IP address, WiFi Service Set Identifier (SSID) signature, cellular positioning, GPS information from the wireless gateway 340, data associated with a navigation application running on the wireless gateway 340, etc.

In step 604, the wearable device module 342 calculates a preliminary analysis of the sensor data and the localization data received in step 602, in combination with information from the user profile 344. The preliminary analysis may include, for example, determining various metrics from raw sensor data. It should be noted that the processor 308 of the wearable device 302 may also perform some preliminary analysis such as deriving metrics from raw sensor data. The preliminary analysis may include determining metrics such as heart rate, breath rate, activity level, etc. from the raw sensor data. The calculations in step 604 may be based on at least one symptom or disease state (e.g., body temperature above 101 degrees Fahrenheit may be associated with the disease state of "fever"). The calculations in step 604 may also or alternatively be based on or associated with a risk of the user 336 associated with at least one symptom or disease state (e.g., an increased risk of respiratory disease based on location and shortness of breath). In some embodiments, the user 336 may provide qualitative input to the wearable device module 342 of the wireless gateway 340 in order to contextualize the sensor data and/or the localization data (e.g., shortness of breath associated with running to catch a bus). The calculations in step 604 may be based on the specific location of the user 336, or on various features of the user profile 344 (e.g., age, sex, other known diseases and disorders, etc.). In the case of pandemic diseases, such as COVID-19, age (e.g., ages 60 and up) and known diseases and disorders (e.g., asthma, diabetes, heart disease, etc.) may be indicators that users are more vulnerable to becoming severely ill and thus the threshold for risk detection may be adjusted. In some embodiments, the calculations in step 604 may be based on the location of the sensors 316-328 with respect to the body of the user 336. The user 336 may indicate device placement in the user profile 344, or as part of messages sent to the wireless gateway 340 (e.g., including messages that comprise portions of the sensor data and the localization data). The placement of the sensors may be automatically detected in other embodiments.

In step 606, the wearable device module 342 determines any immediate notifications to send to the user 336. The immediate notifications may include, for example, indication of symptoms associated with at least one disease state (e.g., shortness of breath associated with the onset of a coronavirus disease such as COVID-19 or other common symptoms of such a disease such as fever, tiredness, dry cough, etc.). In some embodiments, the frequency at which symptoms are monitored may increase based on identifying one or more symptoms of a disease. For example, on detecting a fever, the frequency at which sensor data is monitored for shortness of breath, tiredness or dry cough may be increased.

In some cases, the preliminary analysis indicates symptoms that are sufficient to trigger notifications sent to third-party networks 368 in step 608. For example, notifications may be triggered to local caregivers associated with the user 336. In such embodiments, the notifications sent to the third-party networks 368 include information related to detected symptoms of the user 336, the sensor data and the localization data or metrics derived therefrom on which the step 604 calculations are based, etc. The wireless gateway 340 may provide such notifications via the third-party API module 350 of the AI wearable device network 348 in step 608. The wireless gateway 340 may also or alternatively provide the sensor data, the localization data and the user profile 344 to the AI wearable device network 348 as a pass-through entity in step 608.

In step 610, the wearable device module 342 of the wireless gateway 340 receives from the AI wearable device network 348 various information, such as diagnostic information, world health information, sensor data analysis, localization analysis, analysis created from a fusion of data from the sensors 316-328 of the wearable device 302 and other sources, etc. The received information in step 610 may be presented to the user 336 via a GUI on the wireless gateway 340 and/or the wearable device 302. The user 336 may thereby annotate or manipulate the received data (e.g., by inputting specific location or activity information associated with the data or a portion thereof, by inputting qualitative experience of symptoms such as heavy coughing, etc.). The user 336 may also elect to send the received data or a portion thereof to trusted ones of the third-party networks 368 such as one or more of the local caregiver networks 374. Analysis from the AI wearable device network 348 may provide the user 336 further instruction for monitoring symptoms and progress of disease, such as, for example, directing the user 336 to a local testing center for more accurate testing and diagnosis of a potential disease. In other embodiments, based on the state of health of the user 336 and a global state of health care response to pandemics, the AI wearable device network 348 may provide the user 336 with instructions for remaining at home, avoiding public places, etc., in order to self-isolate or otherwise practice social distancing, quarantining, etc. to prevent the acquisition and distribution of contagious pathogens.

Figure 7:
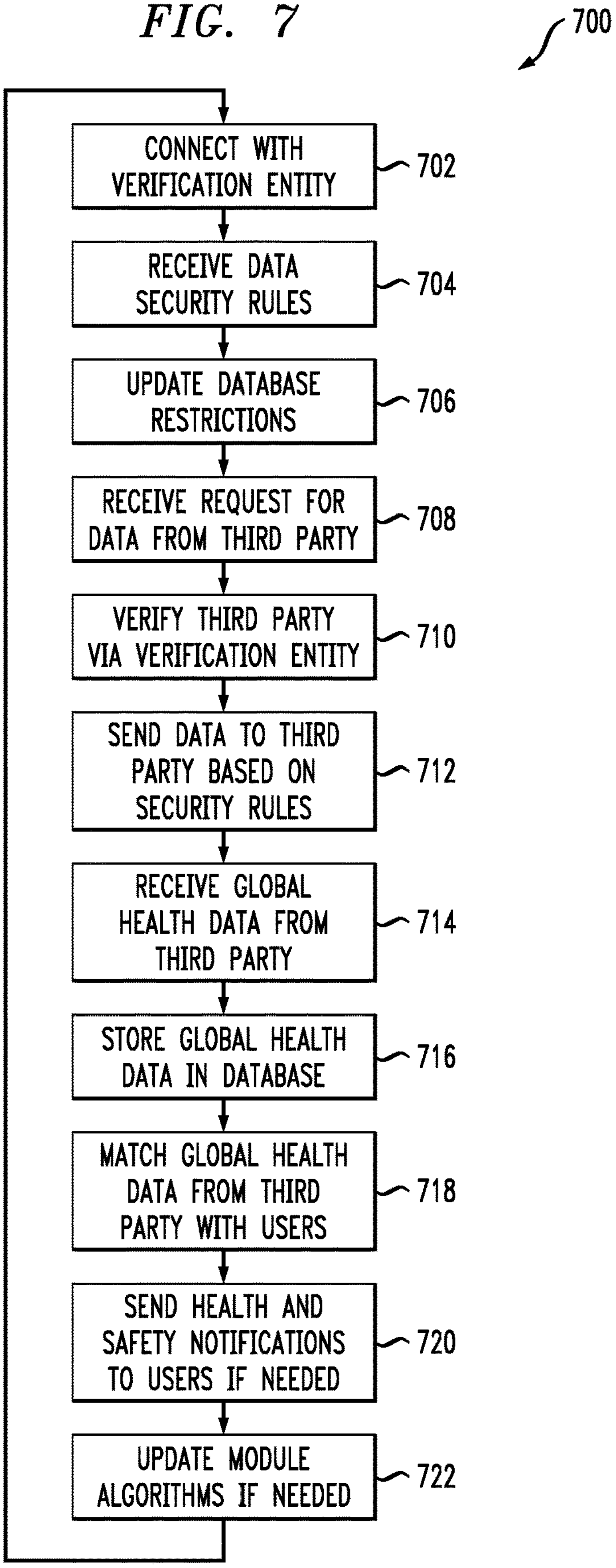
FIG. 7 illustrates a process flow for operation of the third-party application programming interface module of the artificial intelligence wearable device network in the FIG. 3 system, according to an embodiment of the invention.

Functionality of the third-party API module 350 of the AI wearable device network 348 will now be described in further detail with respect to the process flow 700 of FIG. 7. The process 700 begins in step 702 with the third-party API module 350 connecting with the verification entity 386. In some embodiments, the verification entity 386 is associated with an Automated Eligibility Verification System (AEVS), an Electronic Visit Verification (EVV) system, or another system that is in compliance with applicable rules and regulations (e.g., U.S. and world medical record-keeping practices such as HIPAA), which allows users in affected jurisdictions to access medical information and send it to the third-party networks 368 as they desire. The verification entity 386 may include any combination of various cyber-security verification modules configured to handle specific modes of encryption, data handling, anonymization, tokenization, and/or biometric verification steps in order for data to be transferred from the AI wearable device network 348 to one or more of the third-party networks 368.

During an incident relating to an epidemic, pandemic or other outbreak of an infectious disease, verified communication with third-party networks 368 such as the first responder networks 370 and local caregiver networks 374 becomes especially critical. Emergency communications with the first responder networks 370, local caregiver networks 374 and possibly other ones of the third-party networks 368 may include: alerts and warnings; directives about evacuation, curfews and other self-protective actions; information about response status, family members, available assistance, and other matters that impact response and recovery; etc. Well-conceived and effectively delivered emergency messages can help ensure public safety, protect property, facilitate response efforts, elicit cooperation, instill public confidence, and help families reunite. The extent to which people respond to a warning message is influenced by many factors, including individual characteristics and perceptions, whether the message comes from a credible source, how the message is delivered, and the message itself. In some embodiments many communication tools may be used, including text, audio, video, graphical or statistical information, a direct communication with an operator or dispatcher, etc. Each has advantages and limitations, and thus each communication tool may be used synchronously, asynchronously, or in any combination or in isolation, depending on communication objectives and the intended audience provided by verified ones of the third-party networks 368. In some embodiments, the verification entity 386 may be, for example, a federal agency, such as the Federal Trade Commission (FTC), which can coordinate the creation and enforcement of comprehensive privacy and security standards.

In step 704, the third-party API module 350 receives data security rules for the verification entity 386. The data security rules provide a match between the third-party networks 368, the user 336 and crowd of users 338 (and their associated user types), and the wearable device data and types of data associated with the user 336 and crowd of users 338. This may include, for example, matching health insurers with insured users and allowing health insurers to provide medical data to and receive medical data from the AI wearable device network 348 pertaining to the insured users based on the security rules of both the insured user and the health insurer as provided by the verification entity 386. In other embodiments, local caregivers associated with local caregiver networks 374, hospitals associated with hospital networks 376, state and local governments associated with state and local health networks 378, federal governments associated with federal health networks 380, world health organizations associated with world health networks 382 (or entities associated with any other of the third-party networks 368) may also obtain or provide data to and from the AI wearable device network 348 based on security rules provided by the verification entity 386.

Database restrictions for the database 366 are updated in step 706. Such restrictions may include, for example, encryption parameters of specific users and associated user data. There may be specific security restrictions for specific types of data (e.g., personally identifying information). In some embodiments, updating the database restrictions in step 706 includes providing updates to database security, where database security concerns the use of a broad range of information security controls to protect the database 366 against compromises of confidentiality, integrity and availability. This may involve various types or categories of controls, such as technical, procedural or administrative, and physical.

In step 708, the third-party API module 350 receives requests for data from third parties associated with one or more of the third-party networks 368. One or more of the essential workforce networks 372, for example, may request data associated with a set of users that are employed in essential workforce occupations. The essential workforce networks 372 thereby provide analysis of the data to correlate, predict shortages, forecast infections, model various scenarios, etc., so as to optimize the health and utilization of essential workforce users. Consider, as an example, a grocery store that wishes to monitor its staff via a set of wearable devices, so as to determine the overall health of various individuals and departments and reassess staffing needs and exposure targets. The grocery store may thus request and receive physiological and/or localization data pertaining to users who are employees thereof, and use the data to determine schedules, to determine sick callouts, to anticipate staffing shortages, to request various employees stay home, to hire temporary workers, etc. The hospital networks 376 may request the data associated with an in-patient who is a user (e.g., user 336) of a wearable device (e.g., wearable device 302). Various other use cases involve different ones of the third-party networks 368 requesting or providing data to the AI wearable device network 348 via the third-party API module 350.

The third party or parties requesting data in step 708 are verified in step 710 using the verification entity 386. Verification may include transfer of digital credentials, biometric verifications from a verified agent of the verification entity 386, one or more of the third-party networks 368, the AI wearable device network 348, or any combination thereof. In some embodiments, the verification entity 386 includes an identity verification service used to ensure that users or third-party networks 368 (or agents thereof) provide information that is associated with the identity of a real person. The identity verification service may verify the authenticity of physical identity documents such as a driver's license, passport or other state or nationally issued identity documents through documentary verification. In step 712, the requested data is sent to the requesting third-party based on the security rules. For example, a hospital associated with one or more hospital networks 376 may have previously requested the data associated with an in-patient who is a user of a wearable device (e.g., user 336 associated with wearable device 302), with the hospital networks 376 verifying through the verification entity 386. Such verification may be by an agent providing credentials, biometric verification or other identity verification in order to receive the requested data (e.g., heart rate, pulse oximetry, respiration data, or other physiological data associated with the in-patient). As another example, one or more of the essential workforce networks 372 may have requested data associated with a set of users who each are employed in essential workforce occupations, the essential workforce networks 372 thereby verifying via the verification entity 386 to receive the requested data (e.g., physiological data and/or localization data). The essential workforce networks 372 may perform analysis of the requested data to correlate and predict shortages or forecast infections, model various scenarios, optimize the health and utilization of the essential workforce users, etc.

In some embodiments, the requesting third party may send additional data and analysis to the AI wearable device network 348, which may or may not be directly associated with the users whose data the third party previously received. For example, a grocery store may wish to monitor its staff via a set of wearable devices to determine the overall health of various individuals and departments, to reassess staffing needs, to determine exposure targets, etc. The grocery store may thereby receive physiological and/or localization data pertaining users who are employees, and use the data to determine schedules, to determine essential workforce users who are or may potentially be sick, to anticipate staffing shortages, to request various employees stay home, to hire temporary workers, etc. In this example, the grocery store may only be able to access data for users who have both verified employment and authorized the employer to monitor their associated physiological and localization data.

In some embodiments, the data sent to the requesting third party may only include a general analysis for a particular set of users, with individual identities and associated personally identifiable information redacted or anonymized. Continuing with the example above, in such a case the grocery store may use such information to make staff or department level decisions without regards to the physiological or localization data of particular ones of the users in the set of users.

In step 714, the third-party API module 350 receives global health data from one or more third parties. Such global health data may include any data, analysis, notifications, advisements, instructions, etc., associated with any updated symptoms, risk factors, sensor thresholds, disease progress algorithms, health and safety notifications, or other types of knowledge transfer between third-party health entities associated with one or more of the third-party networks 368 and the users 336 and crowd of users 338 of the AI wearable device network 348. In some embodiments, the global health data includes data related to a global pandemic (e.g., COVID-19, a disease caused by a novel strain of coronavirus that is significant for its highly contagious infection pattern and high mortality rate). The global health data may include thresholds for symptoms associated with the global pandemic or other outbreak of a disease (e.g., body temperature above 100 degrees Fahrenheit, respiratory rate indicating shortness of breath, detection of dry cough, localization associated with the outbreak, such as affected countries, airports, or other public locations, etc.), instructions for user safety (e.g., wash hands for 20 seconds, avoid public places, work from home etc.), information for contacting appropriate emergency services, locations and resources (e.g., online or geographic locations, such as testing centers), incentives for disseminating wearable devices to friends and family members to increase compliance and protection, etc.

The global health data received in step 714 is stored in the database 366 in step 716. The data may include, but is not limited to, data, analysis, notifications, advisements, instructions, etc. associated with any updated symptoms, risk factors, sensor thresholds, disease progress algorithms, health and safety notifications, or other types of knowledge transfer between third party health entities and users 336 and crowd of users 338 of the AI wearable device network 348, which may or may not be associated with specific users based on their associated user profiles, occupation, type of wearable device, etc. In step 718, the global health data received from third parties is matched with the user 336 and crowd of users 338 (e.g., based on location, age, known diseases and conditions, other user profile data, etc.). The AI wearable device network 348 analyzes the global health data provided by the third party with specific ones of the user 336 and crowd of users 338, with such users being matched based on their user profile data (e.g., name, age, weight, height, known diseases and disorders, emergency contact, next of kin, preferred hospital, PCP, etc.), associated wearable device sensor data (e.g., temperature, heart rate, respiration, pulse oximeter, accelerometer, audio and other sensor readings, etc.), associated localization data (e.g., GPS data, UWB data, ambient audio data, etc.), etc.

Health and safety notifications are sent to users, if determined to be necessary or advisable, in step 720. As an example, all users in a high risk geographic area (e.g., New York City) may be provided warnings and instructions based on their age, location and other disease states. The health and safety notifications may include warnings and instructions based on their age, location and other disease states. The warnings and instructions may include, for example, recommendations to avoid social contact for at least two weeks, apply wearable devices to their chests to monitor respiratory health, wash hands, etc. In step 722, algorithms used by other ones of the modules 352-364 may be modified if needed (e.g., with updated symptoms, risk factors, sensor thresholds, disease progress algorithms, etc.). Such updates include, for example, modifications to the sensitivity of various symptom detection algorithms (e.g., shortness of breath may be a low priority symptom during the normal course of medicine, but during a coronavirus/COVID-19 pandemic, shortness of breath may indicate symptoms associated with the pandemic disease and thus the disease progression module 360 thereby lowers the threshold for detecting shortness of breath). In some embodiments, the algorithms may be modified based on health data provided by third parties such as world health networks 382, in order to optimize the algorithms for detection and mitigation of symptoms and user behaviors associated with a global health pandemic. Following step 722, the process 700 may loop back to the beginning in step 702.

Figure 8:
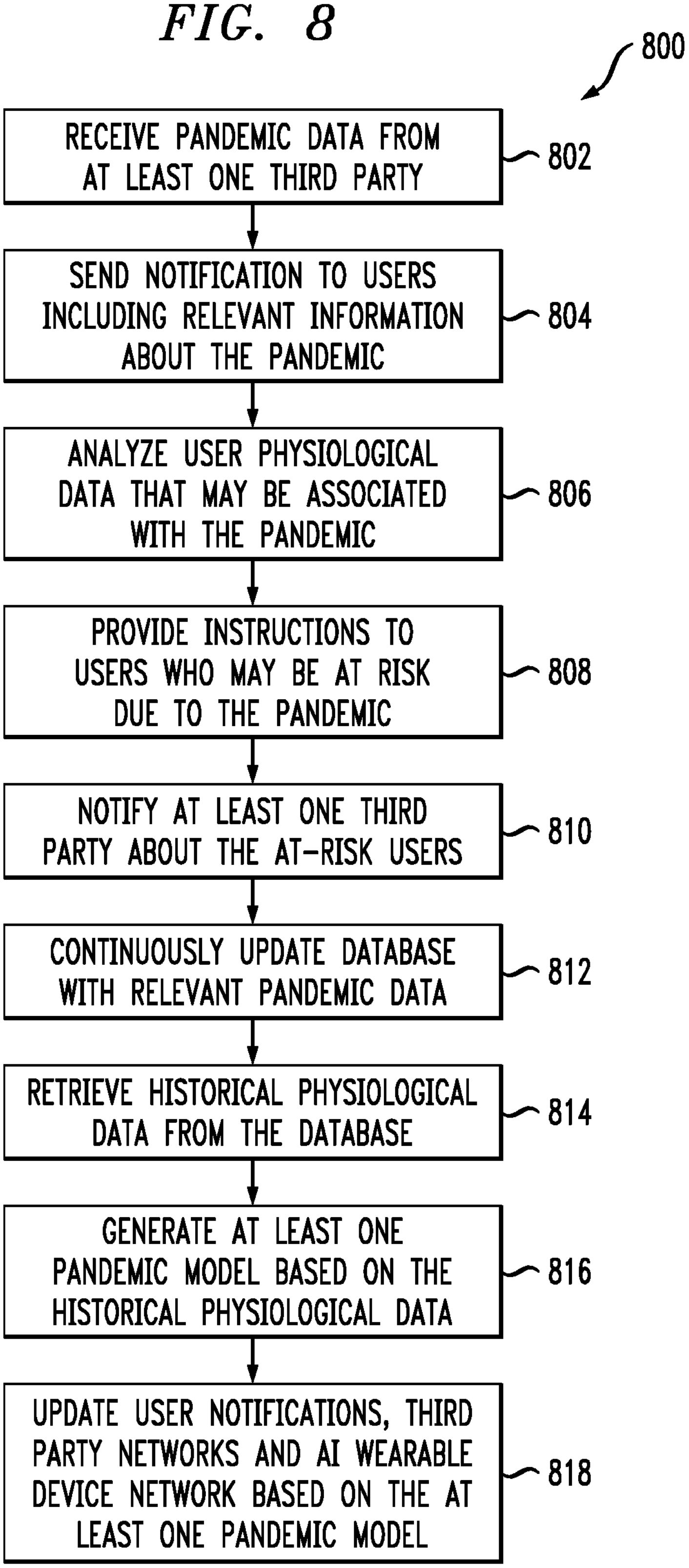
FIG. 8 illustrates a process flow for operation of the pandemic response module of the artificial intelligence wearable device network in the FIG. 3 system, according to an embodiment of the invention.

Functionality of the pandemic response module 352 of the AI wearable device network 348 will now be described in further detail with respect to the process flow 800 of FIG. 8. The process 800 begins in step 802 with receiving pandemic data from at least one third party via the third-party API module 350. The pandemic data may be data associated with modeling and mapping a viral epidemic which may be, for example, coronavirus or COVID-19 (also referred to as 2019-nCoV). In some embodiments, the model may integrate both outbreak dynamics and outbreak control into a decision-support tool for mitigating infectious disease pandemics at the onset of an outbreak through monitoring physiologic and localization data to evaluate the pandemic (e.g., the 2019-nCoV epidemic). The pandemic response module 352 may also utilize stochastic metapopulation epidemic simulation tools to simulate global outbreak dynamics and determine measures for response thereto (e.g., passenger screening upon arrival at airports or other entry screening which is used to identify infected or at-risk individuals). In step 804, the pandemic response module 352 sends notifications to the user 336 and crowd of users 338 including relevant information about the pandemic. For example, a notification may include advice on how to stay safe, such as: "Clean your hands often. Wash your hands often with soap and water for at least 20 seconds especially after you have been in a public place, or after blowing your nose, coughing, or sneezing. If soap and water are not readily available, use a hand sanitizer that contains at least 60% alcohol. Cover all surfaces of your hands and rub them together until they feel dry. Avoid touching your eyes, nose, and mouth with unwashed hands. Avoid close contact, especially with people who are sick. Put distance between yourself and other people if COVID-19 is spreading in your community. This is especially important for people who are at higher risk of getting very sick." Other notifications may include, for example, identification of symptoms, what to do if a user thinks they are sick, how to prepare their family and resources, etc.

The pandemic response module in step 806 may collect user physiological data and localization data from a plurality of wearable devices (e.g. the wearable device 302 associated with user 336, wearable devices associated with the crowd of users 338), where the physiological data may include sensor data (e.g., from any of the sensors 316-328) and localization data (e.g., from GPS unit 330, UWB unit 332, audio sensors 326, etc.) Such analysis may include determining portions of such data associated with the pandemic (e.g., portions of the physiological data, location data, colocation data for multiple users, user specific risk as calculated by one or more the modules 354-364, etc.). In some embodiments, the pandemic response module may analyze a user's physiological data related to body temperature and respiration (e.g., two symptoms of the disease caused by COVID-19), in association with localization data, to determine which users may be at a greater risk. The risk associated with a first user, for example, may be based upon the amount of people collocated (e.g., as detected by GPS, UWB, ambient audio) with the user, and/or the physiological data of other users that the user may have interacted with.

In step 808, instructions are provided to users who may be at risk due to the pandemic (e.g., as determined by the analysis from step 806). Such instructions may include steps to take to avoid infection, indications of the risk factors, symptoms and testing information, situations to avoid, supplies to stock up on, health and safety resources available, etc. In some embodiments, users with a high risk of infection may be advised to receive disease testing based on their physiological and/or location data. The analysis from step 806 may also be used to provide instructions in step 808 to other users that a particular user has interacted with (e.g., recommendations to perform testing). Such instructions may, in some embodiments, advantageously not identify or violate the privacy of the user.

Notifications may also be provided to one or more third parties in step 810 using one or more of the third-party networks 368 (e.g., first responders networks 370, essential workforce networks 372, local caregiver networks 374, hospital networks 376, state and local health networks 378, federal health networks 380, world health networks 382, etc.). Such notifications may include, for example, information regarding at-risk users for a particular pandemic (e.g., COVID-19). The first responders networks 370, as an example, may use such notifications to make contact with the at-risk users and discuss further treatment. As another example, the state and local health networks 378, the federal health networks 380 and/or the world health networks 382 may use the information to improve models and forecasting of the spread of a contagious disease (e.g., COVID-19). The pandemic response module 352 may continuously update the database 366 with relevant pandemic data in step 812. The pandemic data may include, but is not limited to, pandemic instructions, security protocols, government advisements, predictions and assessments of current cases, etc. The pandemic data may change rapidly, and other modules of the AI wearable device network 348 (e.g., any of modules 350-364) may run their respective algorithms repetitively with various parameters and modifications based on the pandemic data that is continuously updated in the database 366.

In step 814, historical physiological data is retrieved from the database 366. The data may be associated with the crowd of users 338 and include large amounts of collected data over a significant amount of time. In some embodiments, the historical physiological data is associated with hundreds of thousands or millions of users in various parts of the world, such that international pandemic data may be tracked and monitored with a standardized system. The pandemic response module 352 generates at least one pandemic model in step 816 based on the historical physiological data retrieved in step 814. The pandemic model, for example, may be used to forecast virus transmission amount and rate based on automatic contact tracing data (e.g., as provided by the automated contact tracing module 358). In some embodiments, the pandemic model comprises a metapopulation model based on a global network of local populations (e.g., city-level populations) providing physiological data and localization data to the AI wearable device network 348. In one type of analysis, users may be nodes connected by edges which represent travel between cities (e.g., air passenger travel). At each node of the network, the model may describe outbreak dynamic using a discrete-time Susceptible-Exposed-Infected-Recovered (SEIR) compartmental model, such as that described by Lauren Gardner at the Johns Hopkins University (JHU) Center for Systems Science and Engineering (CSSE) in collaboration with Aleksa Zlojutro and David Rey at the Research Centre for Integrated Transport Innovation (rCITI) at the University of New South Wales (UNSW) Sydney, and Ensheng Dong at the JHU CSSE. In some embodiments, physiological and localization data volumes for various travel routes connecting airport pairs, including stopovers, may be used to construct weighted edges. The model results may be based on an average of running several scenarios (e.g., 250 runs). The pandemic model generated in step 816 may be compared with and updated based on comparison with other pandemic models (e.g., which may have been generated using other iterations of the step 816). In step 818, the pandemic response module 352 updates user notifications, one or more of the third-party networks 368, other software module algorithms of the AI wearable device network 348 (e.g., any combination of modules 350-364) or combinations thereof based on the at least one pandemic model generated in step 816. This may include, for example, updating users who are traveling with their associated disease import risk, updating users of cities with hub airports of their associated risk associated with disease import, etc.

Figure 9:
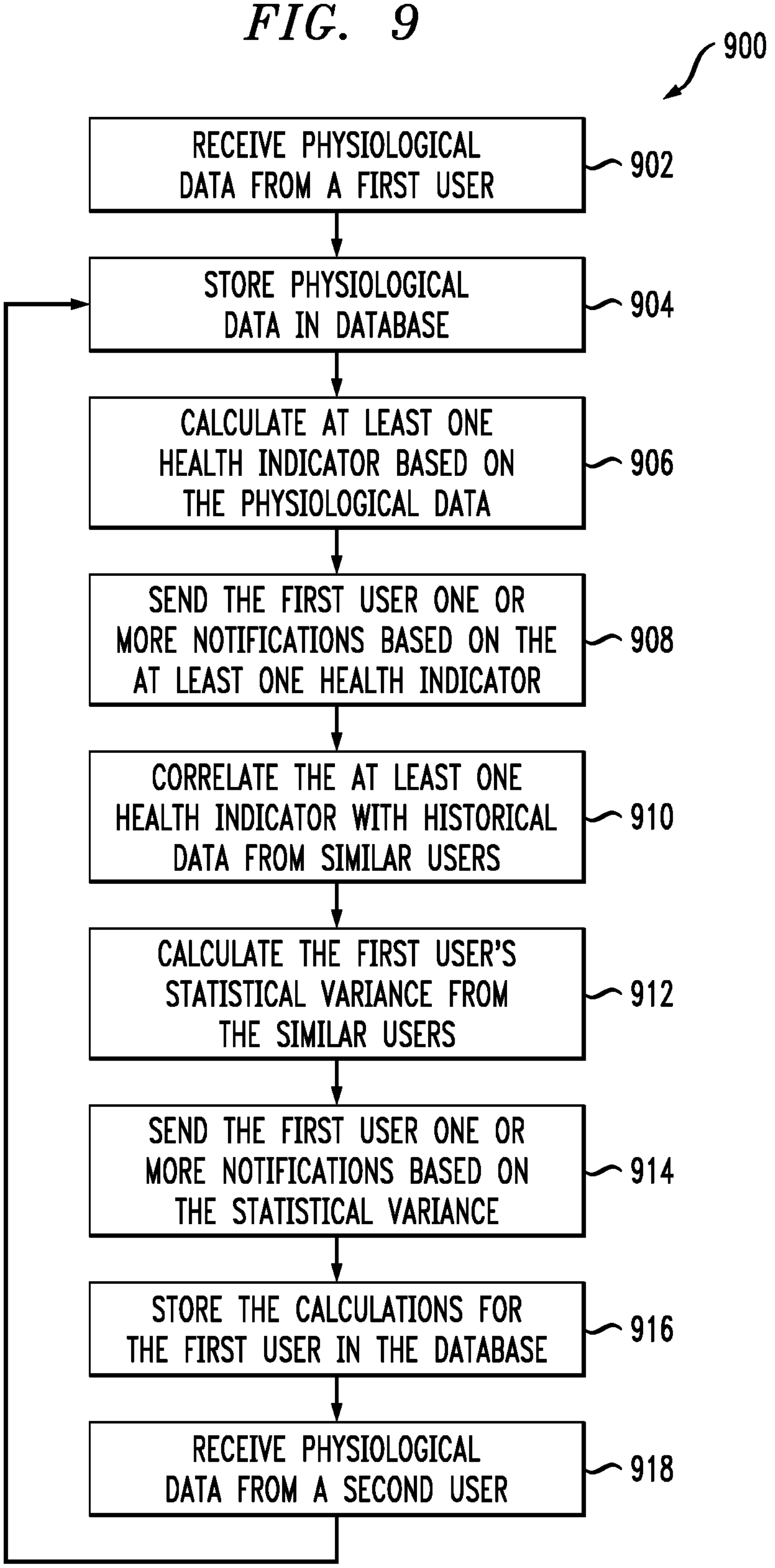
FIG. 9 illustrates a process flow for operation of the vital monitoring module of the artificial intelligence wearable device network in the FIG. 3 system, according to an embodiment of the invention.

Functionality of the vital monitoring module 354 of the AI wearable device network 348 will now be described in further detail with respect to the process flow 900 of FIG. 9. The process 900 begins in step 902 with receiving physiological data (e.g., sensor data from the sensing unit 314 of wearable device 302 or metrics derived therefrom, user profile data 344 for the user 336, etc.) from a first user (e.g., the user 336) via network 384. The received physiological data may be raw sensor data from any combination of the temperature sensors 316, heart rate sensors 318, respiration sensors 320, pulse oximetry sensors 322, accelerometer sensors 324, audio sensors 326 or other sensors 328, or various metrics or preliminary analysis derived therefrom (e.g., deriving breath rate from bioimpedance data). The received physiological data is stored in the database 366 in step 904. In some embodiments, the physiological data is stored in association with the user 336. In other embodiments, at least portions of the physiological data is anonymized for user privacy and security based on security settings of the user 336 and/or security protocols associated with one or more of the third-party networks 368.

In step 906, at least one health indicator (e.g., heart rate variability, body temperature, breath rate and/or depth, risk of disease, etc.) is calculated based on the physiological data and possibly one or more health indicators from wearable sensors or devices used in medical sciences, sports and security. Wearable sensors and devices can detect abnormal and unforeseen situations, and monitor physiological parameters and symptoms through such data. In some embodiments, the vital monitoring module 354 provides technology for transforming health care by allowing continuous monitoring of patients (e.g., user 336 and crowd of users 338) without hospitalization. Medical monitoring of physiological parameters including but not limited to user body temperature, heart rate, brain activity, muscle motion, and other critical data can be delivered through analysis of the data. Moreover, in sports training there is an increasing demand for health indicators that are associated with wearable sensors. For example, measurement of sweat rate was possible only in laboratory-based systems a few years ago, but is now possible through the use of wearable sensors in any desired location.

In some embodiments, step 906 advantageously calculates health indicators such as rate of respiration or breath rate. A user's respiratory rate may represent the number of breaths taken per minute. The normal respiration rate for an adult human at rest is 12 to 20 breaths per minute. A respiration rate under 12 or over 25 breaths per minute while resting is considered abnormal. Among the conditions that can change a normal respiratory rate are asthma, anxiety, pneumonia, congestive heart failure, lung disease, use of narcotics, drug overdose, etc. Notably, one symptom of COVID-19 is shortness of breath, including shortness of breath combined or associated with fever and/or fatigue.

Notifications are sent in step 908 to the users (e.g., user 336 and crowd of users 338) based on the health indicators calculated in step 906. The notification may include, for example, text, a graphic display, statistics, data visualizations (e.g., in a Cartesian or polar coordinate graph), etc. In step 910, the health indicators associated with one user are correlated with historical data from other similar users (e.g., where similar users share some common characteristics, such as one or more of age, weight, sex, etc.). The correlation, in some embodiments, is based on correlating at least two time segments. Time segments may be considered correlated if their associated correlation coefficient is above some designated threshold (e.g., 95%). If the vital monitoring module 354 determines that two segments are correlated, they may be marked as repetitive. It should be noted that time segments are repetitive with respect to each other, meaning that one time segment may be marked repetitive multiple times. For example, consider time segments one, two, three and four. Time segment one may be marked as repetitive to time segments two and four, but not time segment three. Combinations of time segments (e.g., pairs of time segments) may also be marked as repetitive (e.g., time segments one and two are repetitive, time segments one and three are not repetitive, etc.).

In step 912, the statistical variance is calculated between a first user (e.g., user 336) and correlated similar users (e.g., one or more of the crowd of users 338) determined in step 910. Step 912 may include calculating any other relevant statistical analysis metric in addition to or in place of statistical variance. Examples of other statistical analysis metrics that may be calculated include a coefficient of correlation, an R-squared value, a p-value, etc. The statistical variance or other statistical analysis metrics may be used to determine, for instance, if the user 336 is experiencing severe symptoms as compared to global, national, regional or other network-level correlations. In such embodiments, users experiencing abnormally severe symptoms may receive expedited treatment (e.g., advanced in triage, provided special instructions for treatment of symptoms and/or mitigation of infection spread). Notifications are sent to the users in step 914 based on the calculated statistical variance. Such notifications, for example, may alert a user (e.g., user 336) of risk of infectious disease based on correlated sensor data indicating that the respiratory rate of the user is determined to have increased from previous measurements and in comparison with other users (e.g., one or more of the crowd of users 338). This may be an indicator of shortness of breath, a symptom associated with, for example, COVID-19.

Results of one or more of the calculations of the process 900 (e.g., the health indicators calculated in step 906, correlated similar users calculated in step 910, statistical variance or other statistical analysis metrics between users calculated in step 912, etc.) are stored in the database 366 in step 916. The data stored in the database 366 may be stored in association with a specific user, or may be anonymized for user privacy and security (e.g., using encryption algorithms selected based on the user's security settings or security protocols associated with one or more of the third-party networks 368).

In step 918, physiological data from a next (e.g., second) user is received. For example, in step 902 physiological data may be obtained from user 336, while step 918 may include obtaining physiological data from one of the crowd of users 338. Following step 918, the steps 904 through 916 may be repeated. It should be noted that step 918 (and subsequent iterations of steps 904 through 916) may be repeated for a plurality of users (e.g., multiple users in the crowd of users 338). Each of the plurality of users is assumed to provide sensor data that is obtained from one or more wearable devices configured to continuously monitor physiological parameters of the plurality of users. The physiological data may be used in conjunction with localization data of the plurality of users in order to determine risk of infection, symptoms of illness, and other critical determinations for monitoring the spread of diseases (e.g., disease outbreaks of an epidemic or global pandemic).

Figure 10:
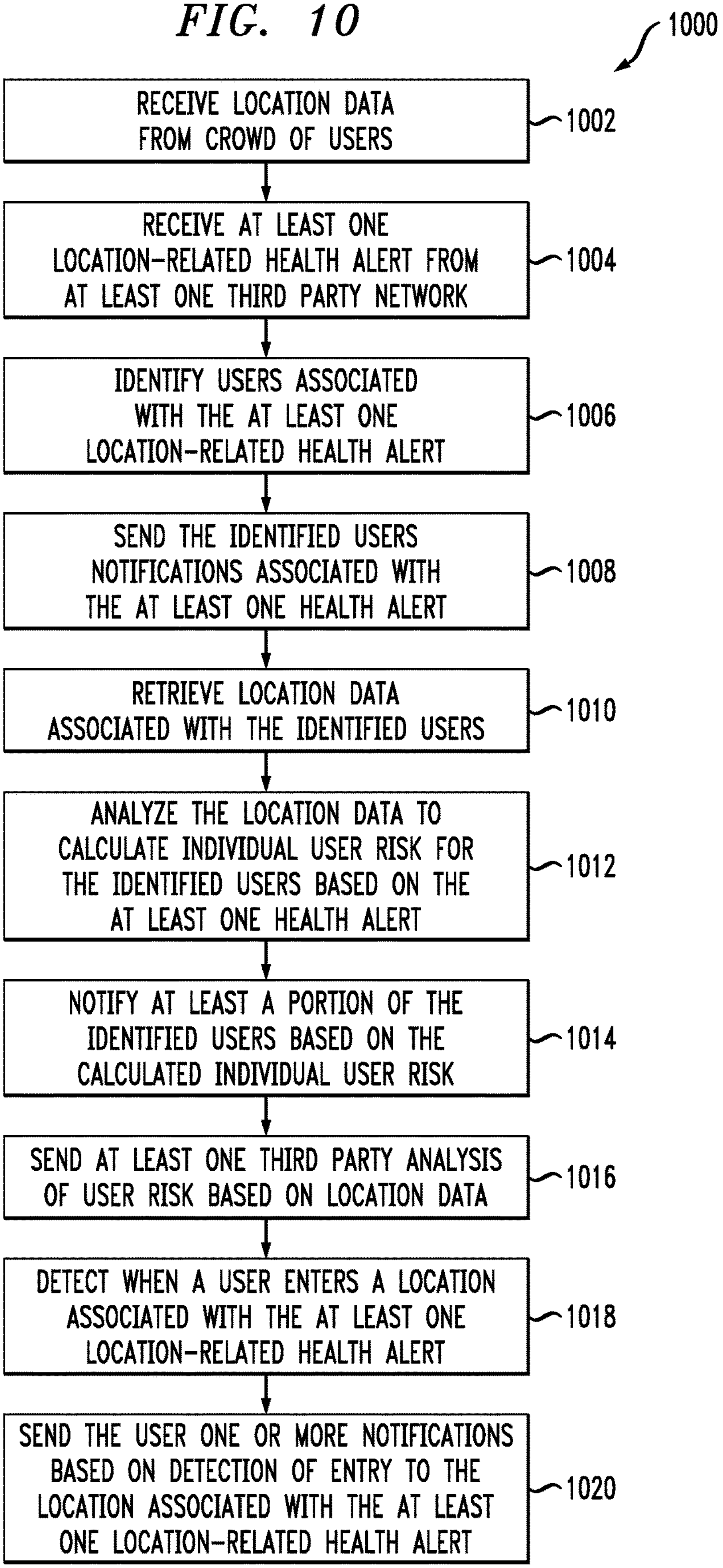
FIG. 10 illustrates a process flow for operation of the location tracking module of the artificial intelligence wearable device network in the FIG. 3 system, according to an embodiment of the invention.

Functionality of the location tracking module 356 of the AI wearable device network 348 will now be described in further detail with respect to the process flow 1000 of FIG. 10. The process 1000 begins in step 1002 with receiving location data from a plurality of patients or other users (e.g., user 336 and crowd of users 338), each providing sensor data obtained from one or more wearable devices. For example, sensor data is obtained for the user 336 from sensing unit 314 (e.g., any combination of sensors 316-328 thereof) of the wearable device 302. The sensor data provides continuous monitoring of physiological parameters that may be used in conjunction with localization data of the plurality of users obtained in step 1002 to determine risk of infections, symptoms of illness, and other critical determinations for monitoring the spread of diseases (e.g., associated with outbreak of an epidemic or global pandemic).

In step 1004, at least one location-related health alert is received from at least one of the third-party networks 368 (e.g., one or more of the first responder networks 370, essential workforce networks 372, local caregiver networks 374, hospital networks 376, state and local health networks 378, federal health networks 380 and world health networks 382). Users associated with the at least one location-related health alert are identified in step 1006. Location-related health alerts may be associated with alert networks such as, for example, the Health Alert Network (HAN) which contains public information for medical providers including but not limited to up-to-date health alert information, a document library on public health topics, etc. Some examples of location-related health alerts include: the closure of public transit; ordering people off the streets; rationing supplies; curfews imposed; streets closed to vehicles; etc. It should be noted that these are just a few examples of possible location-related health alerts, and that embodiments are not limited to these specific examples. Location-related health alerts may more generally include any information that relates to outbreak or potential outbreak of a disease in a particular location, and its effect on that location. Location-related health alerts may include information indicating whether quarantine, stay-at-home, social distancing or other self-isolation orders are in effect or recommended for users in a particular location.

Notifications associated with the location-related health alerts are provided to the identified users in step 1008. For example, a notification associated with at least one health alert may be: "A new coronavirus called COVID-19 was detected in New York City. This virus can cause a range of illnesses, from the common cold to pneumonia. You can get information and resources to stay healthy and informed during the pandemic. Text updates are available. Get the latest updates from Notify NYC by texting the word "COVID" to ###-###. Text "COVIDESP" to ###-### to receive the same updates in Spanish."

Location data for the identified users is retrieved in step 1010. The location data may include, for example, any combination of GPS, UWB and ambient audio sensor data. The location data is analyzed in step 1012 to calculate user individual risk based on the at least one health alert. Step 1012 may include, for example, determining colocation based on at least one source of localization data (e.g., GPS, UWB, ambient audio sensor data, combinations thereof, etc.). At least a portion of the identified users (e.g., those having calculated user individual risk over some threshold) are sent notifications in step 1014. Such a notification, for example, may be: "Based on your location (New York City) and your age, you may be at risk for coronavirus disease (COVID-19). Please practice social distancing and contact ###-#### for more information."

In step 1016, at least one third party is sent analysis of the user risk based on the location data. The third party may be associated with one or more of the third-party networks 368 (e.g., one or more of the first responder networks 370, essential workforce networks 372, local caregiver networks 374, hospital networks 376, state and local health networks 378, federal health networks 380 and world health networks 382). In some embodiments, one or more of the third-party networks 368 collects voluntary information about user experience with a disease that is associated with an outbreak, epidemic or pandemic (e.g., user experience with COVID-19) to better understand the impact of the disease at various levels (e.g., city, state, country, world, etc.). The third party may be provided with, for example, data associated with the users experiencing symptoms (e.g., coughing, fever, shortness of breath) of the disease, data associated with users who have been exposed to the disease (e.g., COVID-19) or who came in contact with someone who is infected, users who have tested positive for the disease, users who were, are or will be placed under mandatory or voluntary quarantine or self-isolation, etc. In some cases, users provide information for themselves as well as children or other family members if authorized to do so. The information collected by the third party in step 1016 may be used to follow up about users' disease inquiries and to make sure that the users are appropriately connected to the relevant ones of the third-party networks 368 (e.g., a State Department of Health associated with one or more state and local health networks 378). In some embodiments, data provided in step 1016 helps the third parties get users the support and care they may need (e.g., such as if a user decides to voluntarily self-isolate as a precaution).

In some embodiments, the process 1000 includes detecting when a user enters a location associated with at least one health alert in step 1018. This may include, for example, travel alerts such as: "Refrain from non-essential domestic travel for 14 days. This advisory does not apply to employees of critical infrastructure industries, including but not limited to trucking, public health professionals, financial services, and food supply." In step 1020, users are sent notifications based on detection of entry to a location associated with at least one health alert in step 1018. The notifications sent in step 1020 may include, for example, detected symptoms, risk of exposure to other people based on colocalization, quantitative analysis of user physiological and localization data, qualitative information provided by one or more of the third-party networks 368 (e.g., such as a local government associated with one of the state and local health networks 378 that provides specific messages such as "The City has enacted public health social distancing restrictions to reduce the spread of the COVID-19 virus. Social distancing restrictions include: (1) keeping six feet away from others (non-family group members); (2) not engaging in team sports; (3) not gathering in groups; (4) non-essential businesses should be closed; and (5) essential businesses that are open must follow necessary restrictions").

Figure 11:
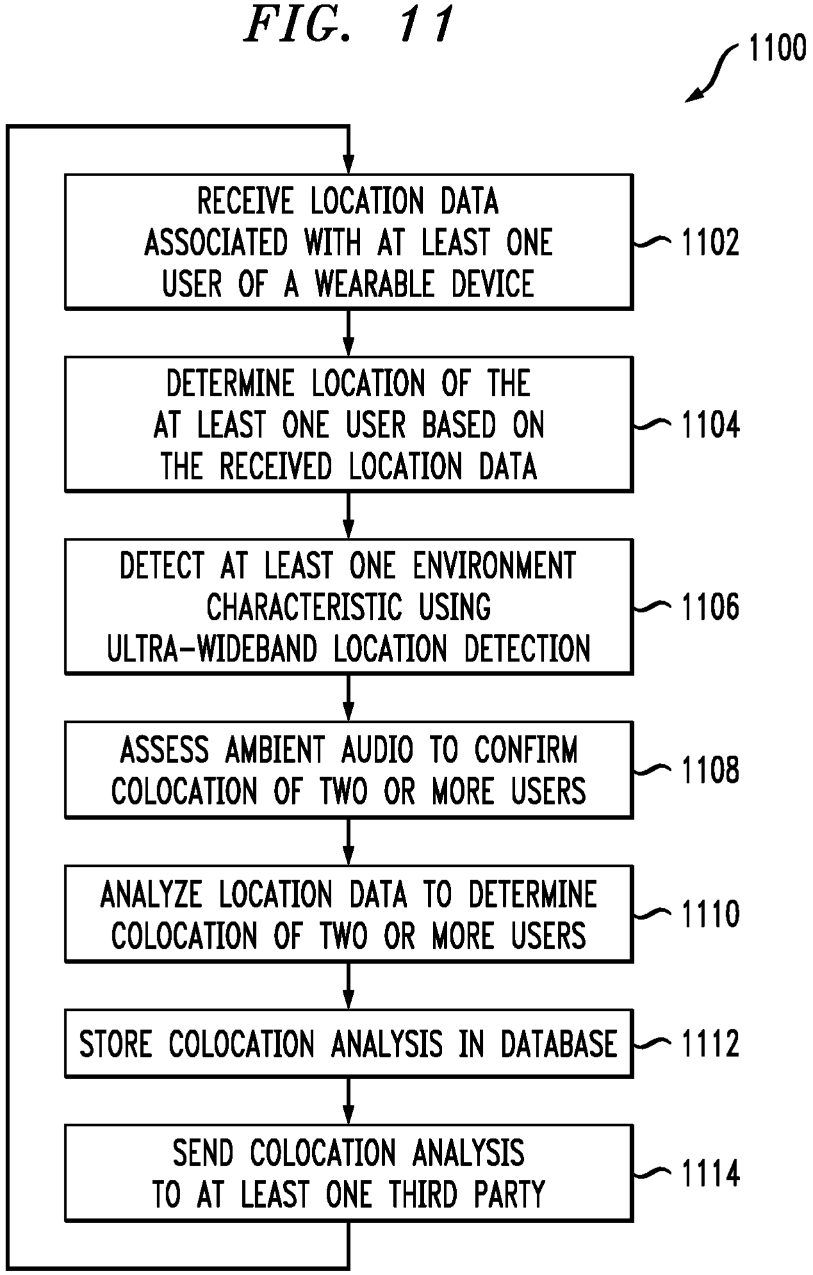
FIG. 11 illustrates a process flow for operation of the automated contact tracing module of the artificial intelligence wearable device network in the FIG. 3 system, according to an embodiment of the invention.

Functionality of the automated contact tracing module 358 of the AI wearable device network 348 will now be described in further detail with respect to the process flow 1100 of FIG. 11. The process 1100 begins in step 1102 with receiving location data (e.g., GPS, UWB, ambient audio, etc.) associated with at least one user (e.g., user 336) of a wearable device (e.g., wearable device 302). In step 1104, a location of the at least one user is determined based on the location data received in step 1102. For example, GPS data may be used to provide approximate geographic location tracking of the at least one user. The approximate geographic location tracking may provide, as an example, the continent, country, state, county, city or town, specific street address, or specific Cartesian coordinates.

In step 1106, at least one environmental characteristic of the at least one user is determined based on the location data received in step 1102. For example, UWB data may be used to provide highly localized tracking. This may include determining whether a user is indoors or outdoors, determining if there are other users nearby, determining how crowded an area is, etc. UWB signals may be used in various applications, including interference mitigation, location awareness, and in a "spatial rake" receiver system. UWB positioning or locating systems utilize UWB to determine both range and bearing using a significantly smaller aperture than traditional time difference of arrival (TDOA) Angle of Arrival (AoA) systems require. Whereas traditional TDOA AoA systems may require two antennas separated by several feet, illustrative embodiments utilize UWB which allows an aperture no larger than a single antenna to make an AoA measurement. Knowing the time of flight of a direct signal allows calculation of the range between a transmitter and a receiver. If a receiver also measures an angle of arrival, then both range and bearing follow. Unlike traditional UWB location systems that rely on multilateration from a collection of ranges, modern systems enable a localized location awareness that allows an individual receiver to locate a transmitter without requiring a complicated network of receivers to collect, share, and analyze range data.

In step 1108, colocation of two or more users is assessed based on the location data received in step 1102. For example, ambient audio data may be used to confirm the colocation of multiple users. Ambient audio may be used to extract information about the environment based on the ambient audio detected in the user's environment. Ambient audio, may indicate, for example the presence of other voices in the area, large crowds of people, traffic patterns, etc.

The combination of information and analysis of the location data received in step 1102 from steps 1104, 1106 and 1108 is used to determine colocation of two or more users in step 1110. Analyzing location data to determine collocation of individuals, in some embodiments, includes determining collocation of individuals over a certain threshold (e.g., 8 people). Collocation may be first determined by a first sensor (e.g., GPS) and then verified with other sensors (e.g., UWB and ambient audio). In some embodiments, contextual awareness adjust the collocation algorithm, (e.g., for users determined to live in the same geographic location such as a large apartment building, other sensors such as UWB and ambient audio may be relied on for collocation since users may be in the same geographic location but not collocated within the same unit).

The colocation analysis from step 1110 is stored in the database 366 in step 1112. The colocation analysis, in some embodiments, is stored in the database 366 in association with a specific user. In other embodiments, the colocation analysis is anonymized for user privacy and security before storage in the database 366. As an example, an encryption algorithm may be selected based on a user's security settings, or security protocols in association with one or more of the third-party networks 368. The colocation analysis is sent to at least one third party via one or more of the third-party networks 368 in step 1114. In some embodiments, the automated contact tracing module 358 and process 1100 are utilized for preventing pre-symptomatic transmission of a highly infectious disease (e.g., coronavirus 2019-nCoV/COVID-19) such that a user may be collocated with a large number of individuals who may or may not transmit pathogens to the user. This may include sending alerts or other notifications to users before such users enter or are predicted to enter high risk areas, such as a nursing home. Nursing homes have been epicenters of COVID-19 disease fatalities, as the disease appears to disproportionately affect persons over the age of 70. In some embodiments, one or more of the third-party networks 368 receive notice of users whose location data indicates colocation with a large number of people, and reach out to those users to provide telemedical treatment as opposed to in-person treatment which may expose other patients and caregivers to the infectious disease. In some embodiments, the data may be used to prevent further spread of the infectious disease to high risk areas by taking special precautions such as eliminating visitation from users who have data indicting widespread colocation with a large number of people. The process 1100 then loops back to step 1102.

Figure 12:
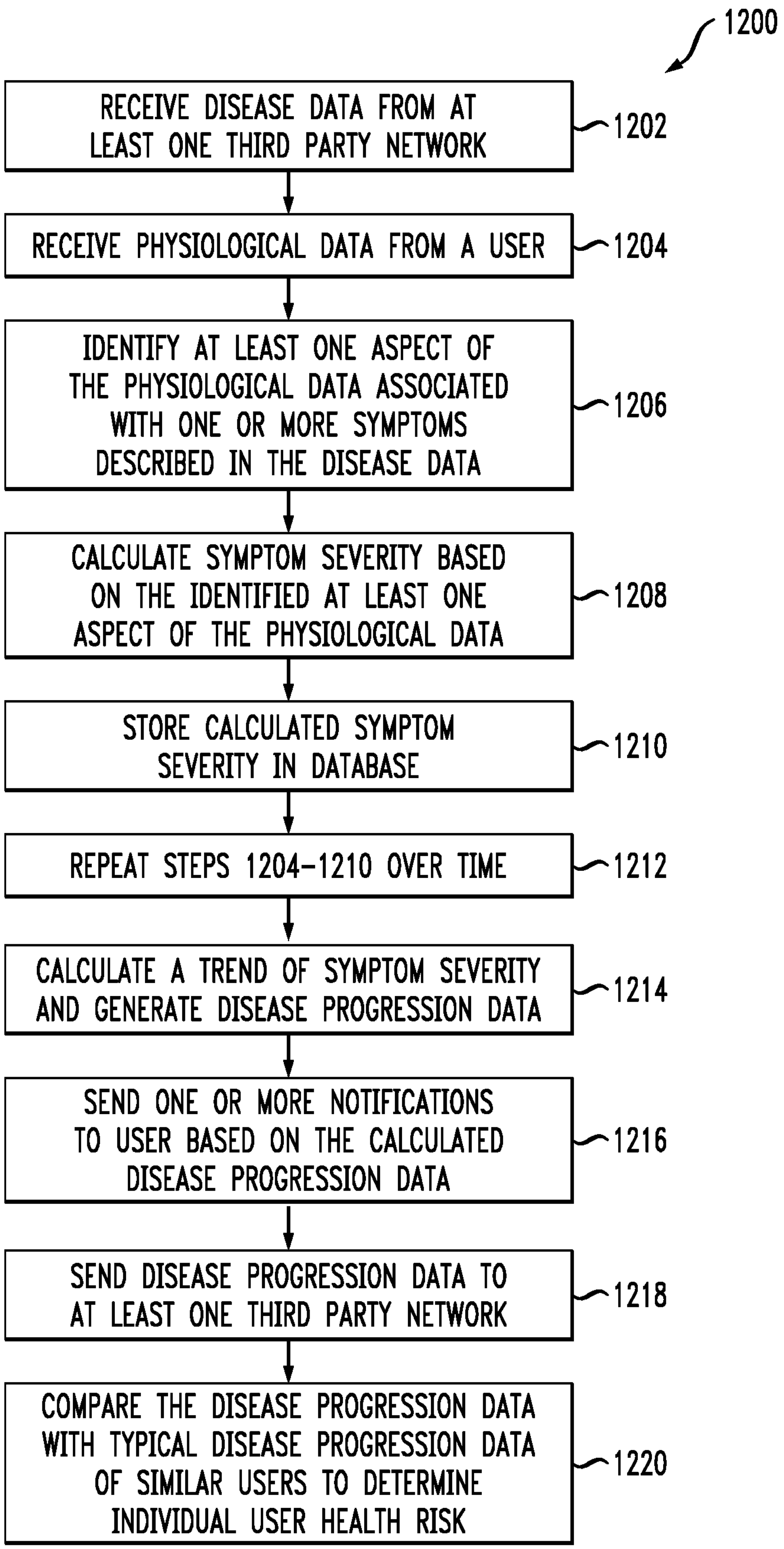
FIG. 12 illustrates a process flow for operation of the disease progression module of the artificial intelligence wearable device network in the FIG. 3 system, according to an embodiment of the invention.
Figure 13:
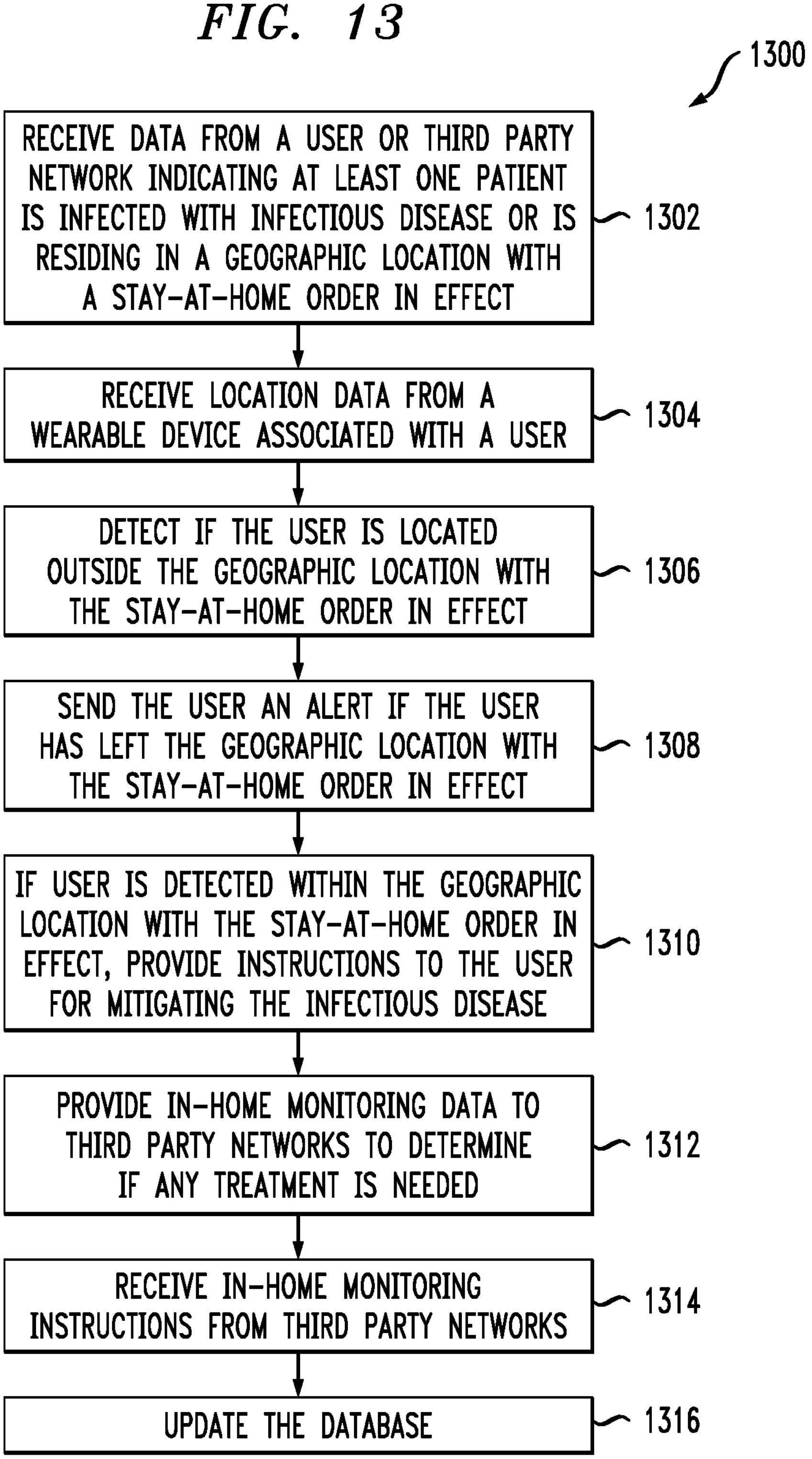
FIG. 13 illustrates a process flow for operation of the in-home module of the artificial intelligence wearable device network in the FIG. 3 system, according to an embodiment of the invention.

Functionality of the disease progression module 360 of the AI wearable device network 348 will now be described in further detail with respect to the process flow 1200 of FIG. 12. The process 1200 begins in step 1202 with receiving disease data from at least one of the third-party networks 368. In some embodiments, the disease data includes information regarding diseases associated with epidemic or pandemic conditions, such as COVID-19. The received data may include, for example, progression symptoms such as data associated with users who may be sick with an infectious disease for 1 to 14 days before developing symptoms. The data may further provide the most common symptoms of the infectious disease (e.g., for COVID-19, the most common symptoms are fever, tiredness, and dry cough). In some embodiments, the data may be associated with recovery of users (e.g., about 80% of users may recover from the infectious disease without needing special treatment). In some embodiments, the disease progression data may be associated with diseases that can be serious and even fatal. For some infectious diseases, older people and people with other medical conditions (e.g., asthma, diabetes, heart disease, etc.) may be more vulnerable to becoming severely ill and are thus provided with different disease progression algorithms (e.g., different thresholds, alerts or notifications, etc.). The disease progression module 360 may provide functionality for tracking common symptoms that users may experience, such as cough, fever, tiredness, difficulty breathing in severe cases, etc. The disease progression module 360 may utilize this symptom tracking functionality for informing one or more of the third-party networks 368 (e.g., first responder networks 370, local caregiver networks 374, etc.) to provide enhanced capacity for triage, prediction and diagnosis by analysis of continuous wearable sensor data. In some embodiments, the disease data may be provided by one or more of the third-party networks 368 providing services to users in response to an epidemic, global pandemic or other outbreak of an infectious disease. The third-party networks 368 may provide disease data that indicates the disease progression (e.g., progression of symptoms associated with the disease) to the AI wearable device network 348.

In step 1204, physiological monitoring data is received from a user (e.g., user 336). The physiological monitoring data may include information obtained from the sensing unit 314 using one or more of the sensors 316-328. The received physiological monitoring data may be raw sensor data, or data or metrics derived from the raw sensor data (e.g., a breath rate derived from bioimpedance data). In step 1206, at least one aspect of the physiological data received in step 1204 that is associated with one or more symptoms described in the disease data received in step 1202 is identified. As noted above, the disease progression module 360 may provide functionality for tracking common symptoms of an infectious disease. The sensing unit 314 of wearable device 302 may use one or more of the sensors 316-328 to quantitatively detect and track severity of a variety of disease symptoms including fever, coughing, sneezing, vomiting, infirmity, tremor, and dizziness, as well as signs of decreased physical performance and changes in respiratory rate/depth in the user 336. Blood oxygenation (e.g., using pulse oximetry) may also be monitored.

Symptom severity is calculated in step 1208 based on the at least one aspect of the physiological monitoring data identified in step 1206. The symptom severity may also be calculated or determined based on qualitative data submitted by a user (e.g., some users may have aches and pains, nasal congestion, runny nose, sore throat, diarrhea, etc., which may be monitored and used for calculating symptom severity). The sensor data may be used to quantitatively assess physiological monitoring symptoms, which thereby prompts a user interaction sequence wherein the user is able to qualitatively evaluate physical health, emotional mood, energy level, pain level, etc., such that data may be used in combination with the quantitative sensor data to determine symptom severity. For example, a user's body temperature may be assessed to be approximately 103 degrees Fahrenheit, indicating a fever. Further, the user's physiological monitoring data may indicate decreased movement and activity, indicating fatigue. The user may input qualitative data, such as "having trouble breathing/shortness of breath." Such qualitative data may be used in Natural Language Processing (NLP) calculations for determining if the user's input indicates severe or mild symptoms. In some embodiments, the disease progression module 360 may request the user to input symptom severity for qualitative data (e.g., "On a scale from 1-10, 10 being the worst, how bad was the shortness of breath?").

The calculated symptom severity is stored in the database 366 in step 1210. The symptom severity may be stored in association with a specific user, or may be anonymized for user privacy and security such as using encryption algorithms selected based on the user's security settings or security protocols in associated with one or more of the third-party networks 368. In step 1212, the processing of steps 1204-1210 is repeated over time (e.g., for the same user 336 based on new physiological data received therefrom, for a group of users such as crowd of users 338, etc.). This enables calculation of trends of symptom severity in step 1214 to generate disease progression data (e.g., the change in appearance and severity of various symptoms over time). In some embodiments, this includes detecting or predicting the user's period of recovery to aid in self-isolation efforts. The user may be prompted to compare qualitative aspects of symptoms with qualitative recollection of previous symptoms (e.g., "Has the user's cough improved or worsened since the previous day?"). Calculating the trend of symptom severity and generating disease progression data may include providing the user with alerts or other notifications indicating if symptoms are worsening (e.g., peak symptoms may still be to come), or if the symptoms are lessening (e.g., peak symptoms have passed, user is recovering).

Notifications are sent to the users based on the disease progression data calculated in step 1216. The notifications may include, for example, instructions for self-isolation (e.g., "Regularly and thoroughly clean your hands with an alcohol-based hand rub or wash them with soap and water. Maintain at least 1 meter (3 feet) distance between yourself and anyone who is coughing or sneezing. Avoid touching eyes, nose and mouth. Make sure you, and the people around you, follow good respiratory hygiene. This means covering your mouth and nose with your bent elbow or tissue when you cough or sneeze. Then dispose of the used tissue immediately. Stay home if you feel unwell. If you have a fever, cough and difficulty breathing, seek medical attention and call in advance. Follow the directions of your local health authority."). In some embodiments, the notifications may be customized based on the third-party networks 368 associated with the users. For example, the notifications may be customized based on the third-party networks 368 associated with the users. The notifications may instruct the users to initiate telemedical appointments in response to noticing the onset of any disease-related symptoms.

The disease progression data is also sent to one or more of the third-party networks 368 in step 1218. In some embodiments, the disease progression data for one user (e.g., user 336) is compared with the disease progression data for other users (e.g., users in the crowd of users 338 determined to be similar to user 336 based on age, sex, height, weight, known health risks, etc.) in step 1220. Based on this, the individual user health risk of user 336 may be determined (e.g., based on variance from a correlation model). Disease progression data can be made wirelessly available to one or more of the third-party networks 368 to amplify the decision-making capabilities of small care teams, enabling them to manage and direct critical care resources to a large number of dispersed patients at once. This enhanced capability allows health care leaders to organize efficiently, optimizing the allocation of resources around high-need patients.

Among other applications, illustrative embodiments deploy a wearable device data distribution system 300 for rapid, safe observation of individuals during periods of high load on a health care system, such as epidemics, pandemics and other disease outbreaks. In some embodiments, the disease progression data may be compared with typical disease progression data for similar users (e.g., based on age, sex, height, weight, known health risks, etc.) to determine individual user health risk which may be, for example, variance from a correlation model. The correlation may be based on correlating at least two time segments, and time segments may be considered correlated if the correlation coefficient is above some designated threshold (e.g., 95%). The correlated data may be used to determine if, for example, a particular patient is experiencing outlier symptoms for their demographic group. Such analysis may include providing one or more of the third-party networks 368 the capability of determining the allocation of resources to serve the needs of outlier patients.

Functionality of the in-home module 362 of the AI wearable device network 348 will now be described in further detail with respect to the process flow 1300 of FIG.

13. The process 1300 begins in step 1302 with receiving data from a user (e.g., user 336) or one of the third-party networks 368 indicating that the user 336 is infected with an infectious disease (e.g., which requires quarantine, social distancing, or self-isolation at home). The third-party networks 368 may send data to the AI wearable device network 348 indicating at least one patient (e.g., user 336) is infected with an infectious disease. The third-party networks 368, for example, may provide diagnosis or provide test results that relate to patient infection status. In other embodiments, users may self-report infection.

Location data (e.g., GPS, UWB, ambient audio, etc.) from the wearable device 302 associated with the user 336 is received in step 1304 via the networks 384 (e.g., one or more clouds). In some embodiments, analysis from the location tracking module 356 and/or automated contact tracing module 358 is utilized to determine collocation of large groups of people (e.g., 8 people). Collocation may be first determined by a first sensor (e.g., GPS) and then verified with other sensors (e.g., UWB and ambient audio). In some embodiments, contextual awareness is used to adjust the collocation algorithm (e.g., for users determined to live in the same geographic location such as a large apartment building, with other sensors such as UWB and ambient audio sensors being relied on for collocation since users may be in the same geographic location but collocated within the same unit).

Detection of whether the user 336 is located outside a quarantine or self-isolation location (e.g., a geographic location with a stay-at-home or other similar order in effect) is performed in step 1306. The quarantine or self-isolation location may be determined by the user 336, or by one or more of the third-party networks 368. The third-party networks 368, for example, may wish to detect if a user is outside of quarantine or self-isolation even if they are not infected because in viral pandemics such as COVID-19 infection may be especially dangerous for various individuals (e.g., the elderly or persons with respiratory disorders). The third-party networks 368, upon detection of the user's location outside of the quarantine or self-isolation location, may thereby provide alerts or other notifications or actions to ensure user safety (e.g., such as initiating a telemedical communication to direct the users back to safety).

In step 1308, one or more alerts or notifications are sent to the user 336 on detecting that the user 336 is located outside the quarantine or self-isolation location. If the user 336 is detected within the geographic location with the stay-at-home order in effect, instructions are provided to the user 336 in step 1310 for mitigating the infectious disease. The alerts or notifications may include, for example, text, graphics, statistics, government organizational information, emergency contacts, or other information. In some embodiments, the alerts or notifications may include the response by one or more of the third-party networks 368. If a user is detected within a quarantine or self-isolation location, instructions may optionally be provided to the user for mitigating the disease, such as "Regularly and thoroughly clean your hands with an alcohol-based hand rub or wash them with soap and water. Maintain at least 1 meter (3 feet) distance between yourself and anyone who is coughing or sneezing. Avoid touching eyes, nose and mouth. Make sure you, and the people around you, follow good respiratory hygiene. This means covering your mouth and nose with your bent elbow or tissue when you cough or sneeze. Then dispose of the used tissue immediately. Stay home if you feel unwell. If you have a fever, cough and difficulty breathing, seek medical attention and call in advance. Follow the directions of your local health authority." In other embodiments, users detected within quarantine or self-isolation location may have specific information provided to them from one or more of the third-party networks 368 associated with the user.

In step 1312, in-home monitoring data is provided to one or more of the third-party networks 368 to determine if any treatment of the user 336 is needed. Such treatment may include, for example, delivery of prescription medication, telemedical interview with a physician, emergency response systems, etc. In some embodiments, one or more of the third-party networks 368 may receive the in-home monitoring data for patients thereby obtaining real time physiological monitoring and/or location data from patients' wearable devices enabling provision of better care to individuals who are most at need.

In-home monitoring and/or treatment instructions are received from one or more of the third-party networks 368 in step 1314. Such monitoring and/or treatment instructions may be provided to the user 336, or to a local caregiver associated with the user 336. This may include receiving instructions associated with locating a wearable device (e.g., wearable device 302) on the body of a user (e.g., user 336) in a location that is advantageous for detecting symptoms of an infectious disease (e.g., placing sensors on the chest to detect cough, shortness of breath, etc.). The one or more third-party networks 368 may provide instructions for proper use of the wearable device and any other symptom monitoring protocol. The instructions may also direct users to confirm a series of tests that may or may not be associated with the wearable device in order to determine if emergency service is needed. In some embodiments, the in-home monitoring instructions may include updates to the algorithms used to assess users. For example, caregivers associated with one or more of the third-party networks 368 may choose to expand or contract the geographic area in which the user may travel before an alarm may be triggered. The size of the geographic area may depend, at least in part, on the users physiological monitoring data (e.g., disease symptoms) or location data (e.g., locations traveled to in the last 14 days, particularly locations associated with a higher risk of contracting an infectious diseases such as high-risk countries, buildings or other areas or events with large crowds or close contact between individuals, etc.).

The database 366 is updated in step 1316 with information regarding the location of the user 336 over time as well as the monitoring and/or treatment data for the user 336. Again, the data may be stored in associated with a specific user, or may be anonymized for user privacy and security such as using an encryption algorithm selected based on user security settings or security protocols associated with one or more of the third-party networks 368. The in-home module 362 may thereby provide functionality for one or more of the third-party networks 368 to continuously facilitate physiological monitoring of a plurality of users located remotely. This includes providing information (e.g., analysis of physiological monitoring data) and instructions to the users, and updating monitoring algorithms based on the provided instructions. The instructions may change based on global health events, such as a viral pandemic (e.g., COVID-19).

Figure 14:
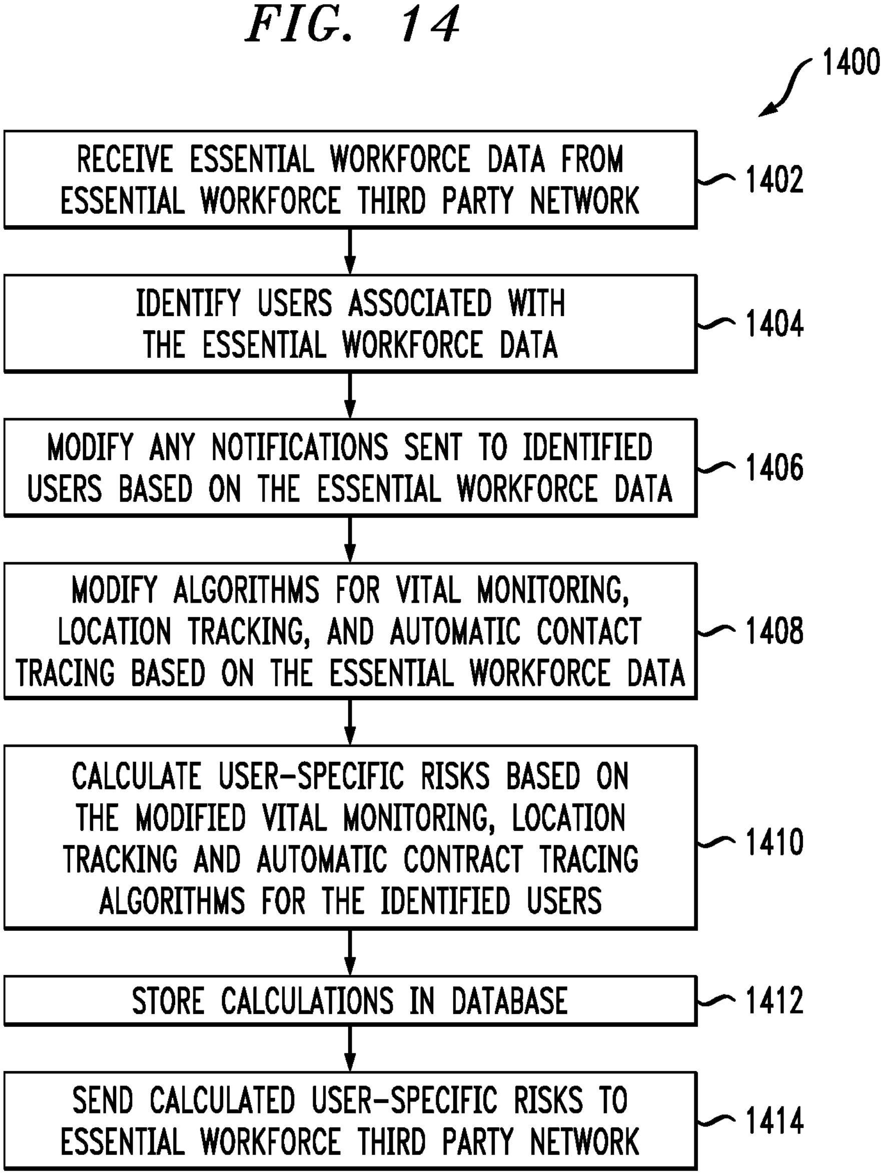
FIG. 14 illustrates a process flow for operation of the essential workforce module of the artificial intelligence wearable device network in the FIG. 3 system, according to an embodiment of the invention.

Functionality of the essential workforce module 364 of the AI wearable device network 348 will now be described in further detail with respect to the process flow 1400 of FIG. 14. The process 1400 begins in step 1402 with receiving essential workforce data from one or more of the essential workforce networks 372. Essential workforces may include, for example, users associated with industries and occupations for which continued operation is critical even during an epidemic, pandemic or other outbreak of an infectious disease. For example, in the U.S. the Department of Homeland Security (DHS) may define critical infrastructure industries such as health care services, pharmaceutical and food supply services, etc., that have a special responsibility to maintain a normal work schedule. Using the essential workforce data received in step 1402, users associated with essential workforces are identified in step 1404. Such users may include, for example, employees of companies in critical industries. Notifications from the in-home module 362 are modified in step 1406 based on the identified users associated with essential workforces. For example, such essential workforce users may not be sent alerts when leaving locations with stay-at-home orders. In step 1408, algorithms and processes of the vital monitoring module 354, location tracking module 356 and automated contact tracing module 358 may also be modified for the identified essential workforce users. In step 1410, user-specific risks (for the users identified in step 1404) are calculated based on the modified vital monitoring, location tracking and/or automatic contract tracing algorithms and processes implemented by the virtual monitoring module 354, the location tracking module 356 and the automated contact tracing module 358. Calculations from the process 1400 are stored in the database 366 in step 1412, and such calculations (e.g., of user-specific risks) are sent to one or more of the essential workforce networks 372 in step 1414.

In illustrative embodiments, a wearable sensor system (e.g., including the wearable device 302 of user 336 and wearable devices associated with the crowd of users 338) is used for widespread monitoring and modeling of global health data. The wearable devices in the wearable sensor system include various sensors (e.g., temperature, heart, respiratory sensors, etc.) along with communication modules and specialized software for producing global health related data analysis. Such analysis is provided from the wearable devices, possibly via wireless gateway devices, to a global health network (e.g., AI wearable device network 348) that performs global health analysis based on data received from the various wearable devices in the wearable sensor system. Global health analysis data may be communicated to various related entities (e.g., third-party networks 368). Such global health analysis may include, but is not limited to, determining pandemic response, monitoring user vitals, tracking location of users, performing automated contact tracing for users, determining disease progression, providing alerts and notifications for users staying at home or otherwise following social distancing or self-isolation orders, identifying essential workforces, etc.

Figure 15:
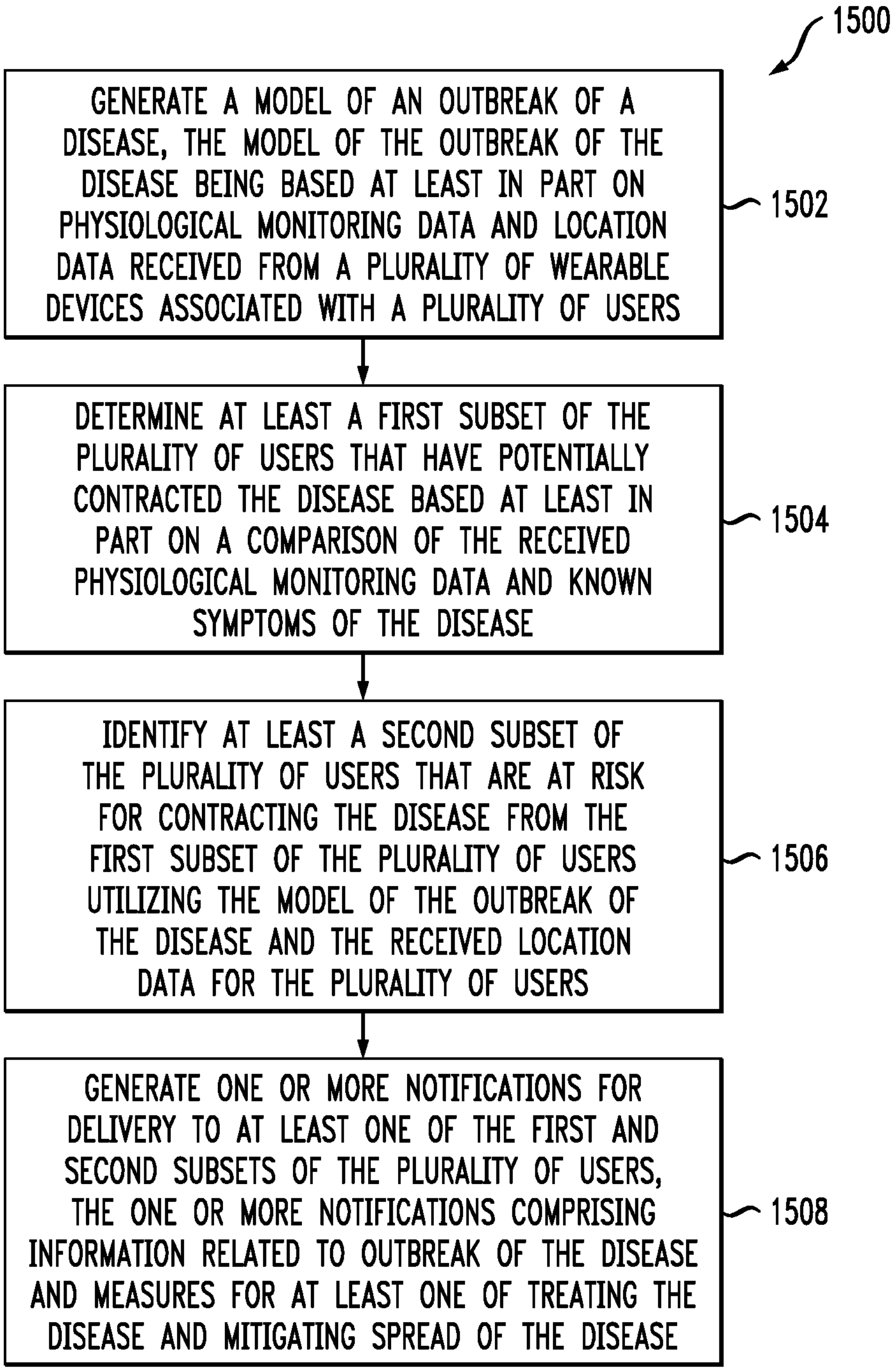
FIG. 15 is a flow diagram of an exemplary process for monitoring and modeling health data utilizing a wearable sensor system, according to an embodiment of the invention.

An exemplary process 1500 for monitoring and modeling health data using a wearable sensor system will now be described with reference to the flow diagram of FIG. 15. It should be understood, however, that this particular process is only an example and that other types of processes for monitoring and modeling health data using a wearable sensor system may be used in other embodiments as described elsewhere herein. The process 1500 includes steps 1502 through 1508, and is assumed to be performed by the AI wearable device network 348 of the wearable sensor system 300 (e.g., utilizing one or more of the modules 350-364 thereof). In some embodiments, at least a portion of the process 1500 may be performed by or using the wearable device 302.

The process 1500 begins with step 1502, generating a model of an outbreak of a disease. The model of the outbreak of the disease is based at least in part on physiological monitoring data and location data received from a plurality of wearable devices associated with a plurality of users.

In step 1504, at least a first subset of the plurality of users that have potentially contracted the disease are determined based at least in part on a comparison of the received physiological monitoring data and known symptoms of the disease.

In step 1506, at least a second subset of the plurality of users that are at risk for contracting the disease from the first subset of the plurality of users are identified utilizing the model of the outbreak of the disease and the received location data for the plurality of users.

In step 1508, one or more notifications are generated for delivery to at least one of the first and second subsets of the plurality of users. The one or more notifications comprise information related to outbreak of the disease and measures for at least one of treating the disease and mitigating spread of the disease.

The process 1500 may further include identifying at least a third subset of the plurality of users associated with one or more essential workforces. At least a given one of the one or more notifications generated in step 1508 may be modified prior to delivery of the given notification to users in the third subset of the plurality of users. At least a given one of the users in the third subset of users is also in one of the first subset of the plurality of users and the second subset of the plurality of users.

At least a given one of the one or more notifications generated in step 1508 may be delivered to at least a given one of the plurality of users responsive to determining that the given user is in a geographic location associated with the outbreak of the disease. The geographic location associated with the outbreak of the disease may comprise a geographic region where at least one of the users in the first subset of the plurality of users is known to have been present within a designated threshold period of time of when the physiological monitoring data for said at least one user is indicative of one or more of the known symptoms of the disease. The geographic location associated with the outbreak of the disease may comprise a geographic region where at least one of a quarantine, social distancing, stay-at-home and self-isolation order is in effect.

The process 1500 may further include providing information associated with the first subset of the plurality of users to one or more third parties responsible for monitoring the outbreak of the disease. The one or more third parties may comprise at least one of a local, state, federal and global health network. The information associated with the first subset of the plurality of users may comprise at least one of: the received physiological monitoring data for the first subset of the plurality of users; the received location data for the first subset of the plurality of users; and one or more health indicators derived from at least a portion of at least one of the received physiological monitoring data and the received location data for the first subset of the plurality of users. The information associated with the first subset of the plurality of users may be modified prior to being provided to the one or more third parties in accordance with data security rules regarding transfer of at least one of the received physiological monitoring data and the received location data of the first subset of the plurality of users. Modifying the information associated with the first subset of the plurality of users may comprise at least one of encrypting and anonymizing the information associated with the first subset of the plurality of users.

The process 1500 may further include providing information associated with the first subset of the plurality of users to one or more third parties responsible for providing care to the first subset of the plurality of users.

In some embodiments, step 1504 includes, for a given user in the first subset of the plurality of users: calculating one or more health indicators for the given user based on the received physiological monitoring data for the given user and a user profile of the given user; identifying one or more other users with user profiles exhibiting at least a threshold level of similarity to the user profile of the given user that are known to have the disease; and correlating the one or more health indicators for the given user with health indicators for the one or more other users utilizing one or more statistical measures.

At least a given one of the one or more notifications may be generated in step 1508 based at least in part on receiving one or more location-related health alerts from one or more third parties, and the process 1500 may further include delivering the given notification to at least a given one of the plurality of users responsive to detecting entry of the given user to a given geographic region associated with at least one of the one or more location-related health alerts.

Step 1506 may comprise determining colocation of at least a first user in the first subset of the plurality of users with at least a second user in the second subset of the plurality of users, wherein determining colocation is based at least in part on GPS information, UWB information and ambient audio information in the received location data for the first user and the second user.

Step 1500 may comprise updating the model of the outbreak of the disease based at least in part on trends of symptom severity for the known symptoms exhibited by the first subset of the plurality of users characterizing progression of the disease over time.

At least a given one of the one or more notifications is generated in step 1508 in response to receiving at least one of a quarantine, social distancing, stay-at-home and self-isolation order for one or more geographic regions, the given notification comprising instructions for following said at least one quarantine, social distancing, stay-at-home and self-isolation order based on the received physiological monitoring data for the plurality of users.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. An apparatus comprising:

at least one processing device comprising a processor coupled to a memory;

the at least one processing device being configured:

to generate a model of an outbreak of a disease, the model of the outbreak of the disease being based at least in part on physiological monitoring data and location data received from a plurality of wearable devices associated with a plurality of users;

to determine at least a first subset of the plurality of users that have potentially contracted the disease based at least in part on a comparison of the received physiological monitoring data and known symptoms of the disease;

to identify at least a second subset of the plurality of users that are at risk for contracting the disease from the first subset of the plurality of users utilizing the model of the outbreak of the disease and the received location data for the plurality of users; and to generate one or more notifications for delivery to at least one of the first and second subsets of the plurality of users, the one or more notifications comprising information related to outbreak of the disease and measures for at least one of treating the disease and mitigating spread of the disease;

wherein identifying the second subset of the plurality of users that are at risk for contracting the disease from the first subset of the plurality of users comprises:

determining colocation of at least a first user in the first subset of the plurality of users with at least a second user in the second subset of the plurality of users utilizing at least a first type of location data obtained from at least a first type of sensors of the plurality of wearable devices, the first type of location data comprising geographic location data and the first type of sensors comprising global positioning system (GPS) sensors;

determining one or more environmental characteristics of a local environment of geographic locations of the first user and the second user, the one or more environmental characteristics characterizing whether the first user and the second user are present at a given geographic location comprising a building with two or more units; and responsive to the determined one or more environmental characteristics indicating that the first user and the second user are present at the given geographic location, verifying colocation of the second user with the first user utilizing a second type of location data obtained from at least a second type of sensors of the plurality of wearable devices, the second type of location data comprising contextual location information for verifying presence of the second user and the first user within a common one of the two or more units of the building at the given geographic location.

2. The apparatus of claim 1, wherein the at least one processing device is further configured to identify at least a third subset of the plurality of users associated with one or more essential workforces.

3. The apparatus of claim 2, wherein the at least one processing device is further configured to modify at least a given one of the one or more notifications prior to delivering the given notification to users in the third subset of the plurality of users.

4. The apparatus of claim 2, wherein at least a given one of the users in the third subset of users is also in one of the first subset of the plurality of users and the second subset of the plurality of users.

5. The apparatus of claim 1, wherein the at least one processing device is further configured to deliver at least a given one of the one or more notifications to at least a given one of the plurality of users responsive to determining that the given user is in a geographic location associated with the outbreak of the disease.

6. The apparatus of claim 5, wherein the geographic location associated with the outbreak of the disease comprises a geographic region where at least one of the users in the first subset of the plurality of users is known to have been present within a designated threshold period of time of when the physiological monitoring data for said at least one user is indicative of one or more of the known symptoms of the disease.

7. The apparatus of claim 5, wherein the geographic location associated with the outbreak of the disease comprises a geographic region where at least one of a quarantine, social distancing, stay-at-home and self-isolation order is in effect.

8. The apparatus of claim 1, wherein the at least one processing device is further configured to provide information associated with the first subset of the plurality of users to one or more third parties responsible for monitoring the outbreak of the disease.

9. The apparatus of claim 8, wherein the one or more third parties comprise at least one of a local, state, federal and global health network.

10. The apparatus of claim 8, wherein the information associated with the first subset of the plurality of users comprises at least one of:

the received physiological monitoring data for the first subset of the plurality of users;

the received location data for the first subset of the plurality of users; and one or more health indicators derived from at least a portion of at least one of the received physiological monitoring data and the received location data for the first subset of the plurality of users.

11. The apparatus of claim 8, wherein the information associated with the first subset of the plurality of users is modified prior to being provided to the one or more third parties in accordance with data security rules regarding transfer of at least one of the received physiological monitoring data and the received location data of the first subset of the plurality of users.

12. The apparatus of claim 11, wherein modifying the information associated with the first subset of the plurality of users comprises at least one of encrypting and anonymizing the information associated with the first subset of the plurality of users.

13. The apparatus of claim 1, wherein the at least one processing device is further configured to provide information associated with the first subset of the plurality of users to one or more third parties responsible for providing care to the first subset of the plurality of users.

14. The apparatus of claim 1, wherein determining the first subset of the plurality of users that have potentially contracted the disease comprises, for a given user in the first subset of the plurality of users:

calculating one or more health indicators for the given user based on the received physiological monitoring data for the given user and a user profile of the given user;

identifying one or more other users with user profiles exhibiting at least a threshold level of similarity to the user profile of the given user that are known to have the disease; and correlating the one or more health indicators for the given user with health indicators for the one or more other users utilizing one or more statistical measures.

15. The apparatus of claim 1, wherein at least a given one of the one or more notifications is generated based at least in part on receiving one or more location-related health alerts from one or more third parties, and wherein the at least one processing device is further configured to deliver the given notification to at least a given one of the plurality of users responsive to detecting entry of the given user to a given geographic region associated with at least one of the one or more location-related health alerts.

16. The apparatus of claim 1, wherein the second type of location data comprises ultra-wideband information and ambient audio information.

17. The apparatus of claim 1, wherein generating the model of the outbreak of the disease comprises updating the model of the outbreak of the disease based at least in part on trends of symptom severity for the known symptoms exhibited by the first subset of the plurality of users characterizing progression of the disease over time.

18. The apparatus of claim 1, wherein at least a given one of the one or more notifications is generated in response to receiving at least one of a quarantine, social distancing, stay-at-home and self-isolation order for one or more geographic regions, the given notification comprising instructions for following said at least one quarantine, social distancing, stay-at-home and self-isolation order based on the received physiological monitoring data for the plurality of users.

19. A computer program product comprising a non-transitory processor-readable storage medium having stored therein executable program code which, when executed, causes at least one processing device:

to generate a model of an outbreak of a disease, the model of the outbreak of the disease being based at least in part on physiological monitoring data and location data received from a plurality of wearable devices associated with a plurality of users;

to determine at least a first subset of the plurality of users that have potentially contracted the disease based at least in part on a comparison of the received physiological monitoring data and known symptoms of the disease;

to identify at least a second subset of the plurality of users that are at risk for contracting the disease from the first subset of the plurality of users utilizing the model of the outbreak of the disease and the received location data for the plurality of users; and to generate one or more notifications for delivery to at least one of the first and second subsets of the plurality of users, the one or more notifications comprising information related to outbreak of the disease and measures for at least one of treating the disease and mitigating spread of the disease;

wherein identifying the second subset of the plurality of users that are at risk for contracting the disease from the first subset of the plurality of users comprises:

determining colocation of at least a first user in the first subset of the plurality of users with at least a second user in the second subset of the plurality of users utilizing at least a first type of location data obtained from at least a first type of sensors of the plurality of wearable devices, the first type of location data comprising geographic location data and the first type of sensors comprising global positioning system (GPS) sensors;

determining one or more environmental characteristics of a local environment of geographic locations of the first user and the second user, the one or more environmental characteristics characterizing whether the first user and the second user are present at a given geographic location comprising a building with two or more units; and responsive to the determined one or more environmental characteristics indicating that the first user and the second user are present at the given geographic location, verifying colocation of the second user with the first user utilizing a second type of location data obtained from at least a second type of sensors of the plurality of wearable devices, the second type of location data comprising contextual location information for verifying presence of the second user and the first user within a common one of the two or more units of the building at the given geographic location.

20. A method comprising:

generating a model of an outbreak of a disease, the model of the outbreak of the disease being based at least in part on physiological monitoring data and location data received from a plurality of wearable devices associated with a plurality of users;

determining at least a first subset of the plurality of users that have potentially contracted the disease based at least in part on a comparison of the received physiological monitoring data and known symptoms of the disease;

identifying at least a second subset of the plurality of users that are at risk for contracting the disease from the first subset of the plurality of users utilizing the model of the outbreak of the disease and the received location data for the plurality of users; and generating one or more notifications for delivery to at least one of the first and second subsets of the plurality of users, the one or more notifications comprising information related to outbreak of the disease and measures for at least one of treating the disease and mitigating spread of the disease;

wherein identifying the second subset of the plurality of users that are at risk for contracting the disease from the first subset of the plurality of users comprises:

determining colocation of at least a first user in the first subset of the plurality of users with at least a second user in the second subset of the plurality of users utilizing at least a first type of location data obtained from at least a first type of sensors of the plurality of wearable devices, the first type of location data comprising geographic location data and the first type of sensors comprising global positioning system (GPS) sensors;

determining one or more environmental characteristics of a local environment of geographic locations of the first user and the second user, the one or more environmental characteristics characterizing whether the first user and the second user are present at a given geographic location comprising a building with two or more units; and responsive to the determined one or more environmental characteristics indicating that the first user and the second user are present at the given geographic location, verifying colocation of the second user with the first user utilizing a second type of location data obtained from at least a second type of sensors of the plurality of wearable devices, the second type of location data comprising contextual location information for verifying presence of the second user and the first user within a common one of the two or more units of the building at the given geographic location; and wherein the method is performed by at least one processing device comprising a processor coupled to a memory.

* * * * *